United States Patent
Bauzon et al.

(10) Patent No.: US 11,530,401 B2
(45) Date of Patent: *Dec. 20, 2022

(54) SHORT-ACTING FACTOR VII POLYPEPTIDES

(71) Applicant: Coagulant Therapeutics Corporation, Seoul (KR)

(72) Inventors: Maxine Bauzon, Hercules, CA (US); Terry Hermiston, Mill Valley, CA (US)

(73) Assignee: Coagulant Therapeutics Corporation, Seoul (KR)

(*) Notice: Subject to any disclaimer, the term of this patent is extended or adjusted under 35 U.S.C. 154(b) by 105 days.

This patent is subject to a terminal disclaimer.

(21) Appl. No.: 16/896,646

(22) Filed: Jun. 9, 2020

(65) Prior Publication Data
US 2021/0002624 A1    Jan. 7, 2021

Related U.S. Application Data

(63) Continuation of application No. 15/265,703, filed on Sep. 14, 2016, now Pat. No. 10,717,970, which is a continuation of application No. 14/341,359, filed on Jul. 25, 2014, now Pat. No. 10,273,466, which is a continuation of application No. PCT/US2013/077405, filed on Dec. 23, 2013.

(60) Provisional application No. 61/787,026, filed on Mar. 15, 2013, provisional application No. 61/745,674, filed on Dec. 24, 2012.

(51) Int. Cl.
| | | |
|---|---|---|
| C12N 9/64 | (2006.01) | |
| A61K 38/36 | (2006.01) | |
| A61K 38/00 | (2006.01) | |
| A61K 38/48 | (2006.01) | |

(52) U.S. Cl.
CPC ........ *C12N 9/6437* (2013.01); *A61K 38/4846* (2013.01); *C12Y 304/21021* (2013.01); *A61K 38/00* (2013.01)

(58) Field of Classification Search
None
See application file for complete search history.

(56) References Cited

U.S. PATENT DOCUMENTS

| | | |
|---|---|---|
| 5,180,583 A | 1/1993 | Hedner |
| 7,371,543 B2 | 5/2008 | Pedersen et al. |
| 7,645,446 B2 | 1/2010 | Fang et al. |
| 7,807,174 B2 | 10/2010 | Fang et al. |
| 3,008,252 A1 | 8/2011 | DeFrees et al. |
| 8,012,733 B2 | 9/2011 | Van Dijk et al. |
| 8,273,723 B2 | 9/2012 | Zhang et al. |
| 2005/0221335 A1 | 10/2005 | Kavanagh |
| 2008/0056255 A1 | 3/2008 | Bolt et al. |
| 2008/0226681 A1 | 9/2008 | Goletz et al. |
| 2009/0291890 A1 | 11/2009 | Madison et al. |
| 2009/0305967 A1 | 12/2009 | DeFrees et al. |
| 2009/0311239 A1 | 12/2009 | Chtourou et al. |
| 2010/0026939 A1 | 2/2010 | Behrens et al. |
| 2010/0028939 A1 | 2/2010 | Behrens et al. |
| 2010/0062973 A1 | 3/2010 | Frank et al. |
| 2010/0081187 A1 | 4/2010 | Griffith et al. |
| 2010/0113743 A1 | 5/2010 | DeFrees et al. |
| 2010/0172911 A1 | 7/2010 | Naso et al. |
| 2010/0330645 A1 | 12/2010 | DeFrees et al. |
| 2011/0182875 A1 | 7/2011 | Fang et al. |
| 2011/0243960 A1 | 10/2011 | Gallo et al. |
| 2011/0263503 A1 | 10/2011 | Pieper et al. |
| 2015/0344863 A1 | 12/2015 | Bauzon et al. |

FOREIGN PATENT DOCUMENTS

| | | |
|---|---|---|
| WO | 1989/012097 A1 | 12/1989 |
| WO | 2003093465 A1 | 11/2003 |
| WO | 2004083361 | 9/2004 |
| WO | 2004111242 | 12/2004 |
| WO | 2005108568 A1 | 11/2005 |
| WO | 2005123916 | 12/2005 |
| WO | 2006114105 A2 | 11/2006 |
| WO | 2007013993 A1 | 2/2007 |
| WO | 2008/083150 A2 | 7/2008 |
| WO | 2001058935 A2 | 6/2011 |
| WO | 2011109600 A1 | 9/2011 |
| WO | 2013017555 A1 | 2/2013 |

OTHER PUBLICATIONS

Bork et al., "Increasing the Sialylation of Therapeutic Glycoproteins: The Potential of the Sialic Acid Biosynthetic Pathway," J. Pharm. Sciences, vol. 98, No. 10, Oct. 2009, pp. 3499-3508.
Herscovics, A. et al., "Glycoprotein Biosynthesis in Yeast," The FASEB Journal 7: 540-550, Apr. 1993.
European Search Report direct to EP Application 16196780.7; dated Feb. 1, 2017; 8 pages.
Hjortoe, G. et al., "Factor VIIa Binding and Internalization in Hepatocytes," J Thromb Haemost, 2005, vol. 3(10): 2264-2273.
Appa, R.S., et al., "Investigating Clearance Mechanisms for Recombinant Activated Factor VII in a Perfused Liver Model," 2010 Thrombosis and Haemostasis 104.2: 243-251.
International Search Report (PCT/ISA/210) dated May 1, 2014 by the U.S. Patent and Trademark Office as the International Searching Authority for International Application No. PCT/US2013/077405.
Dickinson et al., "Identification of Surface Residues Mediating Tissue Factor Binding and Catalytic Function of the Serine Protease Factor VIIa," Proc. Nat'l Acad. Sci USA, Dec. 1996, vol. 93, pp. 14379-14384.

(Continued)

*Primary Examiner* — Marsha Tsay
(74) *Attorney, Agent, or Firm* — Quarles & Brady LLP

(57) ABSTRACT

Short-acting Factor VII peptides are disclosed. A shortened half-life is desirable for treatment of acute bleeding and similar disorders. Modification of the sialylation and/or glycosylation of Factor VII and variants thereof produced peptides useful in treating conditions of acute bleeding.

22 Claims, 34 Drawing Sheets

Specification includes a Sequence Listing.

(56) References Cited

OTHER PUBLICATIONS

Iwanaga et al., Thromb Haemost (supplement Aug. 1999), 456, abstract 1474.
Toso et al., "Lack of Heavy Chain Glycosyiation in Patient with Factor VII Deficiency Not Responsible for Mutant FVIIa Activity," Blood, vol. 96, No. 11, part 2, Nov. 16, 2000, pp. 796 (42nd Annual Meeting of the American Society of Hematology).
Product Insert for NovoSeven Recombinant Factor VIIa, manufactured and sold by Novo Nordisk.
Roggentin et al., "Cloning and Sequencing of a Clostridium Perfringens Sialidase Gene," FEBS Letters, 238 (1), 31-34 (1988).
Calceti, P. et al., "Pharmacokinetic and Biodistribution Properties of Poly(ethylene glycol)-protein Conjugates," Adv Drug Deliv Rev., 2003, 55(10); pp. 1261-1277.
Weinstein, T. et al., "Distribution of Glycosaminoglycans in Rat Renal Tublar Epithelium," J Am Soc Nephrol, 1997, 8(4), 586-595.
Choi HS et al., "Renal Clearance of Nanoparticles," Nat Biotechnol., 2007, 25(10), 1165-1170.
Byrne, B et al., "Sialic Acids: Carbohydrate Moieties that Influence the Biological and Physical Properties of Biopharmaceutical Proteins and Living Cells," Drug Discovery Today, 2007, 12(7-8), pp. 319-326.
Seested et al., "The Unsialylated Subpopulation of Recombinant Activated Factor VII Binds to the Asialo-Glycoprotein (ASGPR) on Primary Rat Hepatocytes," Thrombosis and Harmostasis, 2010, vol. 104.6, pp. 1166-1173.
Lim et al., "The Golgi CMP-sialic Acid Transporter: a New CHO Mutant Provides Functional Insights," Glycobiology, vol. 18, No. 11, pp. 851-860, 2008.
Morell et al., "The Role of Sialic Acid in Determining the Survival of Glycoproteins in the Circulation," Journal of Biological Chemistry, vol. 246, No. 56 (Mar. 10, 1971), pp. 1461-1467.
Bolt et al., "Posttranslational N-glycosylation Takes Place During the Normal Processing of Human Coagulation Factor VII," Glycobiology, vol. 15, No. 5, pp. 541-547 (Dec. 2005).
Lim et al., "Engineering Mammalian Cells in Bioprocessing—Current Achievements and Future Perspectives," Biotechnol. Appl. Biochem., 2010, vol. 55, pp. 175-189.
Giles et al., "A Combination of Factor Xa and Phosphatidylcholine-phosphatidylserine Vesicles Bypasses Factor VIII in vivo," British Journal of Hematology, 1988, vol. 69, pp. 491-497.
Powell, J.S., "Lasting Power of New Clotting Proteins," Hematology 2014, pp. 355-366.
Sola et al., "Glycosylation of Therapeutic Proteins: An Effective Strategy to Optimize Efficacy," BioDrugs, 2010, 24(1), pp. 9-21.
Camire, R.M., "Bioengineered Factor Xa as a Potential New Strategy for Hemophilia Therapy," Expert Rev. Hematol., 5(2), pp. 121-123, 2012.

WILD TYPE FACTOR VII
GCCAACGCGTTCCTGGAGGAGCTGCGGCCGGGCTCCCTGGAGAGGGAGTGCAAGGAGGA
GCAGTGCTCCTTCGAGGAGGCCCGGGAGATCTTCAAGGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGAAATGCCAGCAAACCCCAAGGCCGAATTGTGGGGGGCAAGGTGTG
CCCCAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 1)

V1
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACAACGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGAAATGCCAGCAAACCCCAAGGCCGAATTGTGGGGGGCAAGGTGTG
CCCCAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGAACCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCCT (SEQ ID NO: 2)

Figure 1A

V2
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGAAGAGGAAACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACAACGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGAAATGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGAACCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 3)

pMB113
GCCAACGCGTTCCTGGAGGAGCTGCGGCCGGGCTCCCTGGAGAGGGAGTGCAAGGAGGA
GCAGTGCTCCTTCGAGGAGGCCCGGGAGATCTTCAAGGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGAAATGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 4)

Figure 1B pMB114
GCCAACGCGTTCCTGGAGGAGCTGCGGCCGGGCTCCCTGGAGAGGGAGTGCAAGGAGGA
GCAGTGCTCCTTCGAGGAGGCCCGGGAGATCTTCAAGGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGACAGGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 5)

pMB115
GCCAACGCGTTCCTGGAGGAGCTGCGGCCGGGCTCCCTGGAGAGGGAGTGCAAGGAGGA
GCAGTGCTCCTTCGAGGAGGCCCGGGAGATCTTCAAGGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGAAATGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCACAGATCACGGAGTACATGTTCTGTGCCGGCTACTCGGATGGCAGCAAGG
ACTCCTGCAAGGGGGACAGTGGAGGCCCACATGCCACCCACTACCGGGGCACGTGGTAC
CTGACGGGCATCGTCAGCTGGGGCCAGGGCTGCGCAACCGTGGGCCACTTTGGGGTGTA
CACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 6)

Figure 1C pMB116
GCCAACGCGTTCCTGGAGGAGCTGCGGCCGGGCTCCCTGGAGAGGGAGTGCAAGGAGGA
GCAGTGCTCCTTCGAGGAGGCCCGGGAGATCTTCAAGGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTAATATCCATGTGGAAAAATACCT
ATTCTAGAAAAAAGACAGGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCACAGATCACGGAGTACATGTTCTGTGCCGGCTACTCGGATGGCAGCAAGG
ACTCCTGCAAGGGGGACAGTGGAGGCCCACATGCCACCCACTACCGGGGCACGTGGTAC
CTGACGGGCATCGTCAGCTGGGGCCAGGGCTGCGCAACCGTGGGCCACTTTGGGGTGTA
CACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 7)

pMB117
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTAATATCCATGTGGAAAAATACCT
ATTCTAGAAAAAAGAAATGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 8)

Figure 1D pMB118
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTAATATCCATGTGGAAAAATACCT
ATTCTAGAAAAAAGACAGGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 9)

pMB119
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTAATATCCATGTGGAAAAATACCT
ATTCTAGAAAAAAGAAATGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCACAGATCACGGAGTACATGTTCTGTGCCGGCTACTCGGATGGCAGCAAGG
ACTCCTGCAAGGGGGACAGTGGAGGCCCACATGCCACCCACTACCGGGGCACGTGGTAC
CTGACGGGCATCGTCAGCTGGGGCCAGGGCTGCGCAACCGTGGGCCACTTTGGGGTGTA
CACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 10)

Figure 1E pMB120
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGCGGAGAGGACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGACAGGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCACAGATCACGGAGTACATGTTCTGTGCCGGCTACTCGGATGGCAGCAAGG
ACTCCTGCAAGGGGGACAGTGGAGGCCCACATGCCACCCACTACCGGGGCACGTGGTAC
CTGACGGGCATCGTCAGCTGGGGCCAGGGCTGCGCAACCGTGGGCCACTTTGGGGTGTA
CACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 11)

pMB121
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGAAGAGGAAACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGAAATGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 12)

Figure 1F pMB122
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGAAGAGGAAACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGACAGGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCAAATATCACGGAGTACATGTTCTGTGCCGGCTACTCGGATGGCAGCAAGGA
CTCCTGCAAGGGGACAGTGGAGGCCCACATGCCACCCACTACCGGGGCACGTGGTACC
TGACGGGCATCGTCAGCTGGGGCCAGGGCTGCGCAACCGTGGGCCACTTTGGGGTGTAC
ACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 13)

pMB123
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGAAGAGGAAACGAAGCTGT
TCTGGATTTCTTACAGTGATGGGGACCAGTGTGCCTCAAGTCCATGCCAGAATGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGAAATGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCACAGATCACGGAGTACATGTTCTGTGCCGGCTACTCGGATGGCAGCAAGG
ACTCCTGCAAGGGGACAGTGGAGGCCCACATGCCACCCACTACCGGGGCACGTGGTAC
CTGACGGGCATCGTCAGCTGGGGCCAGGGCTGCGCAACCGTGGGCCACTTTGGGGTGTA
CACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 14)

Figure 1G pMB124
GCCAACGCGTTCCTGGAGGAGCTGCGGCAGGGCTCCCTGGAGAGGGAGTGCAAGGAGGA
GCAGTGCTCCTTCGAGGAGGCCCGGGAGATCTTCGAAGACGAAGAGGAAACGAAGCTGT
TCTGGATTTCTTACAGTGATGGGGACCAGTGTGCCTCAAGTCCATGCCAGAATGGGGGCT
CCTGCAAGGACCAGCTCCAGTCCTATATCTGCTTCTGCCTCCCTGCCTTCGAGGGCCGGA
ACTGTGAGACGCACAAGGATGACCAGCTGATCTGTGTGAACGAGAACGGCGGCTGTGAG
CAGTACTGCAGTGACCACACGGGCACCAAGCGCTCCTGTCGGTGCCACGAGGGGTACTCT
CTGCTGGCAGACGGGGTGTCCTGCACACCCACAGTTGAATATCCATGTGGAAAAATACCT
ATTCTAGAAAAAAGACAGGCCAGCAAACCCCAAGGCCGAATTGTGGGGGGCAAGGTGTG
CCCCAAAGGGGAGTGTCCATGGCAGGTCCTGTTGTTGGTGAATGGAGCTCAGTTGTGTGG
GGGGACCCTGATCAACACCATCTGGGTGGTCTCCGCGGCCCACTGTTTCGACAAAATCAA
GAACTGGAGGAACCTGATCGCGGTGCTGGGCGAGCACGACCTCAGCGAGCACGACGGGG
ATGAGCAGAGCCGGCGGGTGGCGCAGGTCATCATCCCCAGCACGTACGTCCCGGGCACC
ACCAACCACGACATCGCGCTGCTCCGCCTGCACCAGCCCGTGGTCCTCACTGACCATGTG
GTGCCCCTCTGCCTGCCCGAACGGACGTTCTCTGAGAGGACGCTGGCCTTCGTGCGCTTC
TCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGG
AGACTCCCCACAGATCACGGAGTACATGTTCTGTGCCGGCTACTCGGATGGCAGCAAGG
ACTCCTGCAAGGGGGACAGTGGAGGCCCACATGCCACCCACTACCGGGGCACGTGGTAC
CTGACGGGCATCGTCAGCTGGGGCCAGGGCTGCGCAACCGTGGGCCACTTTGGGGTGTA
CACCAGGGTCTCCCAGTACATCGAGTGGCTGCAAAAGCTCATGCGCTCAGAGCCACGCCC
AGGAGTCCTCCTGCGAGCCCCATTTCCC (SEQ ID NO: 15)

Figure 1H

Wild Type Factor VII Peptide
ANAFLEELRPGSLERECKEEQCSFEEAREIFKDAERTKLFWISYSDGDQCASSPCQNGGS
CKDQLQSYICFCLPAFEGRNCETHKDDQLICVNENGGCEQYCSDHTGTKRSCRCHEGYSL
LADGVSCTPTVEYPCGKIPILEKRNASKPQGRIVGGKVCPKGECPWQVLLLVNGAQLCGG
TLINTIWVVSAAHCFDKIKNWRNLIAVLGEHDLSEHDGDEQSRRVAQVIIPSTYVPGTTN
HDIALLRLHQPVVLTDHVVPLCLPERTFSERTLAFVRFSLVSGWGQLLDRGATALELMVL
NVPRLMTQDCLQQSRKVGDSPNITEYMFCAGYSDGSKDSCKGDSGGPHATHYRGTWYLTG
IVSWGQGCATVGHFGVYTRVSQYIEWLQKLMRSEPRPGVLLRAPFP (SEQ ID NO: 16)

V1 Peptide
ANAFLEELRQGSLERECKEEQCSFEEAREIFEDAERTKLFWISYSDGDQCASSPCQNGGS
CKDQLQSYICFCLPAFEGRNCETHKDDQLICVNENGGCEQYCSDHNGTKRSCRCHEGYSL
LADGVSCTPTVEYPCGKIPILEKRNASKPQGRIVGGKVCPKGECPWQVLLLVNGAQLCGG
TLINTIWVVSAAHCFDKIKNWRNLIAVLGEHDLSEHDGDEQSRRVAQVIIPSTYVPGTTN
HDIALLRLHQPVNLTDHVVPLCLPERTFSERTLAFVRFSLVSGWGQLLDRGATALELMVL
NVPRLMTQDCLQQSRKVGDSPNITEYMFCAGYSDGSKDSCKGDSGGPHATHYRGTWYLTG
IVSWGQGCATVGHFGVYTRVSQYIEWLQKLMRSEPRPGVLLRAPFP (SEQ ID NO: 17)

V2 Peptide
ANAFLEELRQGSLERECKEEQCSFEEAREIFEDEEETKLFWISYSDGDQCASSPCQNGGS
CKDQLQSYICFCLPAFEGRNCETHKDDQLICVNENGGCEQYCSDHNGTKRSCRCHEGYSL
LADGVSCTPTVEYPCGKIPILEKRNASKPQGRIVGGKVCPKGECPWQVLLLVNGAQLCGG
TLINTIWVVSAAHCFDKIKNWRNLIAVLGEHDLSEHDGDEQSRRVAQVIIPSTYVPGTTN
HDIALLRLHQPVNLTDHVVPLCLPERTFSERTLAFVRFSLVSGWGQLLDRGATALELMVL
NVPRLMTQDCLQQSRKVGDSPNITEYMFCAGYSDGSKDSCKGDSGGPHATHYRGTWYLTG
IVSWGQGCATVGHFGVYTRVSQYIEWLQKLMRSEPRPGVLLRAPFP (SEQ ID NO: 18)

Figure 2

Example of a complex N-linked glycan

Figure 6

| pMB number | Backbone | N-glycosylation sites | |
|---|---|---|---|
| pMB113 | F7wt | N145, N322 | |
| pMB114 | | N145Q, N322 | |
| pMB115 | | N145, N322Q | |
| pMB116 | | N145Q, N322Q | |
| pMB117 | V1 | N145, N322 | |
| pMB118 | | N145Q, N322 | |
| pMB119 | | N145, N322Q | |
| pMB120 | | N145Q, N322Q | |
| pMB121 | V2 | N145, N322 | |
| pMB122 | | N145Q, N322 | |
| pMB123 | | N145, N322Q | |
| pMB124 | | N145Q, N322Q | |

| | FVII Chromo (ng/ml) | FVII ELISA (ng/ml) | Chromo/ELISA ratio |
|---|---|---|---|
| pMB113 | 740.4 | 788.2 | 0.9 |
| pMB114 | 619.8 | 601.0 | 1.0 |
| pMB115 | 554.2 | 426.8 | 1.3 |
| pMB116 | 498.9 | 430.0 | 1.2 |
| pMB117 | 1248.3 | 870.8 | 1.4 |
| pMB118 | 1272.1 | 890.5 | 1.4 |
| pMB119 | 601.7 | 346.8 | 1.7 |
| pMB120 | 292 | 236.8 | 1.2 |
| pMB121 | 166.3 | 808.2 | 0.2 |
| pMB122 | 155.6 | 711.9 | 0.2 |
| pMB123 | 181.5 | 514.5 | 0.4 |
| pMB124 | 78.9 | 277.2 | 0.3 |

Figure 12

Figure 17
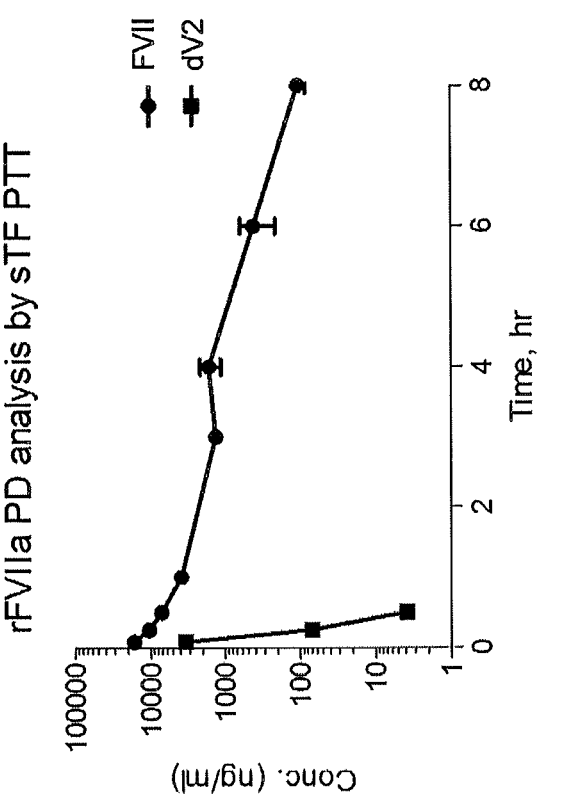
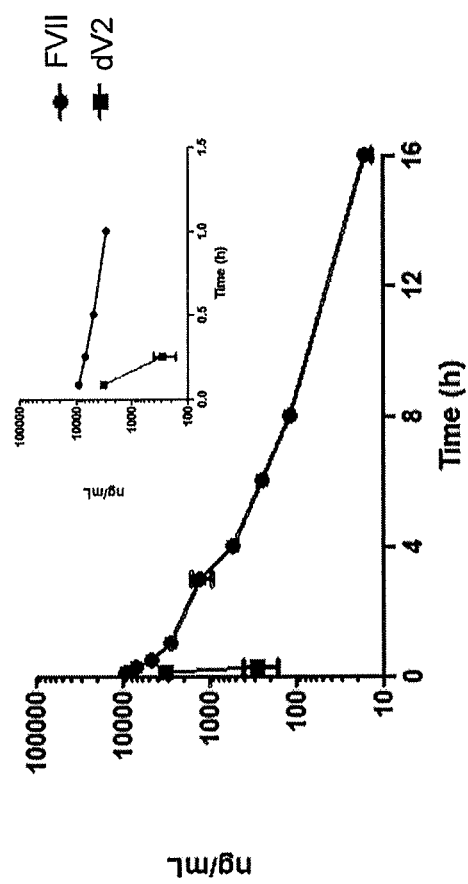

SHORT-ACTING FACTOR VII POLYPEPTIDES

CROSS REFERENCE TO RELATED APPLICATIONS

This application is a continuation of U.S. application Ser. No. 15/265,703 filed on Sep. 14, 2016, now U.S. Pat. No. 10,717,970, which is a continuation of U.S. application Ser. No. 14/341,359, filed on Jul. 25, 2014, now U.S. Pat. No. 10,273,466, which is a continuation of PCT Application No. PCT/US2013/077405 filed on Dec. 23, 2013 which claims priority to U.S. App. Ser. No. 61/745,674, filed Dec. 24, 2012, and U.S. App. Ser. No. 61/787,026, filed Mar. 15, 2013, all of which applications are hereby incorporated by reference in their entireties.

SEQUENCE LISTING SUBMISSION

The Sequence Listing associated with this application is filed in electronic format via EFS-Web and hereby incorporated by reference into the specification in its entirety. The name of the text file containing the Sequence Listing is 172085_00081SequenceListing_ST25. The size of the text file is 37 KB, and the text file was created on Sep. 11, 2020.

FIELD OF THE DISCLOSURE

Human coagulation Factor VII variants and the polynucleotides encoding such variants, vectors and host cells comprising and expressing such variants, methods of obtaining such variants, methods of using such variants, compositions of the variants, and additional inventive features related thereto are provided herein.

BACKGROUND

Blood coagulation is a process consisting of a complex interaction of various blood components (or factors) that eventually gives rise to a fibrin clot. Generally, the blood components, which participate in what has been referred to as the coagulation "cascade," are enzymatically inactive proteins (proenzymes or zymogens) that are converted to proteolytic enzymes by the action of an activator (which itself is an activated clotting factor). Coagulation factors that have undergone such a conversion are generally referred to as "active factors" and are designated by the addition of the letter "a" to the name of the coagulation factor (e.g., Factor VIIa).

Initiation of the haemostatic process is mediated by the formation of a complex between tissue factor, which is exposed to the circulating blood following injury to the vessel wall, and Factor VIIa, which is present in the circulation in an amount corresponding to about 1% of the total Factor VII protein mass. This complex is anchored to the tissue factor-bearing cell and converts Factors IX and X to their active forms Factor IXa and Factor Xa on the cell surface. Factor Xa converts prothrombin to thrombin on the tissue factor-bearing cell, which activates Factor VIII, Factor V, Factor XI, and Factor XIII Furthermore, the limited amount of thrombin formed in this initial step of haemostasis also activates the platelets. Following the action of thrombin on the platelets, the platelets change shape and expose charged phospholipids on their surface. This activated platelet surface forms the template for further Factor X activation and the full thrombin generation. The further Factor X activation on the activated platelet surface occurs via a Factor IXa and Factor VIIIa complex formed on the surface of the activated platelet, and Factor Xa then converts prothrombin into thrombin while still on the surface. Thrombin then converts fibrinogen into fibrin, which is insoluble and which stabilizes the initial platelet plug. This process is localized to the site of the tissue factor exposure thereby minimizing the risk of a systemic activation of the coagulation system. In recent years, Factor VII and tissue factor have been found to be the main initiators of blood coagulation.

Factor VIIa is produced from its precursor, Factor VII, which is synthesized in the liver and secreted into the blood where it circulates as a single-chain glycoprotein (molecular weight of about 50,000 Da). Wild-type Factor VII as used herein has the amino acid sequence and nucleotide sequence disclosed in FIGS. 1 and 2. The term "Factor VII" is meant to encompass Factor VII polypeptides in their uncleaved form (the zymogen form) as well as those that have been proteolytically or otherwise processed to yield their respective bioactive forms, which may be referred to as Factor VIIa. Wild type Factor VII is cleaved typically between residues 152 and 153 to produce Factor VIIa.

Factor VII is converted in vitro into the two-chain form Factor VIIa by Factor Xa, Factor XIIa, Factor IXa, or thrombin. Like several other plasma proteins involved in haemostasis, Factor VII is dependent on Vitamin K for its activity, which is required for the gamma-carboxylation of multiple glutamic acid residues that are clustered close to the amino terminus of the protein. These gamma-carboxylated glutamic acids are required for the metal ion-induced interaction of Factor VII with phospholipids. In the presence of tissue factor, phospholipids, and calcium ions, the two-chain Factor VIIa rapidly activates Factor X or Factor IX by limited proteolysis. Factor VIIa is susceptible to proteolytic cleavage, giving rise to a number of degradation products that do not have clotting activity.

Factor VII variants having an amino acid sequence derived from wild type Factor VII by substitution, deletion, and/or insertion of one or more amino acids have been published. For example, Dickinson et al. (Proc. Natl. Acad. Sci USA (1996) 93, 14379-14384) relates to Factor VII variants wherein Lys157, Val158, Glu296, Met298, Asp334, Ser336, or Lys227 have been individually replaced by Ala. Iwanaga et al. (Thromb. Haemost. (supplement August 1999), 466, abstract 1474) relates to Factor VIIa variants wherein residues 316-320 are deleted or residues 311-322 are replaced with the corresponding residues from trypsin. U.S. Pat. App. Pub. 2008/0058255 A1 to Bolt et al. relates to Factor VII variants having a glycosylation-disrupting substitution at either N145 or N322, or at both N145 and N322. Toso et al. reported a series of Factor VII structure-function studies based on naturally occurring mutations. The mutant recombinant Factor VII proteins included T324M, E385K, and two mutant Factor VII proteins lacking glycosylation core sequences in either the Factor VII heavy chain (N322Q) or the Factor VII light chain (N145Q). Toso et al., "Lack of Heavy Chain Glycosylation in Patient with Factor VII Deficiency Not Responsible for Mutant FVIIa Activity," Blood, vol. 96, no. 11, part 2 (16 Nov. 2000), p. 79b ($42^{nd}$ Annual Meeting of the American Society of Hematology).

Most naturally occurring peptides and proteins contain carbohydrate moieties attached to the peptide or protein via specific linkages to a select number of amino acids along the length of the primary peptide or protein chain. Thus, many naturally occurring peptides and proteins are termed "glycopeptides" or "glycoproteins," respectively. The variability of the glycosylation pattern on any given peptide or protein can impact the function of that peptide or protein. For example, the structure of the N-linked glycans on a peptide or protein can impact various characteristics of the peptide or protein, including the protease susceptibility, intracellular trafficking, secretion, tissue targeting, biological half-life, and antigenicity of the peptide or protein in a cell or organism. The alteration of one or more of these characteristics can affect the efficacy of a peptide or protein in its natural setting, and can also affect the efficacy of the peptide or protein as a therapeutic agent in situations where the peptide or protein has been generated for that purpose.

The carbohydrate structure attached to the peptide or protein chain is known as a "glycan" molecule. The specific glycan structure present on a peptide or protein affects the solubility and aggregation characteristics of the peptide or protein, the folding of the primary peptide or protein chain, and, therefore, its functional or enzymatic activity, the resistance of the peptide or protein to proteolytic attack, and the control of proteolysis leading to the conversion of inactive forms of the peptide or protein to active forms. For example, terminal sialic acid residues present on the glycan molecule affect the length of the half-life of the peptide or protein in the mammalian circulatory system. Peptides and proteins whose glycans do not contain terminal sialic acid residues generally are more rapidly removed from the circulation by the liver.

The glycan structures found in naturally occurring glycopeptides and glycoproteins are typically divided into two classes, N-linked and O-linked glycans. Wild type Factor VIIa contains two N-linked and two O-linked glycosylation sites. N-linked glycosylation is the most common covalent modification in eukaryotes. N-linked glycosylation occurs at the consensus sequence Asn-X-Ser/Thr, where the glycan attaches to the amine group of asparagine and X represents any amino acid except proline. N-linked glycans are based on the common core pentasaccharide, $Man_3(GlcNAc)_2$, which can be further modified by the addition of monosaccharides such as N-acetyl galactosamine, galactose, neuraminic acid, N-acetylglucosamine, fructose, mannose, and fucose. The $Man_3(GlcNAc)_2$ core with various monosaccharides including terminal sialic acids may be attached via a N-acetylglucosamine to at the Asn in the Asn-X-Ser/Thr consensus sequence. This chemically complex co-translational modification serves many purposes and affects the biology of the protein in diverse ways including proper folding, functional group orientation, and clearance rates.

A variety of methods have been proposed in the art to customize the glycosylation pattern of a peptide or protein, including those described in U.S. Pat. No. 8,008,252 to DeFrees et al.

It is often desirable to stimulate or improve the coagulation cascade in a subject. Factor VIIa has been used to control bleeding disorders caused by clotting factor deficiencies (e.g., haemophilia A and B or deficiency of coagulation Factors XI or VII) or clotting factor inhibitors. Recombinant Factor VIIa, manufactured and sold by Novo Nordisk under the trade name NovoSeven®, is approved for the for the treatment of bleeding episodes in hemophilia A or B patients with inhibitors to Factor VIII or Factor IX and in patients with acquired hemophilia; prevention of bleeding in surgical interventions or invasive procedures in hemophilia A or B patients with inhibitors to Factor VIII or Factor IX and in patients with acquired hemophilia; treatment of bleeding episodes in patients with congenital Factor VII deficiency and prevention of bleeding in surgical interventions or invasive procedures in patients with congenital Factor VII deficiency. U.S. Pat. No. 5,180,583 to Hedner discloses using Factor VIIa to control excessive bleeding in situations not caused by clotting factor defects or clotting factor inhibitors. Hedner discloses treating bleeding disorders caused for example by a defective platelet function, thrombocytopenia, or von Willebrand's disease, and compositions for those uses.

There is a need to treat bleeding from disorders not caused by congenital or developed clotting factor deficiencies or inhibitors to clotting factors. Several clinical trials have demonstrated the efficacy of recombinant Factor VIIa to control bleeds. However, there are concerns over an increase in undesirable thromboembolic events from use of this molecule. Bleeding is a major problem in many disorders, such as in connection with surgery, complications following surgery, stem and organ transplants, intracranial hemorrhage, aortic aneurysm, and trauma, or overdose of certain anti-coagulants.

BRIEF SUMMARY

It is an object to treat bleeding disorders and episodes with Factor VII polypeptides that are short-acting. One object of the present work is to provide compositions of Factor VII polypeptides (wild-type or variant) that are short-acting, characterized by one or more pharmacokinetic traits such as a shortened half-life. It is an object to provide such a Factor VII molecule with reduced opportunity for thrombotic events outside of the target site and the treatment timeframe. It is an object to provide Factor VII polypeptides (wild-type or variant) with enhanced clearance due to altered glycosylation patterns.

Described herein is a composition of variant Factor VII polypeptides, in which the variant Factor VII polypeptide comprises an amino acid sequence having at least two sequence alterations relative to the amino acid sequence of SEQ ID NO: 16, wherein the at least two sequence alterations are (1) a glutamine residue substituted for the proline residue in position 10, and (2) a glutamic acid residue substituted for the lysine residue in position 32; and wherein the ratio of moles of conjugated sialic acid to moles of N-linked glycan in the composition is less than 0.05, less than 0.1, less than 1.0, less than 2.0, less than 3.0, less than 4.0, less than 5.0 or less than 6.0. Also described herein is a composition of variant Factor VII polypeptides in which the variant Factor VII polypeptide comprises an amino acid sequence having at least two sequence alterations relative to the amino acid sequence of SEQ ID NO: 16, wherein the at least two sequence alterations are (1) a glutamine residue substituted for the proline residue in position 10, and (2) a glutamic acid residue substituted for the lysine residue in position 32; and wherein the ratio of moles of conjugated sialic acid per mole of N-linked glycan is within a range selected from the group consisting of (1) from 0 to 5; (2) from 0 to 4; (3) from 0 to 3; (4) from 0 to 2; (5) from 0 to 1 and (6) from 0 to 0.5.

Also described herein is an isolated variant Factor VII polypeptide comprising an amino acid sequence having at least two sequence alterations relative to the amino acid sequence of SEQ ID NO: 16, wherein the at least two sequence alterations are (1) a glutamine residue substituted for the proline residue in position 10, and (2) a glutamic acid residue substituted for the lysine residue in position 32, wherein the polypeptide has a ratio of moles of conjugated sialic acid to moles of N-linked glycan of less than 0.05, less than 0.1, less than 1.0, less than 2.0, less than 3.0, less than 4.0, less than 5.0 or less than 6.0. Also described herein is a composition of Factor VII polypeptides, wherein the Factor VII polypeptides comprise the amino acid sequence of SEQ ID NO: 16 (wild type Factor VII) and the ratio of moles of conjugated sialic acid to moles of N-linked glycan in the composition is within a range selected from the group consisting of (1) from 1 to 5; (2) from 1 to 4; (3) from 1 to 3; (4) from 1 to 2; and (5) from 0.5 to 1; or conjugated sialic acid is undetectable.

Also described herein is an isolated variant Factor VII polypeptide selected from the group consisting of:

(1) a polypeptide comprising a Factor VII amino acid sequence having sequence alterations relative to the sequence of SEQ ID NO: 16, wherein the sequence alterations consist of (1) a glutamine residue substituted for the proline residue in position 10, (2) a glutamic acid residue substituted for the lysine residue in position 32, and (3) a sequence alteration such that N-linked glycosylation at position 145 is disrupted;

(2) a polypeptide comprising a Factor VII amino acid sequence having sequence alterations relative to the sequence of SEQ ID NO: 16, wherein the sequence alterations consist of (1) a glutamine residue substituted for the proline residue in position 10, (2) a glutamic acid residue substituted for the lysine residue in position 32, and (3) a sequence alteration such that N-linked glycosylation at position 322 is disrupted;

(3) a polypeptide comprising a Factor VII amino acid sequence having sequence alterations relative to the amino acid sequence of SEQ ID NO: 16, wherein the sequence alterations consist of (1) a glutamine residue substituted for the proline residue in position 10, and (2) a glutamic acid residue substituted for the lysine residue in position 32, and (3) sequence alterations such that N-linked glycosylation at positions 145 and 322 is disrupted;

(4) a polypeptide comprising a Factor VII amino acid sequence having sequence alterations relative to the amino acid sequence of SEQ ID NO: 16, wherein the sequence alterations consist of (1) a glutamine residue substituted for the proline residue in position 10, and (2) a glutamic acid residue substituted for the lysine residue in position 32, wherein positions 145 and 322 are asparagine and have attached N-linked glycosylation;

(5) a polypeptide comprising a Factor VII amino acid sequence having sequence alterations relative to the amino acid sequence of SEQ ID NO: 16, wherein the sequence alterations consist of (1) a glutamine residue substituted for the proline residue in position 10, (2) a glutamic acid residue substituted for the lysine residue in position 32, (3) a glutamic acid residue substituted for the alanine residue in position 34, (4) a glutamic acid residue substituted for the arginine residue in position 36, and (5) a sequence alteration such that N-linked glycosylation at position 145 is disrupted;

(6) a polypeptide comprising a Factor VII amino acid sequence having sequence alterations relative to the amino acid sequence of SEQ ID NO: 16, wherein the sequence alterations consist of (1) a glutamine residue substituted for the proline residue in position 10, (2) a glutamic acid residue substituted for the lysine residue in position 32, (3) a glutamic acid residue substituted for the alanine residue in position 34, (4) a glutamic acid residue substituted for the arginine residue in position 36, and (5) a sequence alteration such that N-linked glycosylation at position 322 is disrupted;

(7) a polypeptide comprising a Factor VII amino acid sequence having sequence alterations relative to the amino acid sequence of SEQ ID NO: 16, wherein the sequence alterations consist of (1) a glutamine residue substituted for the proline residue in position 10, (2) a glutamic acid residue substituted for the lysine residue in position 32, (3) a glutamic acid residue substituted for the alanine residue in position 34, (4) a glutamic acid residue substituted for the arginine residue in position 36, and (5) a sequence alterations such that N-linked glycosylation at positions 145 and 322 is disrupted; and (8) a polypeptide comprising a Factor VII amino acid sequence having sequence alterations relative to the amino acid sequence of SEQ ID NO: 16, wherein the sequence alterations consist of (1) a glutamine residue substituted for the proline residue in position 10, (2) a glutamic acid residue substituted for the lysine residue in position 32, (3) a glutamic acid residue substituted for the alanine residue in position 34, and (4) a glutamic acid residue substituted for the arginine residue in position 36, wherein positions 145 and 322 are asparagine and have attached N-linked glycosylation.

Also described herein are Factor VII polypeptides having reduced conjugation of sialic acid with the Factor VII polypeptide. In certain examples, the Factor VII polypeptide is a variant polypeptide that produces altered glycosylation pattern. In other examples, the Factor VII polypeptide is a wild-type Factor VII polypeptide which has reduced conjugation of sialic acid. In certain embodiments, reduced silica acid conjugation can be effectuated by treatment of the polypeptide with a sialidase enzyme. In other embodiments, reduced sialic acid conjugation can be effectuated by producing recombinant Factor VII polypeptides in a cell line that is partially or completely deficient in sialylation of peptides. In further embodiments, the reduced sialic acid conjugation can be effectuated by coexpressing the recombinant Factor VII polypeptide and a recombinant or exogenous sialidase enzyme in a cell line.

Also described is a method for treating a mammal having a disease or a disorder wherein blood clot formation is desirable, comprising administering to a mammal in need thereof an effective amount of a Factor VII polypeptide that has reduced sialic acid conjugation. In certain embodiments, the ratio of moles of conjugated sialic acid to moles of N-linked glycan is less than 0.05. In other embodiments, the Factor VII polypeptide comprises the amino acid sequence of SEQ ID NO: 16. In further embodiments, the Factor VII polypeptide comprises wild-type factor VII. In additional embodiments, the disease or disorder being treated is selected from the group consisting of a hemorrhage, gastrointestinal bleeding, uncontrolled bleeding, bleeding in a mammal undergoing transplantation or resection or surgery, variceal bleeding, thrombocytopenia, hemophilia, intracranial hemorrhage, aortic aneurysm, and over administration of an anticoagulant.

Further variants, compositions, methods and related products and processes are disclosed in detail below.

BRIEF DESCRIPTION OF THE DRAWINGS

FIGS. 1A-1H show the nucleotide sequences for three Factor VII molecules used in the present application. "V1" is a variant of human Factor VII having four amino acid mutations relative to wild type human amino acid sequence of SEQ ID NO: 16: (P10Q, K32E, T106N and V253N). "V2" is a variant of human Factor VII having six amino acid mutations relative to wild type human amino acid sequence of SEQ ID NO: 16: (P10Q, K32E, A34E, R36E, T106N and V253N). FIG. 1 also shows the nucleotide sequences for various constructs used in the examples.

FIG. 2 shows the amino acid sequences for three Factor VII molecules used in the present application. Wild type human Factor VII as used herein has the amino acid sequence of SEQ ID NO: 16. V1 has the amino acid sequence of SEQ ID NO: 17. V2 has the amino acid sequence of SEQ ID NO: 18. In V1 and V2, the changes from wild type Factor VII of SEQ ID NO: 16 are shown in bold.

FIG. 6 is a table of hypoglycosylated Factor VII molecules.

FIG. 12 is a table showing determination of "specific activity" of hypoglycosylated FVII variants using transfection supernatants.

FIG. 17 shows a pharmacokinetic study results in HemA mice.

DETAILED DESCRIPTION

Methods for modulating the pharmacokinetics of recombinant Factor VII polypeptides (wild-type or variant) to limit thrombotic complications in treatment of acute bleeding are described herein. Also described are Factor VII polypeptides with reduced sialic acid conjugation. Further described are variants of recombinant Factor VII with enhanced clearance from the blood and a decrease in the duration of efficacy. Such variants have a shorter half-life in vivo than recombinant wild type Factor VII, due to altered glycosylation patterns. Also described are methods of production and use of such short-acting Factor VII polypeptides.

Figure 3:
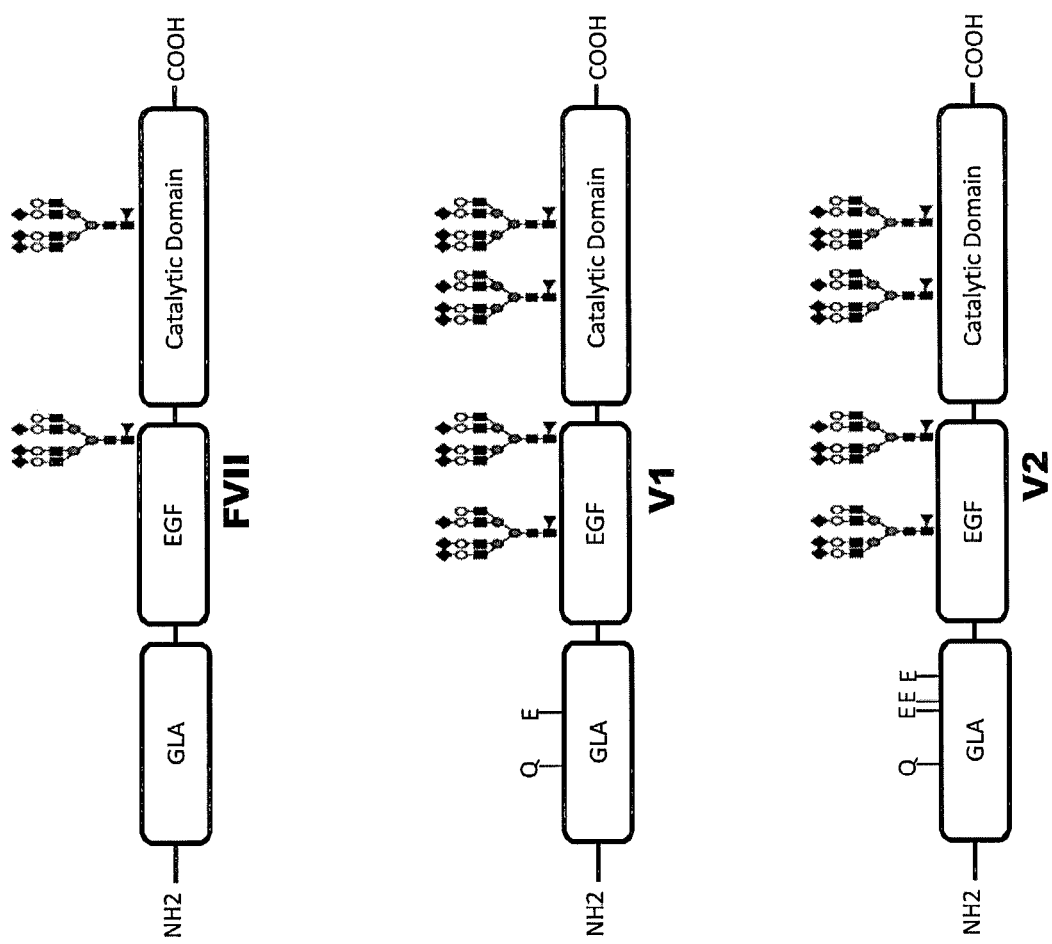
FIG. 3 is a scheme depicting three Factor VII molecules used in the examples of the present application. Attachment of glycans at N-glycosylation sites is shown. For the depiction of the glycans, a solid box represents N-acetylglucosamine, a shaded oval represents mannose, an open oval represents galactose, a dark diamond represents sialic acid (also known as N-acetylneuraminic acid) and a closed triangle represents fucose. The glycan structure is a depiction using one possible variant of a glycan and does not represent an actual measured glycan.
Figure 4:
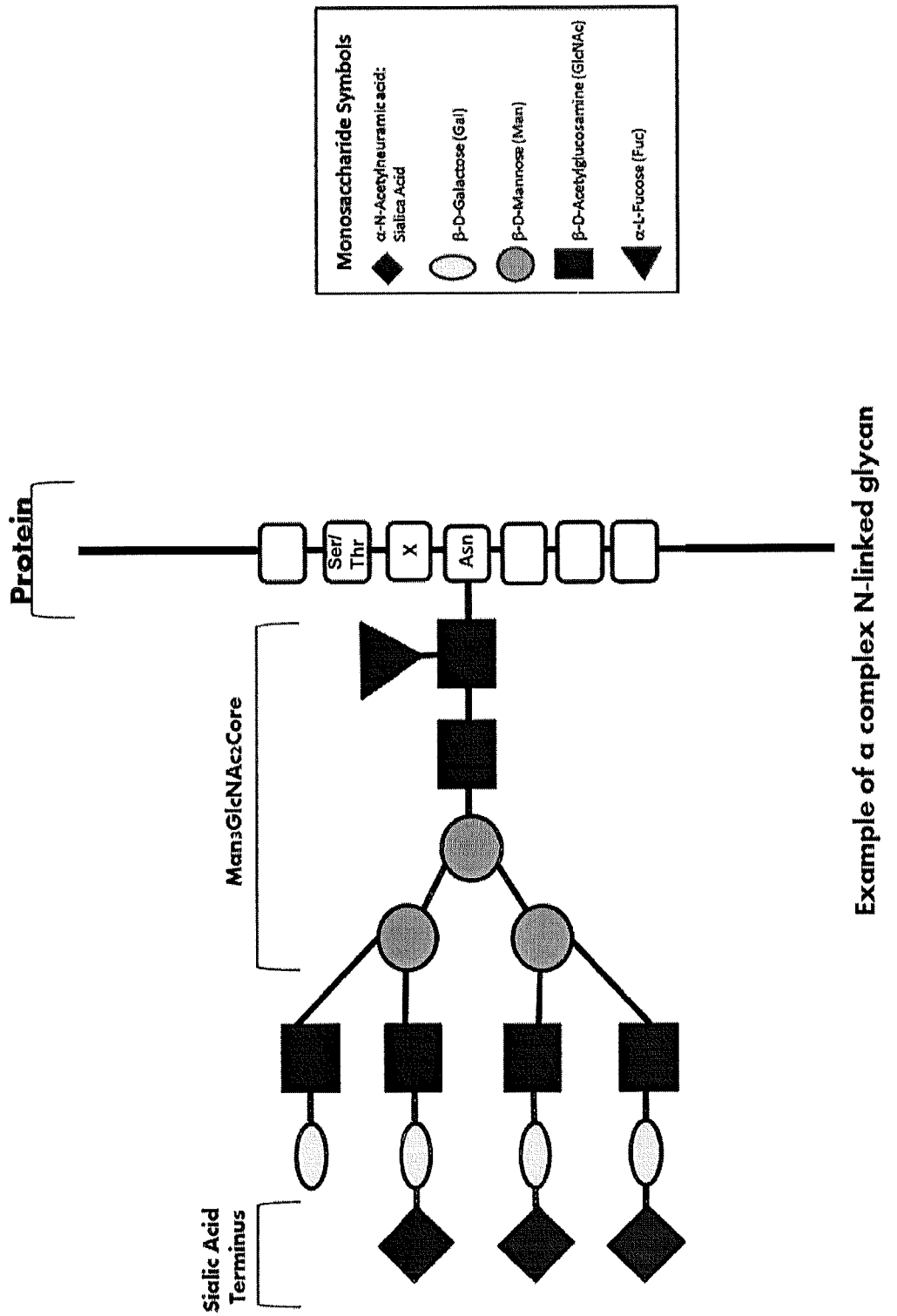
FIG. 4 is a scheme depicting an N-linked glycan showing attachment at the Asn in the Asn-X-Ser/Thr consensus sequence. The $Man_3(GlcNAc)_2$ core with various monosaccharides including terminal sialic acids are shown.

To explain Factor VII and glycosylation, FIGS. 3 and 4 are provided. FIG. 3 shows schematically three examples of Factor VII molecules with their domains. Factor VII is a protein consisting of a Gla, EGF, and catalytic domain and containing 2 N-linked Glycans (N145 and N322). V1 is a Factor VII variant with four mutations (P10Q, K32E, T106N, V253N). V2 is a Factor VII variant with six mutations (P10Q, K32E, A343, R36E, T106N, V253N). V1 and V2 both have increased affinity for activated platelets and contain two additional N-glycosylation sites resulting in longer half-lives as compared to wild type Factor VII. The two mutations found solely in V2 (A34E, R36E) are believed to account for its tissue-factor-independence.

FIG. 4 shows schematically an example of an N-linked glycan showing attachment at the Asn in the Asn-X-Ser/Thr consensus sequence. The $Man_3(GlcNac)_2$ core with various monosaccharides including terminal sialic acids are shown.

Figure 5:
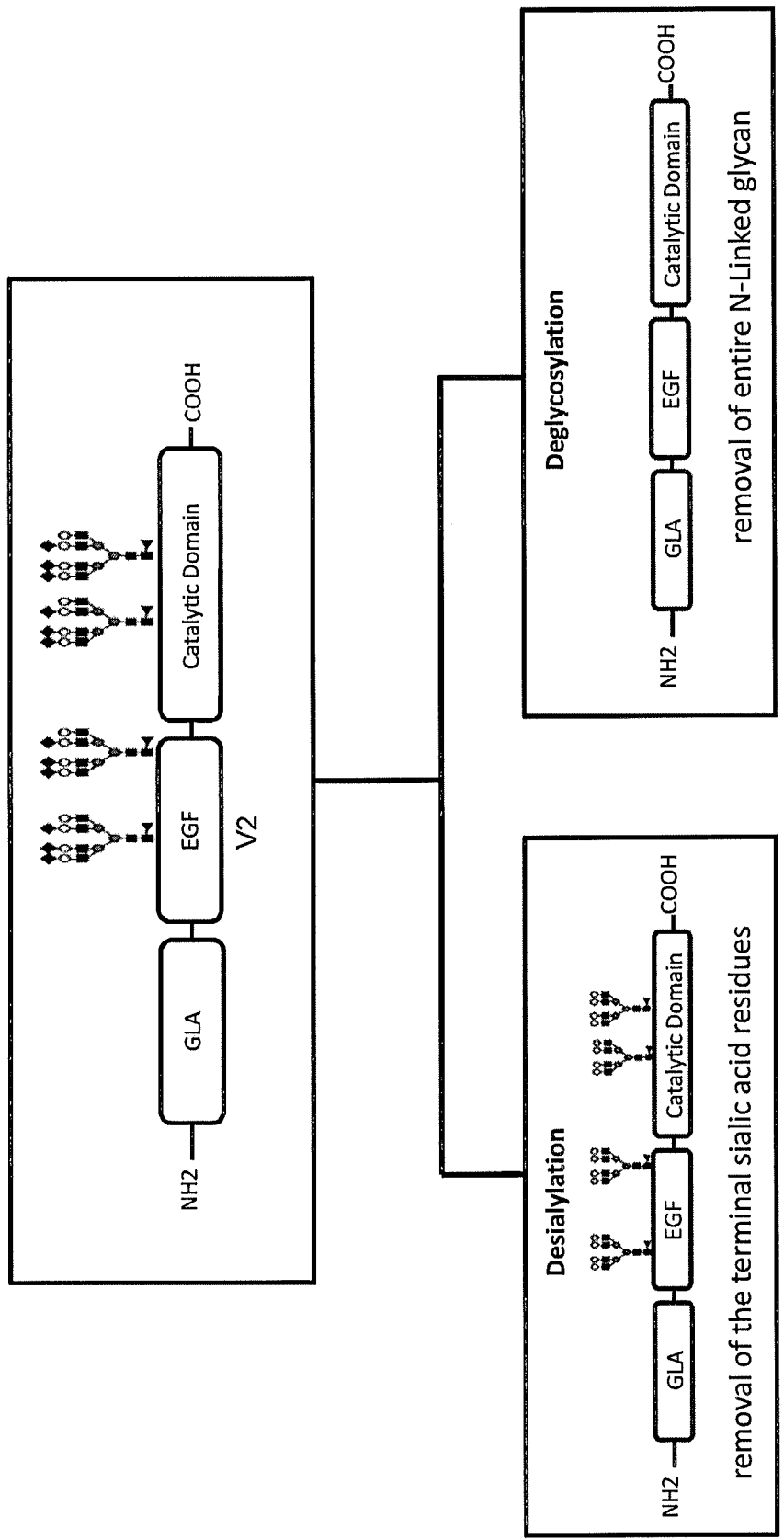
FIG. 5 is a scheme depicting two approaches used in the present disclosure to decrease the half-life of Factor VII variants, exemplified with reference to V2.

Methods of preparing a Factor VII polypeptide having a desired short half-life is provided herein. Two general methods are provided to make a short-acting Factor VII polypeptide, which methods can be used separately or in combination. As shown schematically in FIG. 5 using one example of a Factor VII variant, a glycosylated Factor VII variant can be processed by desialylation or deglycosylation to alter the glycosylation pattern of the variant and thereby to alter, and preferably shorten, its half-life. This method could also be used to desialylate a wild-type Factor VII polypeptide.

Desialylation may occur by any method known in the art. Examples of suitable methods include enzymatic desialylation by contact with any known enzyme that functions to desialylate including, without limitation, sialidases including neuraminidase-agarose beads (Sigma N5254) and the neuraminidase from *Clostridium perfringens* identified at GI:40479 and in FEBS Lett. 238 (1), 31-34 (1988). Such desialylation may be accomplished by contacting a partially purified recombinant Factor VII polypeptide with a sialidase in vitro under suitable conditions, or by co-expression of the sialidase in the host cell expressing the recombinant Factor VII polypeptide. The contacting in vitro may be of such duration that only partial desialylation occurs. For example, where a desired half-life can be obtained from a molecule with a ratio of from 0.5 to 1 moles of conjugated sialic acid to moles of N-linked glycan in the composition of Factor VII polypeptides, then contacting with a sialidase for a limited period of time before full desialylation occurs is recommended. Partial desialylation may also be obtained by using a modified sialidase, by contacting the Factor VII polypeptide with the sialidase under conditions that slow or impair the full functioning of the sialidase, or by other methods apparent to those skilled in the art to produce only partially desialylated polypeptides. Partial desialylation may be measured by comparison to the ratio of conjugated sialic acid to glycan in a reference preparation having been fully desialylated.

Desialylation may also be accomplished through expression of the Factor VII polypeptide (wild-type or variant) in a cell line that lacks or is deficient in one or more cellular components needed for sialic acid addition. Certain cell lines have been or may be modified to reduce or remove sialylation. For example, Lec2 cells with Chinese hamster ovary ("CHO") origin produce glycoproteins with approximately ten-fold less sialic acid than the wild type cell. It is believed that desialylation of a glycan results in a molecule that can be actively cleared by liver receptors including the Asialoglycoprotein Receptor (ASGPR) and for this reason it shortens half-life.

The second approach is to deglycosylate a Factor VII variant and thereby obtain a molecule with a shortened half-life. Reduction in glycosylation enhances clearance of Factor VII through renal clearance (50-60Kd cut off, rev. in Caliceti P and Veronese F M, "Pharmacokinetic and biodistribution properties of poly(ethylene glycol)-protein conjugates," Adv Drug Deliv Rev. 2003; 55(10):1261-77, Weinstein T et al., "Distribution of glycosaminoglycans in rat renal tubular epithelium," J Am Soc Nephrol. 1997; 8(4): 586-95, Choi H S et al., "Renal clearance of quantum dots," Nat Biotechnol. 2007; 25(10):1165-70), surface charge and isoelectric point (pI) change (which have been related to the increase in glycoprotein circulation, see review in Byrne B. et al., "Sialic acids: carbohydrate moieties that influence the biological and physical properties of biopharmaceutical proteins and living cells," Drug Discovery Today 2007; 12(7-8):319), and through less glycoprotein-mediated protection from any number of plasma proteases (Ton G., et al., 2005, Nie Y et al., 2006).

Deglycosylation as used herein includes, without limitation, a genetic modification of a Factor VII polypeptide that results in an altered amino acid sequence as compared to a reference Factor VII polypeptide, which alteration removes an N-linked glycosylation site. For example, a Factor VII variant can be produced with a glycosylation-disrupting alteration at one or more amino acid residues required for the N-linked glycan consensus sequence, i.e., Asn-X-Ser/Thr where X represents any amino acid except proline. As used herein a "glycosylation-disrupting alteration" of a Factor VII amino acid sequence refers to an alteration relative to wild type Factor VII that results in a substitution, addition, or deletion of one or more amino acid residues and that results in a loss of one or more sites for N-linked glycosylation. For example, N-linked glycosylation sites may be removed by replacing N145 and/or N322, both present in wild type Factor VII, with any amino acid (naturally occurring or non-naturally occurring). Glycosylation sites should be identified that have minimal effect on activity when altered to disrupt glycosylation. In another example, deglycosylation may occur by expression of the Factor VII polypeptide (wild-type or variant) in a cell line that lacks the machinery for glycosylation. For example, Factor VII produced in bacterial cells is expected to be completely unglycosylated because bacterial cells lack the cellular machinery for glycosylation. In another embodiment, the Factor VII polypeptide is produced in a cell line that lacks terminal glycosylation enzymes or that has such enzymes but one or more have activity that is less than that found in the wild type cell line. See, e.g., Appa R. et al., 201, Narita M et al., 1998, Seested et al., 2010. In another embodiment, the Factor VII polypeptide is produced in a cell line that harbors a defect in an enzyme involved in the synthesis or attachment of a glycan to Factor VII or a defect in an enzyme involved in the synthesis of CMP-sialic acid transporter. In another embodiment, the Factor VII polypeptide is treated with deglycosylase or chemicals to deglycosylate.

Treatment by sialidase, deglycosylase, or chemicals to reduce or remove glycans from a Factor VII polypeptide may occur during expression, purification, or post-purification.

In one embodiment, at least one of the N-linked glycosylation sites in Factor VII variant V1 (N322, N145) or Factor VII variant V2 (N322, N145, N106, N253) was selectively removed with a minimal effect on activity. The N-glycan site was obliterated at the DNA level by disrupting the N-glycan consensus sequence. This was done by removal of the N (Asparagine) codon and replacement with the Q (Glutamine) codon. FIG. 6 is a table showing examples of hypoglycosylated variants. Glycosylation variants were made on wild type Factor VII (referred to herein as "F7"), V1, and V2 backbones. The engineered N-Glycan sites (N106, N253) in V1 and V2 were reverted back to their wild type sequence (T106, V253). Variants pMB113, pMB117, and pMB121 are wild type Factor VII, V1, and V2 constructs respectively containing the two endogenous N-glycosylation sites (N145, N322). All other variants in FIG. 6 have had one or both of their endogenous N-glycan sites removed by introducing N to Q mutations (N145Q, N322Q). This deglycosylation approach results in faster clearance.

In one aspect of the present disclosure, deglycosylation and desialylation are combined to result in Factor VII polypeptides having desirable shortened half-lives. For example, a Factor VII molecule may be genetically modified to include additional N-linked glycosylation sites beyond the two present in wild type Factor VII. This variant may then be desialylated using one of the methods described herein. The resulting molecule may then retain the glycan structure at each N-linked glycosylation site without the terminal sialic acid. In experiments reported herein, Applicants report such variants that have a faster elimination time than a similar desialylated Factor VII variant that had fewer N-linked glycosylation sites. Similarly, a Factor VII polypeptide having only the two N-linked glycosylation sites found in wild type Factor VII may be deglycosylated at one of these sites and then subjected to desialylation. The resulting Factor VII variant having one N-linked glycan lacking sialic acid has different pharmacokinetics than the similar Factor VII polypeptide that did not lack a second N-linked glycosylation site based on the experimental evidence reported herein.

Definitions and Embodiments

Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and polypeptide synthesis. The nomenclature used herein and the laboratory procedures in analytical chemistry and organic synthesis described below are those well-known and commonly employed in the art. Standard techniques, or modifications thereof, are used for chemical syntheses and chemical analyses. Procedures used for genetic engineering are well known and can be found, for example, in Sambrook et al., Molecular Cloning: A Laboratory Manual, Cold Spring Harbor, N.Y.

The term "sialic acid" or "sialyl" refers to any member of a family of nine-carbon carboxylated sugars. The most common member of the sialic acid family is N-acetylneuraminic acid (2-keto-5-acetamido-3,5-dideoxy-D-glycero-D-galactononulopyranos-1-onic acid (often abbreviated as Neu5Ac, NeuAc, or NANA)).

The terms "polypeptide" and "protein" are used interchangeably herein and refer to a polymer in which the monomers are amino acids and are joined together through amide bonds. Additionally, unnatural amino acids, for example, β-alanine, phenylglycine, and homoarginine, are also included. Amino acids that are not gene-encoded can also be used with the technology disclosed herein. Furthermore, amino acids that have been modified to include reactive groups, glycosylation sites, polymers, therapeutic moieties, biomolecules, and the like can also be used. All of the amino acids used herein can be either the D- or L-isomer. The L-isomer is generally preferred. As used herein, "polypeptide" and "protein" refer to both glycosylated and unglycosylated polypeptides and proteins, respectively.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g. homoserine, norleucine, methionine sulfoxide, methionine methyl sulfonium. Such analogs have modified R groups (e.g. norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

The term "half-life" or "t1/2," as used herein in the context of administering a polypeptide or protein drug to a patient, is defined as the time required for plasma concentration of a drug in a patient to be reduced by one half.

Half-life can be determined in test animals, for example, by administering a dose of about 25-250 microgram/kg of the preparation; obtaining plasma samples at predetermined times after administration; and determining the content of the Factor VII polypeptide in the samples using one or more of a clotting assay (or any bioassay), an immunoassay, or an equivalent. The data can be displayed graphically and then the bioavailability will be determined as the area under the curve. In certain examples, rat or murine models are used for half-life measurements. Relative bioavailability of a Factor VII polypeptide or composition thereof refers to the ratio of the area under the curve of the short-acting Factor VII polypeptide to that of wild-type Factor VII or another appropriate comparator polypeptide or protein. Any Factor VII variant that has blood coagulation activity of Factor VII is useful for the purposes and methods described herein. Factor VII variants as used herein are polypeptides. The terms "variant Factor VII polypeptides" and "Factor VII variants" are used interchangeably herein. In one embodiment, the Factor VII variants have an amino acid sequence derived from wild type Factor VII (SEQ ID NO: 16) by substitution, deletion, and/or insertion of one or more amino acids. In designating amino acid substitutions, the first letter represents the amino acid present in the wild type human Factor VII at a position. The following number represents the position in human wild type Factor FVII. The second letter represents the amino acid replacing the amino acid found in the wild type. For example, "P10Q" represents a substitution of a glutamine (Q) for a proline (P) at amino acid position 10.

In certain examples, the Factor VII variant comprises one or more amino acid substitutions selected from the group consisting of P10Q, K32E, R36E, A34E, T106N, and V253N. In other examples, the Factor VII variant comprises at least 2, 3, 4, 5, or 6 of these substitutions. In further examples, the Factor VII variant comprises an amino acid sequence having at least two sequence alterations relative to the amino acid sequence of SEQ ID NO: 16 (wild type human Factor VII), wherein the at least two sequence alterations are (1) a glutamine residue substituted for the proline residue in position 10, and (2) a glutamic acid residue substituted for the lysine residue in position 32. In another example, the Factor VII variant comprises an amino acid sequence having at least three sequence alterations relative to the amino acid sequence of SEQ ID NO: 16, wherein the at least three sequence alterations are (1) a glutamine residue substituted for the proline residue in position 10, (2) a glutamic acid residue substituted for the lysine residue in position 32, and (3) a glutamic acid residue substituted for the arginine residue in position 36. In a further example, the Factor VII variant comprises an amino acid sequence having at least four sequence alterations relative to the amino acid sequence of SEQ ID NO: 16, wherein the at least four sequence alterations are (1) a glutamine residue substituted for the proline residue in position 10, (2) a glutamic acid residue substituted for the lysine residue in position 32, (3) a glutamic acid residue substituted for the arginine residue in position 36, and (4) a glutamic acid residue substituted for the alanine residue in position 34. In one particular example, the Factor VII variant comprises an amino acid sequence having at least six sequence alterations relative to the amino acid sequence of SEQ ID NO: 16, wherein the at least six or six sequence alterations are (1) a glutamine residue substituted for the proline residue in position 10, (2) a glutamic acid residue substituted for the lysine residue in position 32, (3) a glutamic acid residue substituted for the arginine residue in position 36, (4) a glutamic acid residue substituted for the alanine residue in position 34, (5) an asparagine residue substituted for threonine residue in position 106 and (6) an asparagine residue substituted for the valine residue in position 253. In another particular example, the Factor VII variant comprises only these six alterations. More details on these variants are found in WO 200158935 to Maxygen, and U.S. Pat. No. 7,371,543 to Pedersen et al., both of which are incorporated by reference herein in their entireties.

The Factor VII variants described herein can be designed using any functional Factor VII polypeptide as a starting polypeptide. In certain embodiments, the Factor VII polypeptide is a human Factor VII polypeptide. In further embodiments, the Factor VII polypeptide is the human Factor VII polypeptide of SEQ ID NO: 16, or a modified form or allelic variant thereof. Useful starting polypeptides also include modified or variant Factor VII polypeptides comprising an amino acid sequence at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identical to the sequence of wild type human Factor VII (SEQ ID NO: 16) that also possess Factor VII activity. Further, in certain examples, the variant Factor VII polypeptides of the present disclosure include any polypeptide with at least about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identity to the sequence of SEQ ID NO: 16 that possess Factor VII functionality and that also contain one or more of the amino acid alterations discussed herein relative to SEQ ID NO: 16. In another embodiment, the Factor VII polypeptide comprises an amino acid sequence having more than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% homology to SEQ ID NO:16 and has Factor VII activity, and that also has one or more of the amino acid alterations referenced herein.

Factor VII variants as used herein also includes glycosylation variants of wild type Factor VII. For example, a partially desialylated wild type Factor VII variant and compositions thereof can be useful because it has a shorter half-life than wild type Factor VII. Also useful herein are pharmaceutical formulations of partially or completely desialylated wild type Factor VII and use of such polypeptides and formulations in the treatment of the diseases recited herein that benefit from a short-acting polypeptide having Factor VII activity. Partial or complete desialylation can be measured by the ratio of moles of conjugated sialic acid to moles of N-linked glycan in a composition of Factor VII polypeptides as described herein.

Nucleotide sequences encoding the Factor VII variants herein are also useful. In one embodiment, the Factor VII polypeptides are encoded by a nucleotide sequence having at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identity across the full length to the nucleotide sequence of wild type Factor VII (SEQ ID NO: 1) and that encode a functional Factor VII polypeptide. In certain examples, the nucleotide sequence also encodes a polypeptide containing one or more of the amino acid alterations discussed herein relative to SEQ ID NO: 16. In another embodiment, the Factor VII polypeptide is encoded by a nucleotide sequence having more than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% homology to the nucleotide sequence of wild type Factor VII (SEQ ID NO: 1) and that encodes a functional Factor VII polypeptide. In certain examples, the nucleotide sequence also encodes a polypeptide containing one or more of the amino acid alterations discussed herein relative to SEQ ID NO: 16.

The percent identity values are calculated over the entire amino acid or nucleic acid sequence region. A series of programs based on a variety of algorithms are available to the skilled worker for comparing different sequences. In at least one embodiment, the percent identity between two amino acid sequences is determined using the Needleman and Wunsch algorithm (Needleman 1970, J. Mol. Biol. (48):444-453), which has been incorporated into the needle program in the EMBOSS software package (EMBOSS: The European Molecular Biology Open Software Suite, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap extension penalty of 0.5, 1, 2, 3, 4, 5, or 6. Guides for local installation of the EMBOSS package as well as links to WEB-Services can be found at emboss-.sourceforge.net. A non-limiting example of parameters to be used for aligning two amino acid sequences using the needle program are the default parameters, including the EBLOSUM62 scoring matrix, a gap opening penalty of 10, and a gap extension penalty of 0.5. In yet another embodiment, the percent identity between two nucleotide sequences is determined using the needle program in the EMBOSS software package (EMBOSS: The European Molecular Biology Open Software Suite, Rice, P., Longden, I., and Bleasby, A, Trends in Genetics 16(6), 276-277, 2000) using the EDNAFULL scoring matrix with a gap opening penalty of 16, 14, 12, 10, 8, 6, or 4 and a gap extension penalty of 0.5, 1, 2, 3, 4, 5, or 6. A non-limiting example of parameters to be used for aligning two amino acid sequences using the needle program are the default parameters, including the EDNAFULL scoring matrix, a gap opening penalty of 10, and a gap extension penalty of 0.5. The nucleic acid and protein sequences can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using nucleic acid sequences of the present disclosure as query sequence can be performed with the BLASTn, BLASTx, or tBLASTx program using default parameters to obtain either nucleotide sequences (BLASTn, tBLASTx) or amino acid sequences (BLASTx) homologous to sequences encoded by the nucleic acid sequences of the present disclosure. BLAST using protein sequences encoded by the nucleic acid sequences of the present disclosure as query sequence can be performed with the BLASTp or the tBLASTn program using default parameters to obtain either amino acid sequences (BLASTp) or nucleic acid sequences (tBLASTn) homologous to sequences of the present disclosure. To obtain gapped alignments for comparison purposes, Gapped BLAST using default parameters can be utilized as described in Altschul et al., 1997, Nucleic Acids Res. 25(17):3389-3402.

The polynucleotides of the present disclosure either essentially consist of the aforementioned nucleotide sequences or comprise the aforementioned nucleotide sequences. Thus, they can contain further nucleotide sequences as well. In certain embodiments, the polynucleotide can comprise, in addition to an open reading frame, further untranslated sequence at the 3' and/or at the 5' terminus of the coding gene region, for example at least 10, 20, 30, 40, 50, 60, 70, 80, 90, 100, 200, 300, 400, 500, or more nucleotides of the sequence upstream of the 5' terminus of the coding region and/or at least 10, 20, 30, 40, 50, 60, 70, 80, 90, 100, 200, 300, 400, 500, or more nucleotides of the sequence downstream of the 3' terminus of the coding gene region. Furthermore, the polynucleotides can encode fusion proteins wherein one partner of the fusion protein is a polypeptide being encoded by a nucleotide sequence recited above. Such fusion proteins can comprise so called "tags" which may serve as a detectable marker or as an auxiliary measure for purification purposes. Tags for the different purposes are well known in the art and comprise FLAG-tags, 6-histidine-tags, MYC-tags and the like. In one embodiment, the polynucleotide further comprises an expression control sequence operatively linked to the nucleotide sequence.

In certain embodiments, a nucleic acid sequence encoding the Factor VII polypeptide is inserted into a suitable vector. Numerous vectors useful for various purposes are well known in the art and persons skilled in the art would be able to readily select an appropriate vector for their desired application. In certain examples, the vector may be a cloning vector or an expression vector. In other examples, the vector may be a plasmid, a viral vector, a cosmid, or an artificial chromosome. In certain examples, the nucleic acid encoding the Factor VII polypeptide may be placed adjacent to and/or under the control of an appropriate promoter. Numerous promoters useful for various purposes are well known in the art and persons skilled in the art would be able to readily select an appropriate promoter for their desired application. In certain examples, the promoter may be a constitutive promoter, an inducible promoter, or a tissue specific promoter.

In certain embodiments, the Factor VII polypeptides are recombinantly produced in a cell, tissue, or organism. In certain embodiments, such recombinant production is accomplished by transforming or transfecting a host cell with a nucleic acid molecule encoding the variant polypeptide or a vector containing such nucleic acid. Numerous methods of transformation and transfection are well known in the art and persons skilled in the art would be able to readily select an appropriate method for their desired application.

Such recombinant production can also be accomplished using any suitable host cell, tissue, or organism. Suitable cells, tissues, and organisms are well known in the art and persons skilled in the art would be able to readily select an appropriate host for their desired application. In some embodiments, the host cell is mammalian. Examples of suitable mammalian cell lines are the COS-1 (ATCC CRL 1650), baby hamster kidney (BHK), HEK293 (ATCC CRL 1573; Graham et al., J. Gen. Virol. 36:59-72, 1977), HEK293T (ATCC CRL 11268; DSM ACC 2494), and HEK293F (Invitrogen R79007) cell lines. A useful BHK cell line is the tk$^{31}$ ts13 BHK cell line (Waechter and Baserga, Proc. Natl. Acad. Sci. USA 79:1106-1110, 1982, incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk$^-$ ts13 BHK cell line is also available from the ATCC under accession number CRL 1632. In addition, a number of other cell lines can be used within the present disclosure, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61), CHO K1 (ATCC CCI61), DUKX cells (Urlaub and Chasin, Proc. Natl. Acad. Sci. USA 77:4216-4220, 1980) and CHO-DG44 cells (Urlaub et al. Cell 33: 405-412, 1983).

Compositions of Factor VII polypeptides are useful in which the Factor VII polypeptides are defined as herein and the ratio of moles of conjugated sialic acid per mole of N-linked glycan in the composition is less than 0.05, less than 0.1, less than 1.0, less than 2.0, less than 3.0, less than 4.0, less than 5.0 or less than 6.0, or compositions wherein the ratio of moles of conjugated sialic acid per mole of N-linked glycan is within a range selected from the group consisting of (1) from 0 to 8; (2) from 0 to 7; (3) from 0 to 6; (4) from 0 to 5; (5) from 0 to 4; (6) from 0 to 3; (7) from 0 to 2; (8) from 0 to 1 and (9) from 0 to 0.5, or ratios of from 1 to 8, 1 to 7, 1 to 6, 1 to 5, 1 to 4, 1 to 3, 1 to 2, 2 to 8, 2 to 7, 2 to 6, 2 to 5, 2 to 4, 2 to 3, 3 to 8, 3 to 7, 3 to 6, 3 to 5, 3 to 4, 4 to 8, 4 to 7, 4 to 6, 4 to 5, and 0.1 to 1. The ratio is a measurement of the moles of sialic acid bound to a glycoprotein relative to the number of glycans on the glycoprotein. The number of glycans refers to the number of sugar moieties attached to an N-linked glycan in the glycoprotein, where one N-linked glycosylation site can support only one glycan as defined herein for purposes of this ratio. The ratio is determined using a sialic acid fluorescence labeling kit such as that sold by Takara Bio Inc. (cat. #4400). Such a sialic acid fluorescence labeling kit includes a step for the release of sialic acid from the bound glycoprotein, such as by partial acid hydrolysis or by use of sialidase, such as *Arthrobacter ureafaciens* sialidase. The free sialic acids are then labeled with a fluorophore such as 1,2-diamino-4, 5-methyleneoxybenzene ("DMB"). The labeled sialic acids are then quantitatively measured using HPLC and comparing peak heights to a calibration curve. Thus, the ratio measured is a ratio of moles of sialic acid per mole of glycan released from all the Factor VII polypeptides of the composition.

In one series of embodiments, the compositions of Factor VII polypeptides or the isolated polypeptides themselves have a half-life as measured in human or mammalian plasma, for example murine or rat plasma, of less than 2 hours, less than 1.5 hours, less than 1 hour, less than 0.75 hour, less than 0.5 hour, less than 0.25 hour, less than 0.1 hour, or so short that it cannot reasonably be measured.

As used herein, Factor VII activity is a biological activity that may be quantified by measuring the ability of a preparation to promote blood clotting using Factor VII-deficient plasma and thromboplastin, as is well known in the art. In certain examples, a Factor VII polypeptide having Factor VII activity shows at least 25%, at least 40%, at least 50%, at least 60%, at least 70%, at least 80%, or at least 90% of the activity of wild type Factor VII as measured under the same conditions.

Pharmaceutical formulations of the Factor VII polypeptides and compositions thereof comprising the Factor VII polypeptide and a pharmaceutically acceptable excipient or carrier are also useful. In certain examples, the pharmaceutical formulations are for parenteral administration, such as by intravenous, subcutaneous or intramuscular administration, and dosing may be as a single bolus dose, intermittent dosing, or as a continuous intravenous infusion. Topical formulations are also useful. One embodiment comprises a pharmaceutical formulation comprising an isolated Factor VII polypeptide as described herein, or comprising a composition of Factor VII polypeptides as described herein, in a lyophilized preparation that is reconstituted at the time of use. Alternatively, the pharmaceutical formulation can be a stable liquid ready-to-use formulation not requiring reconstitution. The pharmaceutical formulation can be a lyophilized powder in single-use vials of 1, 2, 5, or 8 mg of Factor VII polypeptide. After reconstitution with a specified volume of liquid, such as sterile water containing histidine, the final solution can contain any suitable amount of Factor VII polypeptide that produces a therapeutic effect, such as, without limitation, 1 mg/mL (1000 micrograms/mL), 2 mg/mL, 3 mg/mL, 4 mg/mL, 5 mg/mL, 1-2 mg/mL, 1-3 mg/mL, 1-5 mg/mL, 1-10 mg/mL, 0.5-1 mg/mL, or 0.5-2 mg/mL of Factor VII polypeptide. Proper dosage for administration to a patient can be readily determined by persons skilled in the art based upon, for example, the weight of the patient, the type of bleeding disorder or episode being treated, and the activity of the particular Factor VII polypeptide being employed. In certain examples, dosing can be in the range of 70-110 micrograms/kg, 70-90 micrograms/kg, or 80-100 micrograms/kg and can be 90 micrograms/kg. The lyophilized powder may be reconstituted with an aqueous carrier, such as water, buffered water, 0.4% saline, 0.3% glycine, etc. Actual methods for preparing parenterally administrable compositions will be known or apparent to those skilled in the art and are described in more detail in, for example, Remington's Pharmaceutical Sciences, 18th ed., Mack Publishing Company, Easton, Pa. (1990). Topical application, such as can be advisable in the case of trauma, can be carried out by means of a spray, perfusion, catheters, stent, vascular graft or stent, ointment, or other preparation known in the art. In certain examples, topical administration can be by way of a sold or semi-solid matrix, such as a surgical sponge or collagen matrix, which has been treated with, infused with, coated with, or soaked in a composition comprising the Factor VII variant. Methods of preparing such matrices are well known in the art (see, e.g., Thrombosis/Hemostasis 12:445, 2006) and the skilled artisan would be able to readily determine an appropriate dose and method of application of the composition onto the given matrix.

In one embodiment, the present disclosure relates to kits comprising the Factor VII polypeptide. In certain examples, the kit contains a vial containing ready-to-use liquid containing the Factor VII polypeptide in a suitable pharmaceutical composition. In other examples, the kit contains a vial containing lyophilized Factor VII polypeptide, or a lyophilized formulation comprising the polypeptide, and also a diluent for reconstitution. In other examples, the kit contains a topical formulation of the Factor VII polypeptide, for example, an ointment, spray, or liquid, and a matrix such as a sponge or other medical matrix to which the topical formulation may be applied before administration to the patient.

Compositions of the Factor VII polypeptides described herein are also useful. Factor VII exists in mixture with its natural degradation products. Accordingly, a composition of Factor VII polypeptides includes polypeptides having one of the full amino acid sequences as recited herein and degradation products having partial amino acid sequences of those described herein. Furthermore, because Factor VII is a glycoprotein, compositions of Factor VII can be expected to contain a heterogeneous mixture of Factor VII polypeptides wherein each glycoprotein in the composition does not have exactly the same glycosylation as the others. Reference to compositions of Factor VII polypeptides or isolated Factor VII polypeptides is meant to encompass mixtures of such polypeptides wherein the individual polypeptides have different glycosylation, and thus the terms "composition" or "isolated Factor VII polypeptide" encompass a heterogeneity of the glycosylation patterns within the polypeptides.

The Factor VII polypeptides and compositions described herein are useful for the treatment of blood clotting disorders, and those disorders that benefit from blood coagulation, and particularly for coagulation with a drug having a shorter half-life than wild type Factor VII. Accordingly, the Factor VII polypeptides and compositions herein are useful for penetrating traumatic injury; blunt traumatic injury; bleeding in elective surgery; bleeding in cardiac surgery; bleeding in spinal surgery; orthopedic surgery; neurosurgery; oncology surgery; post-partum surgery; menorrhagia; bleeding in stem cell transplantation; bleeding in liver transplantation; gastrointestinal bleeding; active variceal bleeding in cirrhosis; non variceal bleeding in cirrhosis; diffuse alveolar hemorrhage; aortic aneurysm; intracerebral hemorrhage; traumatic brain injury; brain contusion; reversal of warfarin; reversal of heparin; reversal of anticoagulants; reversal of anti-thrombotics; Factor VII deficiency; burns; prophylaxis in hemophilia patients with inhibitors; partial hepatectomy for non-cirrhotic and cirrhotic patients; acquired hemophilia; idiopathic thrombocytopenic purpura; Glanzmann's Thrombasthenia; Glanzmann's Thrombasthenia refractory to platelet transfusion and Bernard-Soulier Syndrome.

Also disclosed herein is a useful assay for measuring the half-life of coagulation factors such as Factor VII. There is a method of determining the half-life of a coagulation factor comprising incubating viable rat hepatocyte cells with a blood coagulation factor, removing a sample at testing time point 1, separating supernatant from cells in the sample and quantifying the activity or amount of the blood coagulation factor in the supernatant in the sample, wherein the activity or amount of the blood coagulation factor is determined using a double-antibody sandwich ELISA assay. The method may be repeated at different time points to develop a plot of activity or amount of blood clotting factor over time.

EXAMPLES

Methods to Obtain Desialylated Factor VII Polypeptides

Numerous methods were employed to generate desialylated Factor VII polypeptides (both wild-type and variant), including enzymatic desialylation of the polypeptide, production of the Factor VII polypeptide in a sialylation-deficient cell line, and co-expression of Factor VII and a sialidase in a recombinant cell.

Generation of Sialic Acid Deficient Cell Line

Endogenous sialic acid is synthesized in mammalian cells involving a complex pathway consisting of 32 enzymes (Wickramasinghe and Medrano 2011). The biosynthesis of sialic acid starts in cytosol converting UDP-N-acetylglucosamine (UDP-GlcNAc) to Neu5Ac involving several enzymes, such as UDP-N-acetylglucosamine-2-epimerase/Nacetylmannosamine kinase (GNE), sialic acid 9-phosphate synthase (NANS), and sialic acid 9-phosphate phosphatase (NANP). Neu5Ac in cytosol is imported into the nucleus through nuclear pores and converted into CMP-Neu5Ac by an enzyme called CMP-Sia synthase (CMAS). Synthesized CMP-Neu5Ac is again transported back into the cytosol via nuclear pores for further modification and conjugation in the Golgi apparatus. Conversion of Neu5Ac into Neu5Gc in cytosol is catalyzed by the enzyme CMP-NeuAc-hydroxylase (CMAH). Then, CMP-Neu5Ac and CMP-Neu5Gc are transported into the Golgi compartment via a hydrophobic type 3 membrane transporter, CMP-sialic acid transporter (SLC35A1), located in the membrane of the median trans-Golgi. CMP-sialic acid transporter is a key element in the cellular sialylation pathway (Hirschberg, et al. 1998). A homozygous mutation of this gene causes post-natal lethality in the mouse (MGI 4.32, Homologene). In humans mutations in SLC35A1 are associated with the reduction or complete loss of sialyl conjugates. Some insertion and deletion mutations in SLC35A1 are associated with congenital disorders of glycosylation in humans leading to defects in nervous system development, coagulation, and immune deficiency (Martinez-Duncker, et al., 2005). Once CMP-Neu5Ac/CMP-Neu5Gc is transported into the Golgi apparatus they are conjugated with carbohydrates, glycoproteins, and glycolipids by enzymes in the sialyltransferase (ST) family with 20 members.

CMP-sialic acid transporter (SLC35A1) is the key molecule supporting sialic acid conjugation in the Golgi apparatus, and mutations to this transporter protein lead to synthesis of proteins lacking proper sialylation. To produce desialylated Factor VII, a Factor VII production cell line with CMP-sialic acid transporter gene knockout is produced. Alternatively, desialylation could be achieved by expression of the Factor VII variant in a cell line that produces protein therapeutics with a very low level or no sialylation on the therapeutic molecules. This technology could be used to produce therapeutic proteins with short T1/2 in patients.

Lec2 cell with Chinese hamster ovary (CHO) origin was identified with the property of producing approximately 10-fold less sialic acid in glycoproteins and glycolipids than the respective wild-type cells (Stanley and Siminovitch, 1977, Stanley, 1980 and 1983). A later study showed that Lec2 mutants were unable to translocate CMP-sialic acid across membranes of Golgi vesicles in an in vitro assay, while translocation of other nucleotide derivatives was comparatively normal in mutant cells (Deutscher, et al., 1984). By using expression cloning, the gene encoding the CMP-sialic acid transporter from Lec2 cells was reported (Eckhardt et al., 1996). Further investigation indicated that the deletion of nucleotides 575-751 in the CMP-sialic acid transporter gene was responsible for the Lec2 phenotype (Eckhardt, et al., 1998). Other mutations in the CMP-sialic acid transporter gene, such as in the case of 1E3, 6B2, 8G8, and 9D3 cells, also lead to the Lec2 phenotype (Eckhardt, et al., 1998).

Experiment 1

This experiment is designed to determine whether the mutation in the gene of CMP-sialic acid transporter, such as in the case of Lec2 cells, results in expressed recombinant protein (e.g., Factor VII) deficient in sialylation in comparison with the same protein expressed from normal CHO cells.

(1) Testing the expression of recombinant protein, such as Factor VII, from Lec2 cells. Expression vectors containing a Factor VII variant gene (e.g., pMB117 and pMB121) are transfected into Lec2 cells and normal CHO cells under normal transfection conditions. Expression levels of Factor VII from cell culture of these cells is monitored by a Factor VII activity assay. The culture of transfected cells is scaled-up and the culture conditioned media is harvested for the purification of Factor VII.

(2) Testing the sialic acid content of purified Factor VII expressed from Lec2 cells in comparison to the same protein expressed from normal CHO cells. Purification of Factor VII from these conditioned media is conducted following the normal Factor VII purification methods. The purified Factor VII from either Lec2 cells or normal CHO cells is analyzed for sialic acid content of the purified Factor VII. The biological activity and pharmacokinetic (PK) parameters are analyzed as described herein.

Experiment 2

In order to produce a manufacturing cell line to express a Factor VII variant with no sialic acid on the expressed recombinant proteins, gene deletion methods are used targeting the CMP-sialic acid transporter gene to modify a cell line that expresses Factor VII (e.g., a CHO cell line). In order to completely inhibit the sialylation in the cell, other targets, such as UDP-N-acetylglucosamine-2-epimeraseNacetylmannosamine kinase (GNE), sialic acid 9-phosphate synthase (NANS), sialic acid 9-phosphate phosphatase (NANP), and CMP-Sia synthase (CMAS) as listed above in the introduction, optionally can also be deleted to enhance the inhibition of the CMP-Neu5Ac biosynthesis which provides the substrate for the CMP-sialic acid transporter.

Two gene deletion technologies, TALE nucleases (TALENs) from Life Technologies and ZFP Nucleases (ZFNs) from Sangamo BioSciences/Sigma-Aldrich, can be used for conducting the knockout of CMP-sialic acid transporter gene, or the knockout of multiple genes in the sialic acid synthesis pathway.

The Factor VII expression cell line with CMP-sialic acid transporter gene knockout is evaluated to confirm the deletion of CMP-sialic acid transporter gene. The confirmed cell line is cultured to produce Factor VII. Factor VII from the CMP-sialic acid transporter gene-deleted cell line is purified and evaluated as described herein and compared to the Factor VII from the parental Factor VII expression cell line for sialic acid content on the molecule.

Production of Desialylated Factor VII by Coexpression of Factor VII and a Bacterial Sialidase To generate a desialylated form of FVII, we co-expressed FVII along with a bacterial sialidase variant derived from the *Arthrobacter ureafaciens* sialidase (AU sialidase) (N-acetylneuraminate glycohydrolase, EC 3.2.1.18). CHO cells stably expression FVII (e.g., SEQ ID NO 16 with P10Q, K32E, A34E and R36E mutations) were further transfected with AU sialidase using a pJ608 expression vector. The expressed protein has a growth hormone signal sequence at the N-terminus to promote secretion of the protein. Stable clones were selected that produced AU sialidase as detected by a chromogenic assay for sialidase in the medium. We also showed that the cells continued to express high levels of FVII protein, which was detected by ELISA assay, SDS PAGE and Western blotting, using FVII specific antibodies as the probe. Using a lectin blotting assay, we were not able to detect sialic acid on FVII protein in the condition media, using purified FVII. In contrast, similar levels of purified FVII derived from cells not transfected with sialidase showed a strong lectin binding signal. Taken together, our data show that the AU sialidase was expressed in the CHO cell medium at levels sufficient to efficiently desialylate FVII that was co-expressed by the cells.

Enzymatic Preparation of Desialylated Factor VII Using a Soluble Sialidase Treatment The following starting materials were utilized in this experimental trial:

Factor VII: 20 mg Wild Type Factor VIIa, concentration about 1 mg/ml Sialidase: 20 ug, 0.25 mg/ml, 50000 U/ml, P0720 L, purchased from New England BioLabs Buffer solution A: 25 mM histidine, 50 mM NaCl, pH 6.4

Buffer solution B: 25 mM histidine, 1M NaCl, pH 6.4

FVIIa formulation buffer: 2.3 mg/ml sodium chloride, 1.5 mg/ml calcium chloride dehydrate, 1.3 mg/ml glycylglycine, 0.1 mg/ml polysorbate 80, 25 mg/ml mannitol, 10 mg/ml sucrose, 0.5 mg/ml methionine, 1.6 mg/ml histidine, pH 6.0

Purification column: 5 ml HiTrap Q Sepharose HP column

Using these materials, the following procedure was carried out:

1. To 20 mgs of FVIIa (about 1 mg/ml), add 20 ug of sialidase (0.25 mg/ml, 1:1000 mass ratio) of sialidase
2. Incubate the reaction at room temperature overnight (about 19 hr) before chromatographically purifying desialylated FVIIa as described below.
3. Purify desialylated FVIIa on a 5 ml HiTrapQ Sepharose HP column as follows:
   a) Equilibrate the Q-Sepharose column with 5 CV of buffer A (25 mM histidine, 50 mM NaCl, pH 6.4).
   b) Before applying to the column, dilute the FVIIa and sialidase reaction with 200 ml of buffer A and adjust pH to 6.4.
   c) Load at a flow rate of 2.5 ml/min using an AKTA Explorer system while monitoring A280. Collect Flow through fraction.
   d) After loading is completed, wash the column with 10 CV of Buffer A.
   e) Elute the column with 20 CV of 0-50% buffer B (25 mM histidine, 1M NaCl, pH 6.4) in 40 min. Collect peak fractions (Desialylated NovoSeven)
   f) Dialyze the peak fractions vs. FVIIa formulation buffer at 4° C. overnight
   g) Freeze the sample at −80° C. in aliquots.

The product was shown to be highly pure by SDS-PAGE, aSEC, and active in biological assays for FVIIa. Assays for sialic acid content showed no residual sialic acid and LC-MS analysis of the heavy chain showed not significant alteration of glycan structure other than removal of sialic acid.

Enzymatic Preparation of Desialylated Factor VII Using Neuraminidase Agarose Beads Recombinant wild type Factor VII as used herein is NovoSeven® obtained from Novo Nordisk and referred to herein as "F7." Other starting materials are V1 and V2 as described supra.

Frozen starting material was quick-thawed in a 37° C. water bath and pooled. The protein was concentrated 2.5-fold by centrifugation; concentrate was gently mixed by pipetting to minimize any super-concentration (aggregation) at the protein-filter interface.

The V2 was buffer-exchanged from its V2 formulation buffer (containing histidine, $CaCl_2$, trehalose, methionine, and trace levels of Tween®-20, at a pH 6.4-6.6) into MES buffer (containing 10 mM IVIES, 10 mM $CaCl_2$, 50 mM NaCl, pH 6.0, sterile-filtered). This was achieved one of three ways. In the first option, V2 was buffer-exchanged with NAP-10 gravity flow columns (GE, 17-0854-01), which were pre-washed 3-5 times with 3 column-volumes each of IVIES buffer. The V2 was then loaded onto the column and eluted with 1.5 times the load volume of IVIES buffer. In the second option, V2 was buffer-exchanged by overnight dialysis in IVIES buffer. Dialysis cassettes were pre-soaked in MES buffer and the V2 was loaded by syringe into the 3.500 MWCO slide-a-lyzer cassettes (Thermo Scientific, 66130), overnight at 4° C. in 10 L pitchers with sterile-filtered IVIES buffer. In the third option, V2 was buffer-exchanged into MES buffer through a Sephadex G-25 (Sigma, G-25-80) gel-filtration column, and equilibrated with MES buffer.

The buffer-exchanged V2 was desialylated with neuraminidase-agarose (Sigma N5254). The agarose bead product is provided in a 50% slurry mixture, stored in ammonium sulfate buffer; beads were pre-washed 3-5 times in MES buffer; the bead/buffer mixture was separated by centrifugation at 1000rcf for 3 min at 4° C., and the supernatant liquid was pipetted off and discarded. To the washed beads, the buffer-exchanged V2 was added and gently mixed by rotation at room temperature for 16 to 22 hours. 2.08 mL of packed beads per mg of protein were used for desialylation; for a larger scale preparation, this was reduced 1:10, to 0.208 mL of beads per mg of protein. Afterward, the desialylated V2 was recovered by centrifugation and pipetted off. The beads were washed once gently for 5 minutes by rotation in 1:1 by volume of fresh IVIES buffer; the wash mixture was centrifuged as before and the supernatant was pooled with the V2. The beads were finally removed either by sterile-filtration through a 0.2 micron syringe filter or by vacuum filtration through at 0.45 micron filter.

Several rounds of endotoxin removal were performed with EndoTrap® HD resin (Hyglos). The resin was washed 3-5 times in MES buffer and wash buffer was discarded. In two batches, 1-3 mL of washed resin was gently mixed with the desialylated V2 overnight at room temperature. The resin was removed by centrifugation and then filtered through syringe or vacuum filter.

The desialylated V2 was concentrated 4.75-fold to 2.1 mg/mL by centrifugation in Ultracels for 10-minute cycles; the concentrates were gently mixed by pipetting to reduce any aggregation at the protein-filter interface.

The desialyated V2 was further separated from higher-molecular weight species (and aggregated endotoxin) with HiLoad 26/60 Superdex 200 size exclusion column. The column and the AKTA purifier system was pre-sanitized with 0.1N NaOH+20% EtOH. The system was pH-neutralized, rinsed with water, and equilibrated with reconstituted and pooled V2 formulation buffer. Several batches of concentrate were manually injected into a 12 mL sample loop and loaded onto size exclusion column at a flow rate of 3 mL/min; the eluate was recovered and fractionated with a Frac-900 into polystyrene tubes (17×100 mm, Fisherbrand, 14-956-6D). Early, high-molecular weight peaks were excluded and the desired V2 fractions were pooled and tested for endotoxin levels and concentration using Charles River EndoSafe PTS and NanoDrop ND-1000. V2 buffer was used to elute the desialylated V2.

Five batches of size-exclusion were performed and the collected eluates were pooled into one batch which was concentrated to 1.0 mg/mL in Ultracels. The final preparation was sterile-filtered through 0.2 micron syringe filters and tested for endotoxin and concentration. 1 mL aliquots were pipetted into labeled 2 mL tubes (Sarstedt, 72.694.006), flash-frozen in an ethanol/dry-ice batch, and stored in a labeled box at −80° C. until use.

Characterization—Protein Analytics and In Vitro Assay

The final prep material as well as the non-treated starting material were characterized by protein gel analysis with 4-12% Bis-Tris NuPAGE (Novex NP0335BOX) in MES running buffer and by analytical size exclusion (TSK3000 column; running buffer: 200 mM $KH_2PO_4$, 150 mM KCl, pH 6.8, flow rate: 0.15 ml/min, fluorescence detection). Small test samples were analyzed by LC-MS for sialic acid content on the Factor VII heavy chain as well as DMB-labeled sialic acid quantification of total protein using the Takara Bio Inc. kit discussed herein. The activity was tested by phospholipid-dependent Factor X activation and thrombin generation assays.

Sialic Acid Content Analysis

An LC-MS method was used to identify the sialic acid on the N-glycan of the heavy chain of Factor VII for the non-treated control and desialylated Factor VII. 10 µg of protein was reduced with 10 mM DTT mix at 37° C. for 30 min then analyzed on the Agilent 1200 Capillary LC System: Column: PLRP-S 8 µm 4000A, 0.3×150 mm, 75° C. Buffer systems: A: Water with 0.2% Formic Acid+0.01% TFA; B: ACN with 0.2% Formic Acid+0.01% TFA. Gradient: 50 µL/min, 10% B in 2 min, to 90% B in 25 min, 90% B wash 5 min, 10% B equilibration for 5 min.

Agilent 6520 Q-TOF system: DualEsi source, gas temp: 350° C., drying gas: 7 psi, nebulizer: 10 psi, scan range: 500-3000 amu, 1 spectra/s. Reference ions: 1221.990637 and 2421.91399 amu, 50 ppm window, Min 1000 counts. The results are reported in FIG. 7.

Sialic Acid Quantification Using DMB Labeling Kit

Sialic Acid Fluorescence Labeling Kit (Takara Bio Inc., Cat #4400) is for quantitative and highly sensitive analysis of sialoglycoconjugates. This HPLC-based sialic acid fluorescence labeling technique using 1,2-diamino-4,5-methyleneoxybenzene (DMB) is a simple and highly sensitive quantitative method. In this method, free sialic acids are analyzed by reverse phase HPLC (GlycosepR, from Glyko, #1-4727) after labeling by DMB.

Conclusion

The V2 heavy chain has two N-glycosylation sites. The N-glycans are fucosylated, heavily sialylated bi,tri-and tetra-structures. No terminal sialic acids are found on the desialylated sample, which suggests the sample is fully desialylated and that >99.9% of the sialic acid on the Factor VII N-glycan has been removed.

Half-Life Assay Using Rat Hepatocytes

Preparation of Hepatocytes

Cryopreserved primary rat hepatocytes were obtained from CellzDirect (Invitrogen). Each vial containing approximately 5 million cells was thawed and the cells were added to 10 ml of Thawing Medium, followed by centrifugation at 60 g for 3 minutes. The cells were resuspended in Incubation Medium+0.25% BSA (about 4 ml) and the cells were counted using a hemacytometer. Viable cells were counted after staining with Trypan blue to identify dead cells. Cell viability was 80-82%. Cells were used in the clearance assay immediately after counting.

Thawing Medium: Invitrogen CM3000 Thawing/Plating Supplement Pack added to 500 ml Williams E Medium. Incubation Medium: Invitrogen CM4000 Cell Maintenance Supplement Pack added to 500 ml Williams E Medium.

In Vitro Hepatocyte Clearance Assay

Primary rat hepatocytes, 1 million viable cells per ml, were incubated with 25 ng/ml of various Factor VII variants in CellzDirect Incubation Medium+0.25% BSA, in Eppendorf tubes with gentle end over end mixing at 37° C. in a starting volume of 1.2 ml. At each of the indicated time points, 0.25 ml of the mixture was removed and immediately centrifuged to pellet the cells (1000 rpm, 3 minutes in Eppendorf centrifuge). 0.18 ml of the clarified supernatant was removed, quick frozen and stored overnight at −80° C. On the next day, Factor VII in the supernatants was quantified using an ELISA assay in which the corresponding purified mutant protein was used as the standard. No-cell control supernatants in which Factor VII variants were incubated for 2 hours at 37° C. in medium alone were used as the zero time point values. Each incubation was done in triplicate. Intrinsic clearance values were calculated based on the method of Lu et al. (Lu ref.) using the equation CLint=0.693/in vitro $T_{1/2}$, normalized for the incubation volume and the number of cells. In vitro half-life ($T_{1/2}$) was calculated using the program WinNonLin (Pharsight Corporation, Sunnyvale, Calif.). Supernatants from hepatocyte incubations were assayed using a double-antibody sandwich ELISA format. 0.1 ml per well of anti-Factor VII monoclonal antibody (1.0 µg/ml, in PBS) was added to Greiner Microlon 655061 96-well plates. After incubation overnight at 4° C., plates were blocked with 0.2 ml per well of 1% casein blocking buffer (50 mM TrisHCl, 100 mM NaCl, 0.05% Tween 20 pH7.2) for 1.5 hours at 37° C. Plates were washed four times with 0.3 ml per well PBS+0.05% Tween 20 (using a BioTek ELx405 plate washer), and then relevant Factor VII standard and unknown samples were added to the plates. 0.18 ml of each hepatocyte supernatant was diluted two-fold by adding 0.18 ml of Dilution Buffer (50 mM TrisHCl, 100 mM NaCl, 0.1% casein, 0.05% Tween 20 pH7.2). 0.10 ml of each diluted supernatant was added in triplicate to the ELISA plate. Standards were made from the corresponding purified Factor VII variant diluted in Dilution Buffer. Two-fold serial dilutions of the standard were made in Dilution Buffer to yield dilutions in the range of 50 to 0.8 ng/ml final concentration. Factor VII standards and samples (0.1 ml per well) were incubated 2 hours at room temperature (21° C.). Plates were washed four times as described above, and then biotinylated detection antibody, 1 µg/ml in Dilution Buffer (50 mM TrisHCl, 100 mM NaCl, 0.1% casein, 0.05% Tween 20 pH7.2) was added (0.1 ml per well) followed by incubation for 1.5 hours at room temperature. Plates were washed four times as described above, and then Streptavidin-horseradish peroxidase, diluted 1/1000 in Dilution Buffer was added (0.1 ml per well) followed by incubation for 1 hour at room temperature. Plates were washed again and Ultra-TMB was added, 0.1 ml per well. After incubation for 10 to 15 minutes at room temperature, the reaction was stopped with the addition of 0.05 ml per well 2 M $H_2SO_4$. Absorbance was read at 450 nm using a Molecular Devices Spectramax M2 plate reader. Data analysis was performed using Softmax Pro 5.4 (Molecular Devices).

Cryopreserved rat hepatocytes, Thawing Medium, and Incubation Medium (CellzDirect), were from Invitrogen/Life Technologies (Grand Island, N.Y.). 1-Step Ultra-TMB (One Step) substrate, catalog no. 34028, was from Thermo Scientific (Rockford, Ill.) Streptavidin-horseradish peroxidase (SA-HRP), catalog no. DY998, was from R&D Systems, Minneapolis, Minn. Phosphate-buffered saline, pH 7.2 was from Invitrogen (Carlsbad, Calif.). Sprague-Dawley Rat plasma (5% sodium citrate anticoagulant) was from Bioreclamation (Westbury, N.Y.). Greiner Microlon plates (cat. no. 655061) were obtained through Fisher Scientific (Pittsburgh, Pa.).

Methods to Obtain Deglycosylated Variants: Molecular Variants

Wild type Factor VIIa has two N-glycans (N322 and N145), and V1 and V2 each have 4 N-glycans (N106, N145, N253, N322). The additional 2 N-glycans (N106, N253) found in V1 and V2 were originally designed to increase half-life. For this work, these sites are removed by reverting them back to the endogenous amino acid sequence of wild type Factor VII (T106, V253). The remaining 2 endogenous N-glycan sites (N145 and N322) were then removed at the DNA level by engineering in N→Q mutations at these sites. (FIG. 6)

Wild type Factor VII was cloned into pmCMV to make pMB113. Inserts containing a single N to Q mutation at positions aa145 or 322, as well as the double mutant (aa 145 and 322) were synthesized and cloned into pMB113 using the XbaI and PmlI site resulting in clones pMB114-116. Inserts encoding the Gla domains of V1 and V2 were then cloned into pMB113-116 using AscI and AfeI and resulted in constructs pMB117-120 (V1-based variants) and pMB121-124 (V2-based variants). All constructs were sequence verified (McLab). Mammalian cells (CHO derived cell line) were transiently transfected via electroporation with each construct in a 6 well format. 4 days post transfection, supernatant was collected and assayed by Western Blot for expression, followed by a hFVII ELISA (AssayPro) and FVII activity assay. A subset of variants was then single cell cloned. The V2 2-Nglycan variant referred to as pMB121 was purified and activated for further analysis.

Method for Purification/Activation of FVIIa from 10 L WAVE Expression

Summary of Method

Purification and activation of FVII from diafiltered concentrated conditioned media was accomplished using a multi-step process taking place over several days. The media is first thawed and centrifuged to remove any aggregate that may have formed during freeze/thaw. A psuedoaffinity capture step employing an anion exchange column (Q-Sepharose) eluted with $CaCl_2$ is used to further concentrate the FVII protein and to change buffer. Next, a hydroxyapatite column is used to further purify the FVII protein. A smaller Q-Sepharose column is then used to further purify FVII before it is activated for 24 hours in solution at pH 7.8-8.2. The activation reaction is stopped by lowering the pH to 4.0. The FVIIa is finally dialyzed into Formulation Buffer (pH 6.5) and stored frozen.

The final purified protein is characterized by SDS-PAGE, aSEC, ELISA, glycoanalysis, endotoxin, and FVIIa activity assay.

FVII ELISA

Zymutest FVII enzyme-linked immunoassay (Aniara, West Chester, Ohio). The ELISA is a two-site immunoassay with a rabbit anti-FVII polyclonal antibody bound to the wells of a 96-well microplate. Sample is introduced followed by a rabbit anti-FVII polyclonal antibody coupled to horse radish peroxidase (HRP). The assays were performed following the manufacturer's instructions. Briefly, samples and calibrator were diluted in assay buffer in a 96-well round bottom polypropylene dilution plate. 50 μL aliquots of diluted sample were transferred to the provided rabbit anti-FVII coated plate and incubated for 15 minutes at room temperature. 200 μL HRP coupled rabbit anti-FVII was added and incubated for 1 hour at room temperature. The plate was washed 5 times with 300 μL of the provided wash buffer. TMB was added at 200 μL/well and incubated for approximately 5 minutes at room temperature. The reaction was stopped by introducing 50 μL 0.45 M sulfuric acid. Absorbance was read at 450 nm. Factor VII levels were derived by comparing sample values to a V2 calibration curve generated using a 4-parameter curve fit.

Factor VII Chromogenic Assay

Biophen FVII chromogenic assay (Aniara, West Chester, Ohio) was used. The chromogenic assay principle involves formation of an enzyme complex consisting of Factor VII from the sample and rabbit thromboplastin (tissue factor) supplied by the manufacturer. FX, added in excess, is activated to FXa, which in turn cleaves a FXa specific chromogenic substrate (SXa-11) generating pNA. The amount of pNA released is directly proportional to the FXa activity. The assay was performed following the manufacturer's instructions. Briefly, samples and calibrator were diluted in Tris-BSA assay buffer in a 96-well round bottom polypropylene dilution plate (Fisher Scientific). Kit reagents, R1, R2, and R3 and a 96 well flat bottom polystyrene assay plate (Costar) were warmed to 37° C. prior to use. 30 μL of sample and calibrator were transferred from dilution plate to assay plate followed by 30 μL of reagent R2 then 60 μL of reagent R1. The assay plate was mixed and incubated for 7 minutes at 37° C. in a jitterbug plate shaker (Boekel Scientific). 60 μL of R3 was added and the rate of change in absorbance (change in OD at 405 nm/min) was measured at 37° C. using a SpectraMax Plus microplate reader (Molecular Devices). Factor VII levels were derived by comparing sample values to a V2 calibration curve generated using a 4-parameter curve fit.

Phospholipid-Dependent Thrombin Generation Assay

Compared to wild-type FVIIa, the modification of Gla-domain (P10Q/K32E) increases potency in FX activation, thrombin generation, and whole blood clotting in the presence of anionic phospholipids or activated platelets as a result of additional γ-carboxylation. PL-dependent TGA was designed to measure rFVIIa activity in the presence of anionic phospholipids and performed using thrombin calibrator and substrate reagent, FluCa-kit, from Thrombinoscope, BV. Phospholipid (PL) vesicles composed of 20% phosphatidylserine (PS), 40% phosphatidylethanolamine (PE), and 40% phosphatidylcholine (PC) were from Avanti Polar Lipids and prepared by sonication in 100 mM NaCl, 50 mM Tris-HCl (pH 7.2) for 10 minutes.

Twenty μL of PL-vesicles (500 μM) or thrombin calibrators were dispensed into 96 well plates. Varying concentrations of rFVIIa were diluted into human HemA plasma, added in triplicate to the PL mixture, and equilibrated to 37° C. for 10 min. Thrombin generation reactions were initiated by adding FluCa solution and the reactions were continuously monitored for 60 minutes following the Calibrated Automated Thrombography (CAT) method outlined by Thrombinoscope$^{BV}$. Data were acquired and analyzed using Thrombinoscope$^{BV}$ (3.4.0) software, which corrected for $\alpha_2$-macroglobulin activity using a thrombin calibrator. The analysis parameter 'peak height' represented the maximum level of thrombin generated, 'endogenous thrombin potential' (ETP) corresponded to the total amount of thrombin generated. Thrombin generation parameters were analyzed with 4-parameter non-linear curve fitting method using Prism 4.0 (GraphPad Inc).

Phospholipid Dependent FX Activation Assay

The ability of FVIIa to activate FX in the presence of phospholipid vesicles without tissue factor was measured using a PL dependent FX activation assay. Factor VIIa or FVIIa variants are incubated with FX in the presence of phospholipid vesicles. Activation of FX is measured by addition of S-2765, a chromogenic substrate for FXa. Briefly, calibrator and samples are diluted in a polypropylene round bottom plate in Tris-HCl buffer. 30 μL of 4 μg/mL FX (Haematologic Technologies Inc.) was added to all wells of a 96-well flat bottom polystyrene plate followed by 30 μL of phospholipid vesicles consisting of phosphatidylserine, phosphatidlycholine, and phosphatidylethanolamine at a wt. % ratio of 20:40:40. 30 μL of diluted sample and calibrator were transferred to the FX/phospholipid mixture. The plate was sealed, mixed gently, and incubated for 20-23 hours at 37° C. 40 μL of a 5 mM solution of S-2765 (DiaPharma) was added to all wells. The plate was sealed and incubated for 6 hours at 37° C. Absorbance was read at 405 nm in a microplate reader. Activity of samples was determined by comparing FX activation levels of samples to a F7 calibration curve.

Rat PK Study-Animals, Study Protocol (Inject of Preps, Sampling of Blood and Prep, ELISA, Data Analysis, Sacrifice of Animals).

Proteins (F7, V2, V1, dV2 and dV1) were administered intravenously at 0.1 mg/kg into Sprague Dawley rats. Plasma samples were taken starting at 1min post administration and analyzed by FVII ELISA.

HemA-PK Study

Proteins (F7, dV1) were administered i.v. at 1.0 mg/Kg into HemA mice. Plasma samples were taken starting at 5 min post administration and analyzed by FVII ELISA and sTF-PT assay.

FVII ELISA on Plasma Samples

Materials

Monoclonal antibodies against FVIIa were used. One monoclonal antibody furthermore was biotinylated. Purified FVIIa variants (wild type or de-sialylated) are used as assay calibrators and assay controls. Blocking buffer is 1% (w/v) casein in 30 mM Tris pH 7.2, 60 mM NaCl, 0.03% Tween-20. Assay dilution buffer (ADB) is 0.1% (w/v) casein, 50 mM Tris pH 7.2, 0.1M NaCl, 0.05% Tween-20. Assay wash buffer is PBS+0.05% Tween-20. Immunoassay plates are Greiner Microlon high binding plates (#655061). Streptavidin-horse radish peroxidase (SA-HRP) is from R&D Systems. HRP substrate Ultra-TMB is from ThermoFisher Pierce. Blank mouse plasma was obtained from CD1 or HemA mice either commercially (Bioreclamation) or through in-house sources. All other materials (casein, Tris, NaCl, Tween-20, PBS, sulfuric acid) are of reagent-grade quality.

Method for FVIIa Sandwich Immunoassay 96-well assay plates are coated with 0.1 ml/well of antibody against FVIIa, 1 µg/ml in PBS, overnight at 4° C. The plates are aspirated and blocked with 0.2 ml/well of blocking buffer for at least 2 hr at room temperature with rotation (150 rpm). Following blocking, the wells are washed 4×0.3 ml/well of wash buffer. FVIIa samples or standards are diluted 1:20 to a final concentration of 5% plasma in ADB and incubated 0.1 ml/well for at least 1.5 hr at room temperature with rotation. All standards, controls, and samples are measured in triplicate wells. After washing the plates as previously described, biotinylated antibody against FVIIa is added, 42 ng/ml in ADB, 0.1 ml/well, and the plates are incubated for at least 1 hour at room temp with rotation. The plates are washed, followed by incubation with streptavidin-HRP, 1:1000 in ADB, incubating at least 1 hour at room temp with rotation. After a final plate wash, the wells are developed with 0.1 ml/well of Ultra-TMB, stopping the reaction with 0.05 ml/well of 2M sulfuric acid. The stopped reactions are read at OD-450 nm, and the data are analyzed and calibrated. The lower limit of quantitation (LLOQ) for the assay is typically 15-30 ng/ml FVIIa in 100% plasma.

Soluble Tissue Factor (sTF)-Based Modified PT Assay to Measure rFVIIa Activity

A Prothrombin Time (PT) assay was performed to measure the activity of human rFVIIa in HemA mouse ex vivo plasma samples.

Briefly, 50 µL of sample containing 10% of HemA mouse plasma and 50% of human FVII-deficient plasma (George King Inc) in aPTT buffer (0.15 M NaCl, 0.05 M Tris pH 7.5, 0.1% BSA) were mixed with 50 µL of sTF-PT reagent and incubated at 37° C. for 30 sec. The sTF-PT reagent was composed of 1 volume of 2 µM recombinant human soluble TF (sTF$_{1-221}$) and 1 volume of 8 µM phospholipid vesicles (PS$^{20}$:PC$^{40}$:PE$^{40}$) Clotting was initiated by adding 50 µL of 25 mM of CaCl$_2$ and the clotting time was recorded on a STA Coagulation Analyzer (Diagnostica Stago Inc). The standards consisted of rFVIIa (wt-rFVII or modified rFVIIa variants) diluted 2-fold serially from 200 to 0.78 ng/mL.

Efficacy of Desialylated V2 in Hemophilia A (HemA) Mice

Acute Tail Cut Efficacy Study

To determine the blood loss, mice were anesthetized with isoflurane and the tails were placed in 37-38° C. warmed 0.9% saline in 15 ml plastic tubes for 10 min. The tail was cut at 4 mm from the tip by scalpel and immediately placed back into a separate pre-warmed 15 ml plastic tube containing 10 ml of saline. The mouse was allowed to bleed freely over 40 min. Desialylated V2 and F7 were dosed intravenously either 5 minutes after or 15- and 30-minutes before tail cut injury. Blood loss was quantified gravimetrically by weighing tubes before and after blood was collected.

Tail Vein Transection Efficacy (TVT) Study

HemA mice were dosed with desialylated V2 or F7 by tail vein injection at 1 hr before or 5 min after tail vein transection injury. Appropriate anesthesia was used. The tail vein was transected with a #11 scalpel straight blade, and a timer was started. The mouse was then returned to its individual clean cage with white paper bedding (VersiDri™) placed on top of a 4×8 inch heating pad. The animal activity status was monitored hourly for the next 9 hrs and at the 24 hr time point. Any mouse that showed signs of reduced activity level was noted on the monitor form and any mouse that showed signs of excessive blood loss was euthanized immediately.

Thrombin-Antithrombin (TAT) Assay in HemA Mouse Plasma

Reagents:

(1) Capture Antibody: Anti-thrombin polyclonal antibody from Enzyme Research Labs, Cat #TAT-EIA-C.; (2) Detection Antibody: HRP-conjugated anti-AT-III polyclonal antibody, from Enzyme Research Labs, Cat #TAT-EIA-D, (3) Assay Diluent:from Enzyme Research Labs, Cat #TAT-EIA-D, (4) HRP Substrate: Amplex Red, Invitrogen, cat #A12216, (5) Alpha-Thrombin: from Enzyme Research Labs, Cat #HT-1002a, stored at −80° C., (6) AT-III: from Enzyme Research Labs, Cat #HAT, stored at −80° C., (7) BSA: from Sigma, Cat #A-7030; (8) AT-III Deficient Plasma: Purchased from Enzyme Research Labs, Cat: AT-DP, stored at −80° C.

Buffers (1) TAT standard buffer: 20 mM Tris-HCl, pH7.4, 0.15M NaCl, 1 mM EDTA, 0.05 U/mL heparin; (2) Coating Buffer: 1 tablet of bi-carbonate+100 ml dH20, store at 4° C.; (3) Blocking buffer: 2% BSA-PBS; (4) Sample dilution buffer: add 0.1M HEPES, pH7.4, 0.15M NaCl, 1% BSA, 0.05% Tween20, filter and aliquot, store at −20° C.; (5) Substrate buffer: add 50 µL of 5 mg/mL Amplex Red, 20 µl of 3% H$_2$O$_2$ to PBS buffer. Mix, fresh prepared before adding to plates; (6) Preparation of 1 µM TAT standard stock: add 100 µL of human AT-III at 1.36 mg/ml and 5.93 µL of human thrombin at 3.28 mg/mL to 419 µL of TAT buffer, mix, incubate 10-20 min at 37° C.; (7) Preparation of 60 nM TAT standard stock: Add 50 µL of 1 µM TAT complex to 783 µL of AT-III deficient plasma, mix. Aliquot 50 µL/vials, store at −80° C.

Assay Procedure

1. Dilute anti-thrombin pAb (capture antibody) in bicarbonate buffer (1:100 dilution: for one 96-well plate, add 110 µL of antibody to 11 mL of bicarbonate buffer).
2. Add 100 µL diluted coating antibody to each well on a 2HB Immulon 96-well plate. Tap plate gently to ensure all liquid to cover bottom of plate. Seal the plate and incubate overnight at 4° C.
3. Wash 4 times with 300 µL Wash buffer in an automated plate washer. Following the last wash, invert the plate and tap it against a clean paper towel.
4. Add 150 µL of Blocking buffer (2% BSA-PBS) to each well. Seal the plate and incubate at Room temperature for 1.5 hour.
5. Wash 4 times with 300 µL Wash buffer with an automated plate washer. Following the last wash, invert the plate and tap it against a clean paper towel.
6. Add 100 µL of Standard, sample and QC to each well in triplicates and incubate plates at room temperature for 2 hr at room temperature.
7. Wash 4 times with 300 µL Wash buffer with an automated plate washer. Following the last wash, invert the plate and tap it against a clean paper towel.
8. Add 100 µL HRP-detection antibody (1/100, add 110 µL of antibody to 11 mL of conjugate diluent), to each well. Seal the plate and incubate for 1 hour at room temperature.
9. Wash 4 times with 300 µL Wash buffer with an automated plate washer. Following the last wash, invert the plate and tap it against a clean paper towel.
10. Add 70 µL of Amplex Rd substrate (fresh prepared) to each well.
11. Place the plate in the dark at room temperature and incubate for 15-30 min.
12. Read the plate at OD485 nm/595 nm.
13. Plot standards with 4-parameter curve fit; Concentration from Controls and each sample were calculated from standard in each ELISA plate.

Efficacy of Desialylated V2 in Coagulation-Competent Mice

An acute tail cut study was performed to determine the efficacy of dV2 in coagulation-competent mice. Coagulation-competent mice were anesthetized with isoflurane and the tails were placed in 37-38° C. warmed 0.9% saline in 15 ml plastic tubes for 10 min. After an iv administration of 5 mg/kg tissue plasminogen activator (tPA), the tail was cut at 50 mm from the tip by scalpel and placed back into a separate pre-warmed 15 ml plastic tube containing 10 ml of saline. Desialylated V2 and F7 were dosed intravenously immediately after tail cut injury. The mouse was allowed to bleed freely over 45 min. Blood loss was quantified gravimetrically by weighing tubes before and after blood was collected.

Results

In Vitro Characterization of Desialylated or Deglycosylated Proteins

Figure 7:
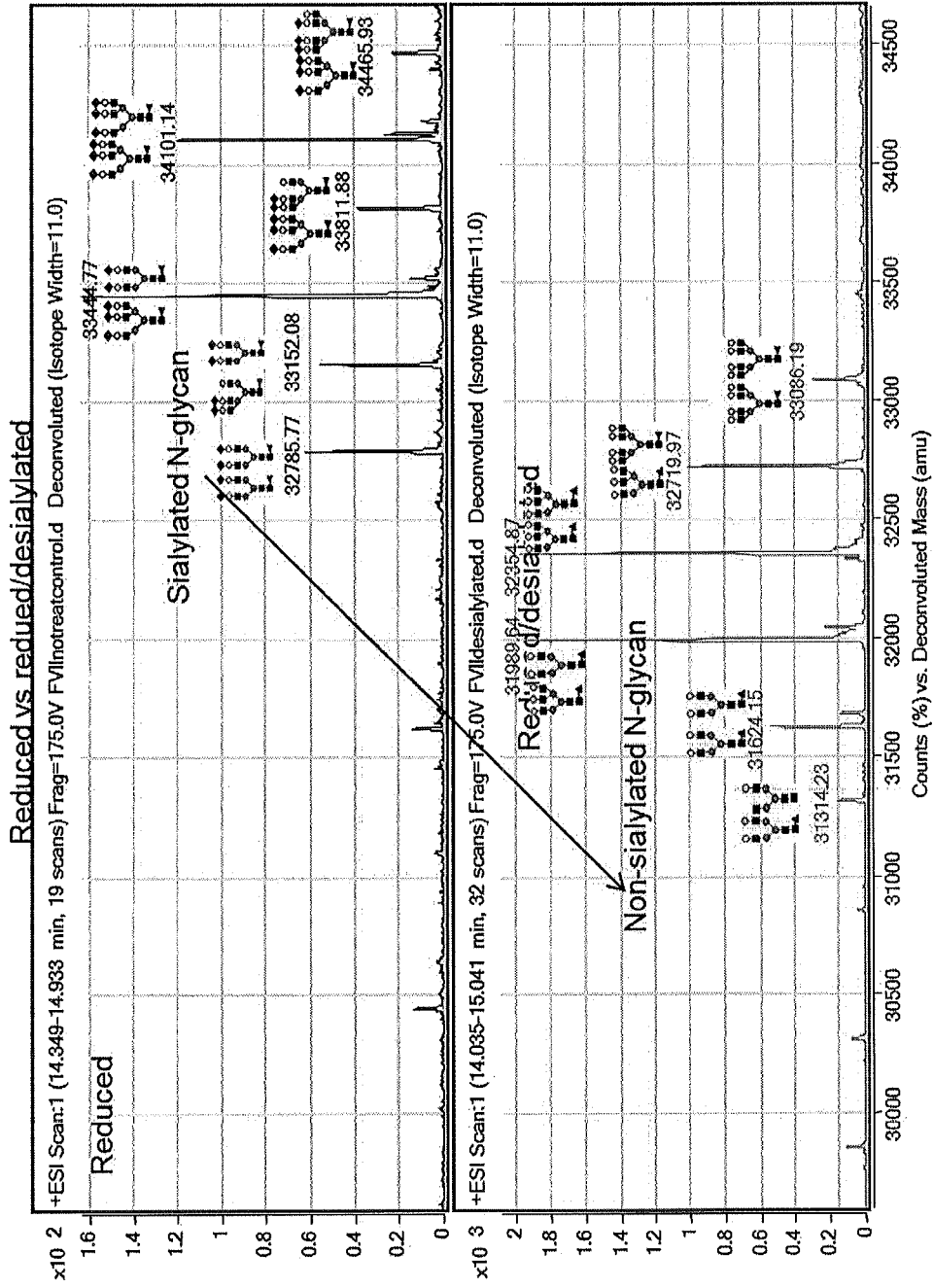
FIG. 7 shows the results of an LC-MS method to identify the sialic acid remaining on the heavy chain of V2 after desialylation according to the conditions of the experiment.
Figure 8:
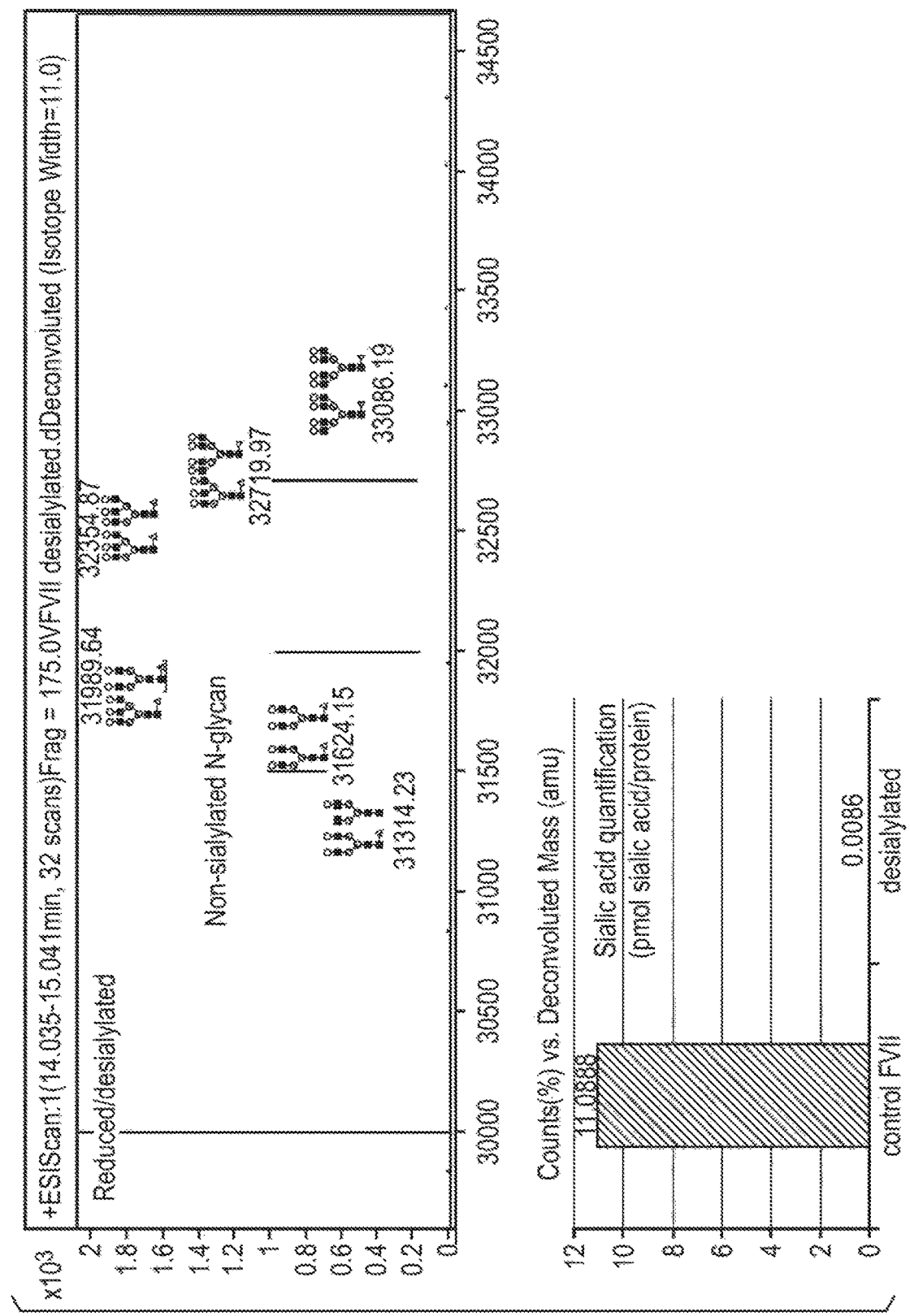
FIG. 8 shows the analysis of desialylated V2 for sialic acid content.
Figure 9:
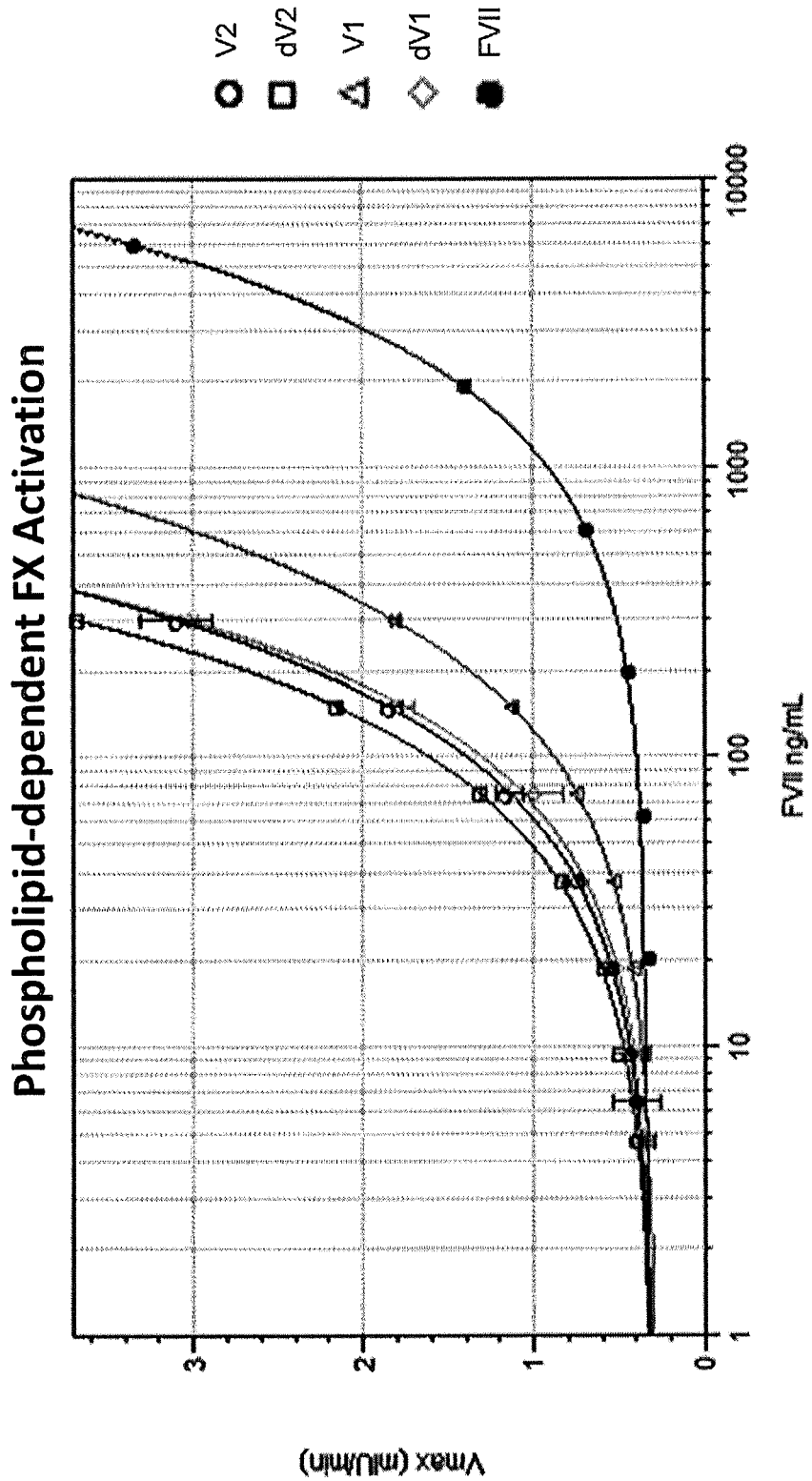
FIG. 9 shows the results of a phospholipid FX activation assay.
Figure 10:
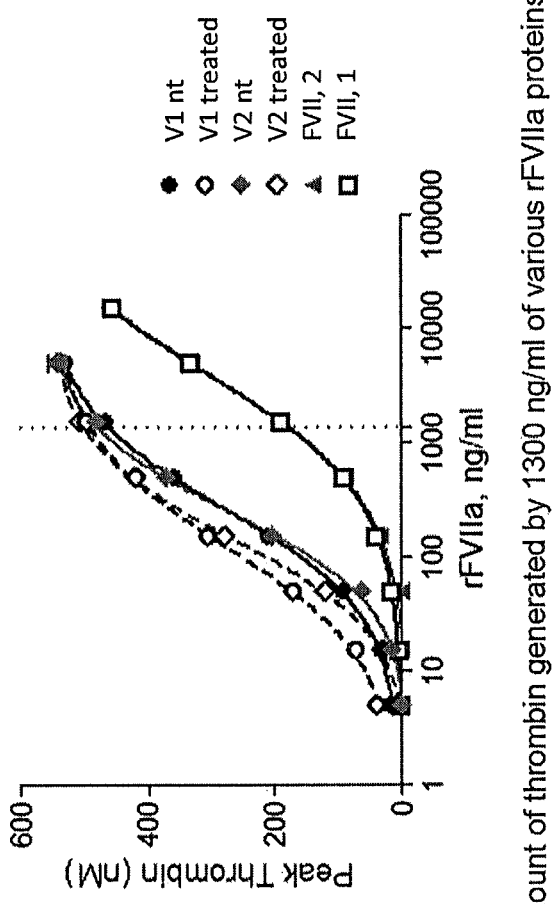
FIG. 10 shows the results of a PL-TGA assay on desialylated proteins.

The heavy chain of dV2 was analyzed by LC-TOF MS. Analysis showed that that the N-Glycans on the heavy chain contained no sialic acid post sialidase treatment. Such analysis on the light chain was complicated by the presence of the Gla domain. To get a global picture of sialic acid content of the treated molecule, Sialic Acid Fluorescence Labeling was carried out. This method showed that greater than 99.9% of sialic acid was removed on V2 during the desialylation process. FIG. 7 shows the analysis of desialylated V2 for sialic acid content. LC-TOF MS analysis and Sialic Acid Fluorescent Labeling were utilized. Sialic acid content analysis was carried out on dV1 as well with similar results (data not shown). The desialylated molecules were tested for activity by both the phospholipid-dependent Xa activation and phospholipid-dependent TGA assay. The PL-Xa and PL-TGA assays demonstrated that activity of the proteins post desialylation was not reduced. (See FIG. 9 and FIG. 10). FIG. 9 shows PL-FXa activation assay on desialylated proteins. Desialylated V1 and V2 (dV1, dV2) were tested for activity using the Phospho-lipid FXa activation assay. Both desialylated proteins had slightly higher activity in this assay as compared to their unmodified parental molecules. FIG. 10 shows PL-TGA assay on desialylated proteins. By PL-TGA, dV2 and dV1 exhibited slightly increased activity over their unmodified parental molecules. Results were normalized to F7.

Figure 11:
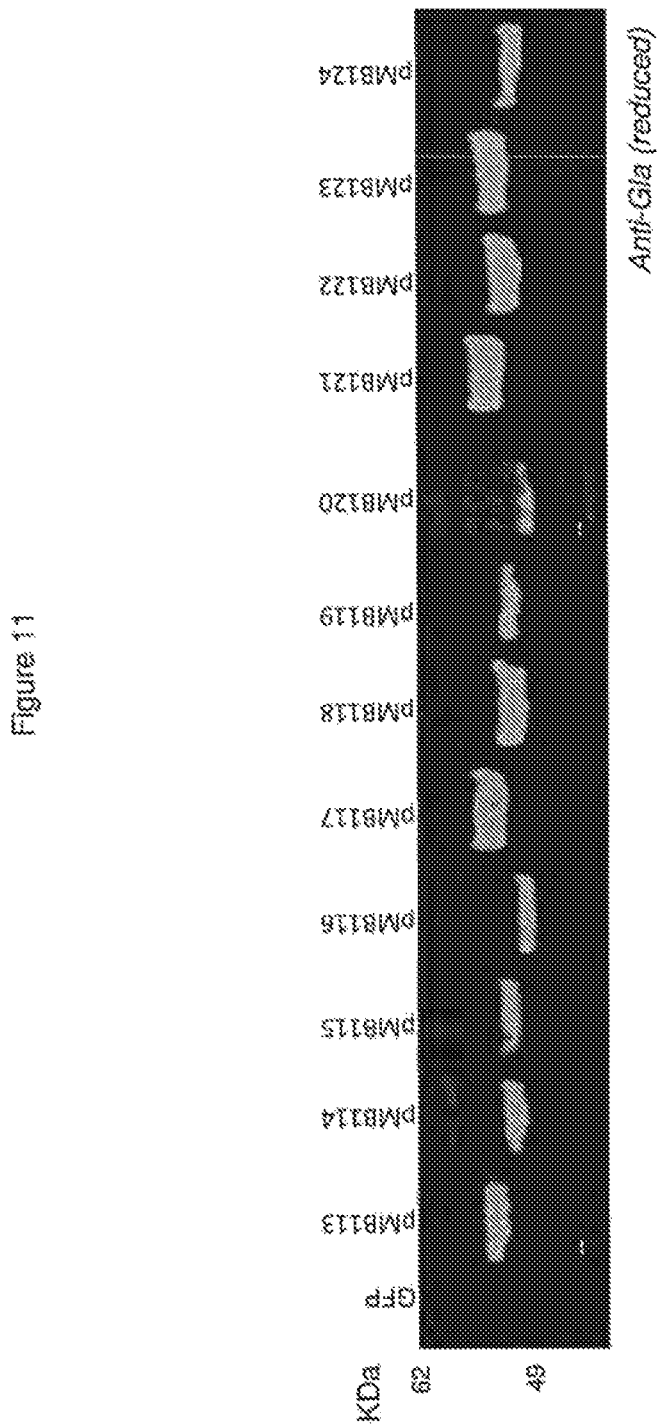
FIG. 11 shows expression of hypoglycosylated Factor VII variants.
Figure 13:
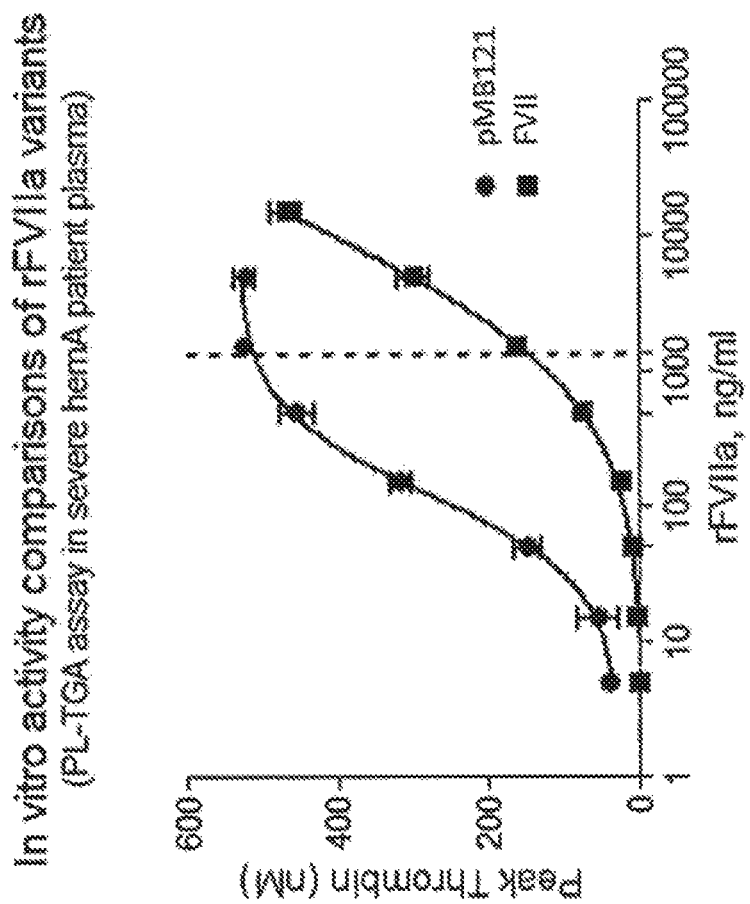
FIG. 13 shows the results of a PL-TGA assay on purified hypoglycosylated variant pMB121.
Figure 14:
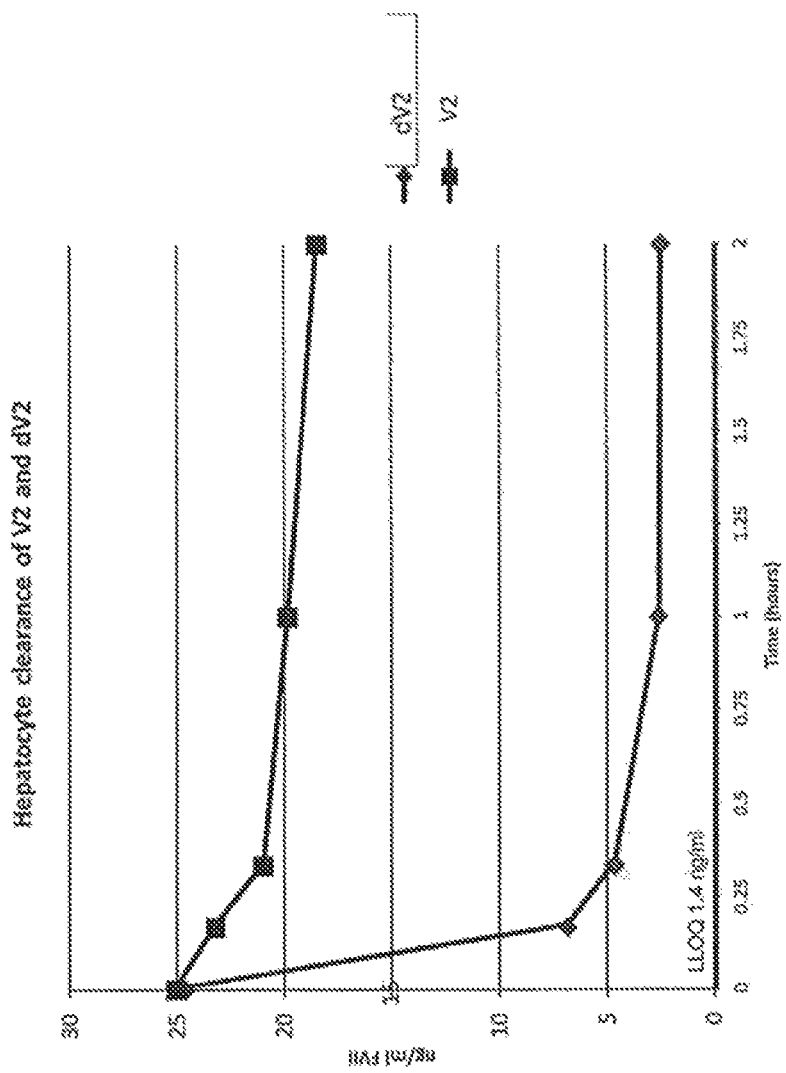
FIG. 14 shows the in vitro hepatocyte clearance of desialylated V2 compared to wild type Factor VII.
Figure 15:
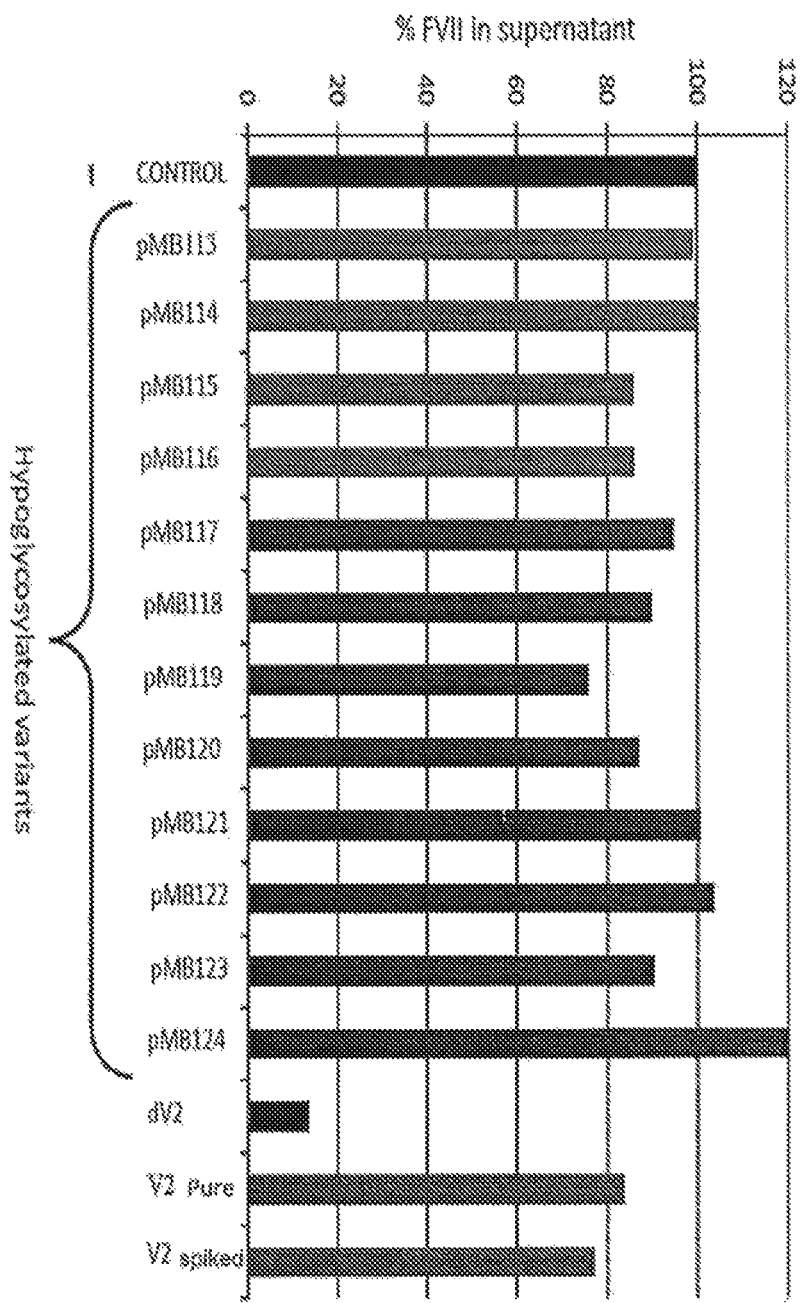
FIG. 15 shows the results of in vitro hepatocyte clearance with Factor VII variants. The hypoglycosylated variants did not display an increase in clearance in this model. This result suggests a different clearance mechanism for these molecules from that utilized by the desialylated V2.

The PL-Xa assay consistently showed a measurable increase in activity of dV2 and dV1 over their unmodified parental molecules. The hypoglycosylated wtFVIIa, V2, and V1 molecules were expressed (FIG. 11) and tested as crude expression extracts for both expression and activity. FIG. 11 shows expression of hypoglycosylated FVII variants. Media samples 4 days post electroporation were analyzed for FVII expression. Western blot analysis using an anti-Gla domain antibody shows expression of the variants. Removal of the N-Glycan sites did not appear to affect activity when normalized for expression levels. FIG. 12 shows determination of "specific activity" of hypoglycosylated FVII variants using transfection supernatants. The activity of the crude expression supernatants from two transient transfections of the hypoglycosylated variants were assayed by the Xa activation assay. When normalized for expression as measured by ELISA, no decrease in activity as a result of N-glycan removal was noted. As expected in this assay, V1 and F7 proteins had similar activities while V2 molecules had lower activity, a result of its TF-independence. This was further demonstrated by the PL-TGA activity assay carried out on purified hypoglycosylated V2 with only 2N-Glycans (N322 and N145) referred to as pMB121. FIG. 13 shows PL-TGA assay on purified hypoglycosylated variant pMB121. By PL-TGA assay, pMB1212 shows enhanced activity over F7 similar to unmodified V2. In vitro clearance of these molecules was tested in a hepatocyte clearance model. dV2 demonstrated significant clearance in this model over unmodified V2 (FIG. 14), while marginal or no increase in clearance was seen for the hypoglycosylated variants (FIG. 15).

Rat PK and HemA PK

Figure 16:
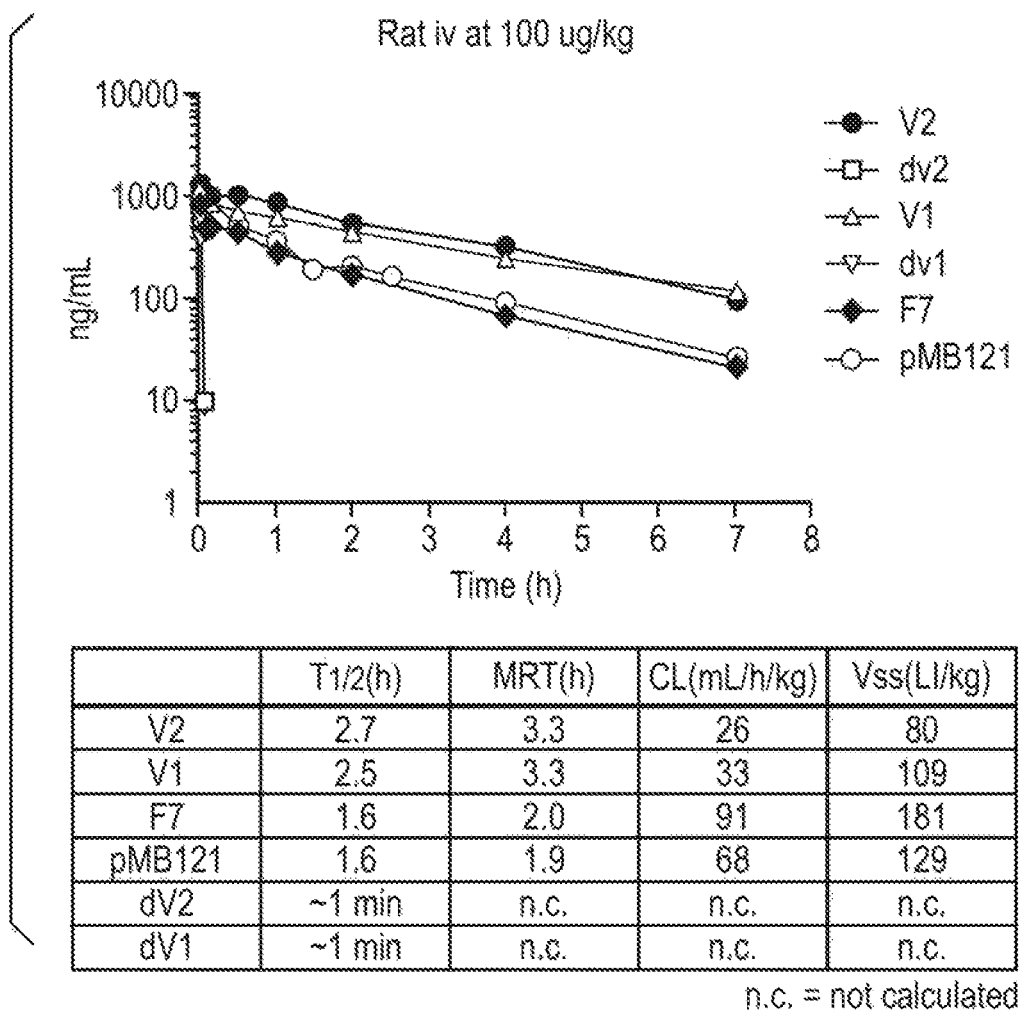
FIG. 16 shows pharmacokinetic study results in rat. Half-lives of the desialyated V2 and V1 were significantly shorter than their unmodified parental molecules in Sprague Dawley rats as measured by Factor VII ELISA.

Pharmacokinetic studies in Sprague Dawley rats demonstrated that desialylated and hypoglycosylated proteins cleared significantly faster than their unmodified counterparts as measured by a FVII ELISA. FIG. 16 shows the rat pharmacokinetic results. Half-lives of the desialyated V2 and V1 were significantly shorter than their unmodified parental molecules in Sprague Dawley rats as measured by FVII ELISA. This was true for desialylated V2, desialylated V1, and pMB121 (hypoglycosylated V2). The t1/2 for both the desialylated molecules was less than 1 min whereas the t1/2 of their parental proteins was approximately 2.5 hrs. The clearance of the hypoglycosylated V2 molecule pMB121 was equivalent to that of F7 with a t1/2 of 1.6 hrs. The PK study in HemA mice had a similar result with dV2 and F7 having half-lives of approximately 3 min and 2.6 hrs, respectively (FIG. 17 (A)). The short half-life was confirmed by sTF-PTT clotting assay (FIG. 17 (B)). FIG. 17 shows HemA PK results. The half-life of desialyated V2 was significantly shorter than its unmodified parental molecule in HemA mice as measured by A) FVII ELISA and B) the sTF-PT assay.

Figure 18:
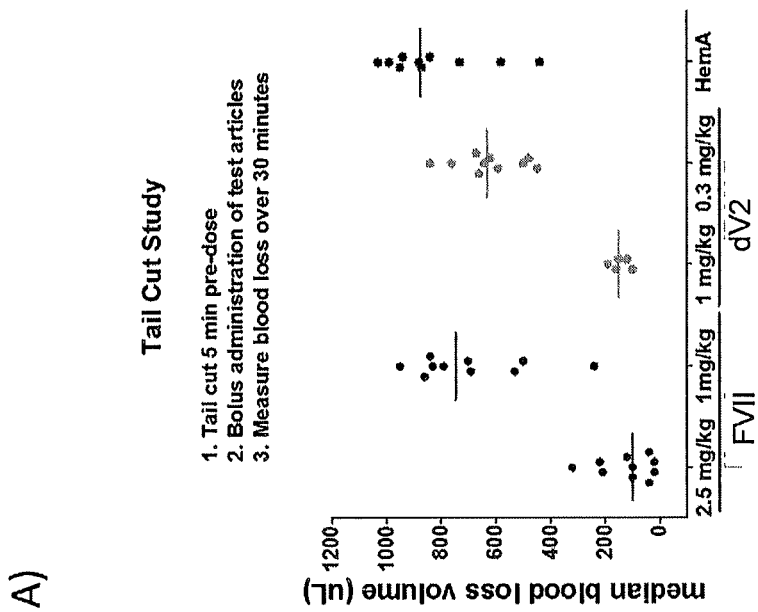
FIG. 18 shows a desialylated V2 efficacy study in HemA mice.

HemA Efficacy Models dV2 was tested in HemA mice for efficacy. Using the HemA tail cut model, dV2 was shown to be efficacious at a dose of 1 mg/kg (bolus, iv). By comparison, in this model, the efficacious dose for F7 was 2.5 mg/kg (bolus, iv). These results demonstrate that dV2 is more efficacious than F7 (FIG. 18 (A)). This model was also utilized to show that the efficacy of dV2 is cleared faster than that of F7 (FIG. 18 (B)). FIG. 18 shows the results of the desialylated V2 efficacy study in HemA mice. Studies with dV2 show that this molecule is A) more efficacious than and B) has faster efficacy clearance than F7 in the HemA tail cut model.

Figure 19:
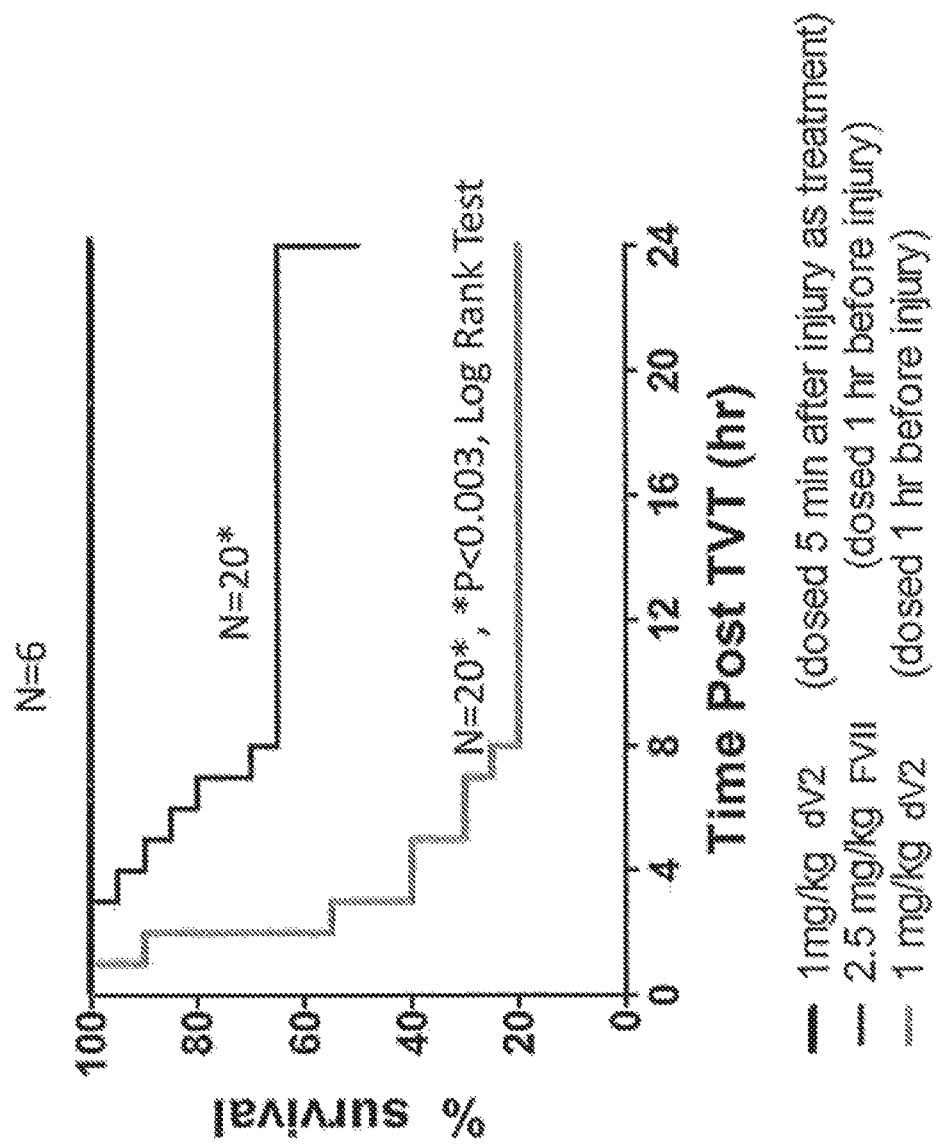
FIG. 19 shows a desialylated V2 efficacy study in TVT HemA model.
Figure 20:
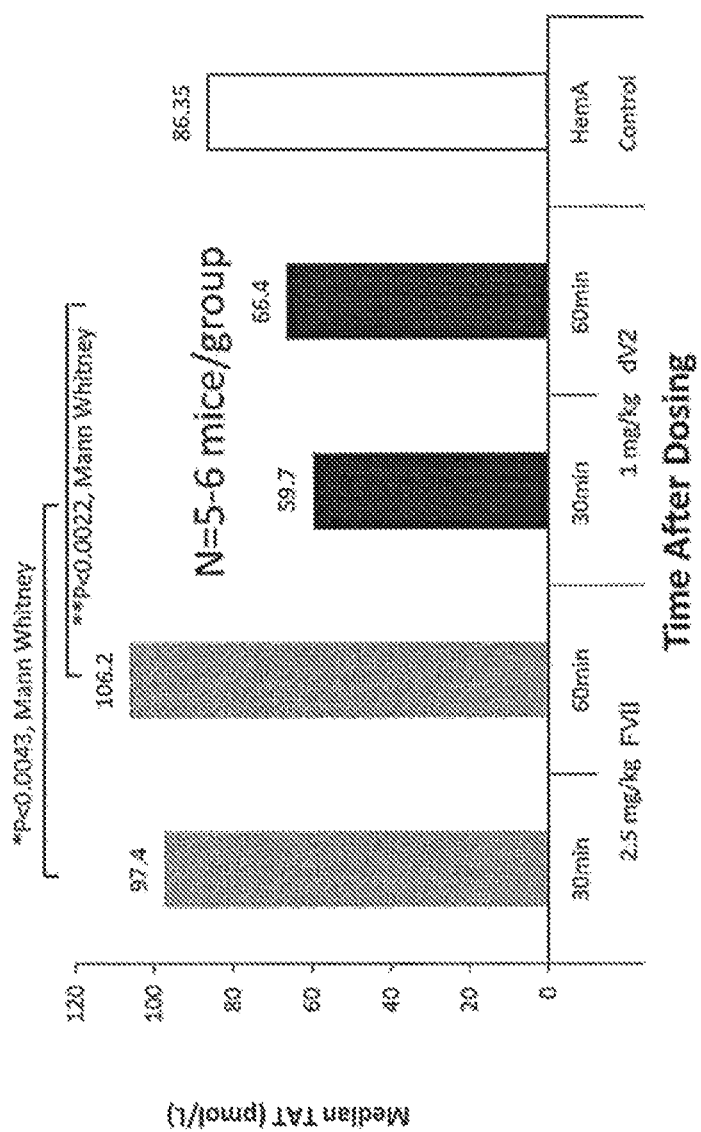
FIG. 20 shows the results of thrombin-antithrombin ("TAT") generation in HemA mice with desialylated V2 compared to Factor VII.

Using the more sensitive TVT model, the faster efficacy clearance of dV2 over F7 was also demonstrated and the efficacious dose confirmed. FIG. 19 shows a dV2 efficacy study in TVT HemA model. TVT studies using an efficacy model (TVT) with higher sensitivity confirmed dV2 has faster efficacy clearance than F7. Thrombin Anti-Thrombin (TAT) measurements as a marker of thrombogencity performed at 30 and 60 min post administration in HemA mice showed significantly lower levels for dV2. FIG. 20 shows TAT measurements. In HemA mice, dV2 administered at its efficacious dose (1 mg/kg) generated less Thrombin Anti-Thrombin (TAT) than the efficacious dose of F7 (2.5 mg/kg). This data, taken with the efficacy data, would suggest that dV2 has a more favorable therapeutic index than F7.

Figure 21:
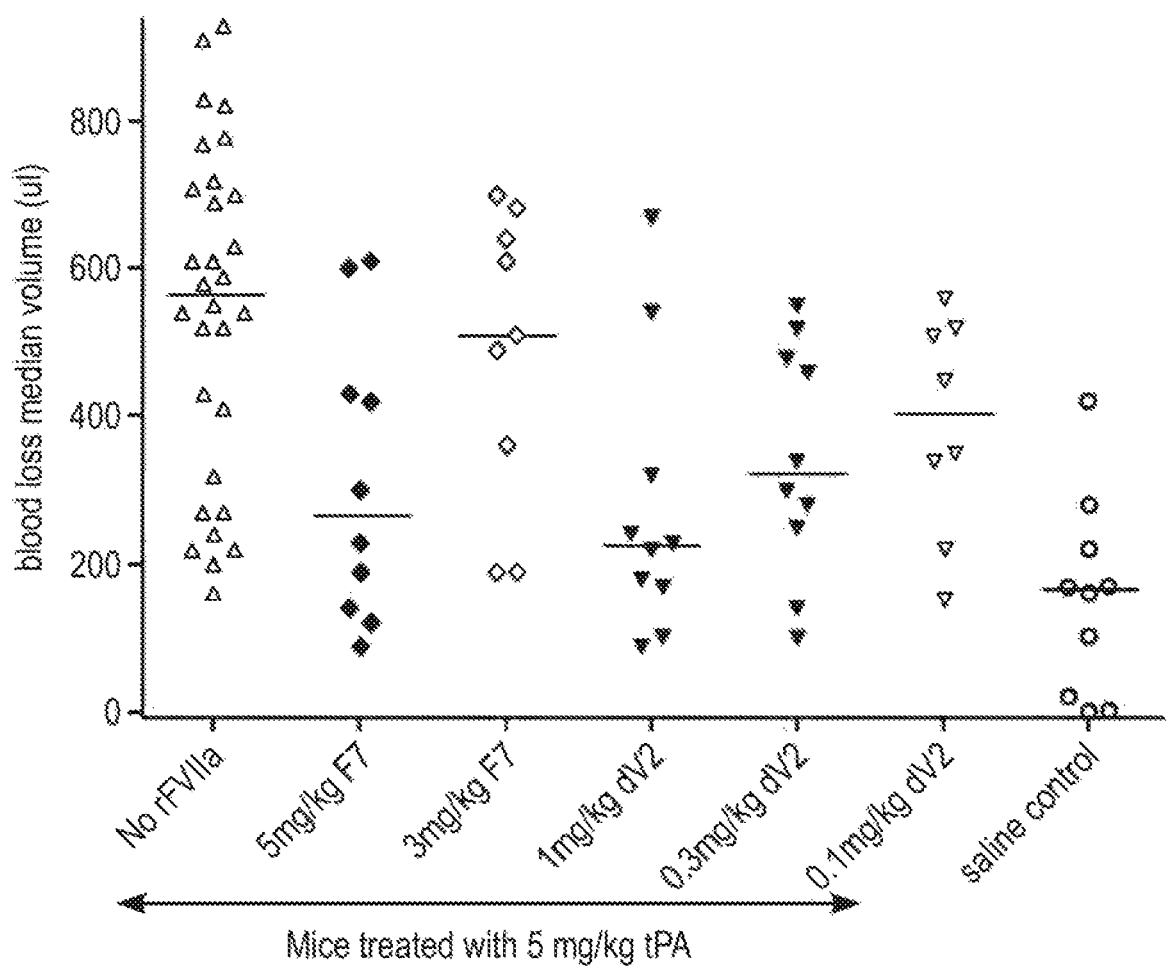
FIG. 21 shows a desialylated V2 efficacy study in coagulation-competent mice.

Efficacy in Coagulation Competent Mice dV2 was tested in tPA-treated, coagulation-competent mice for efficacy. Using the tail cut model, dV2 was shown to be efficacious at doses of 0.3-1 mg/kg (bolus, iv). By comparison, in this model, the efficacious dose for F7 was 5 mg/kg (bolus, iv). These results demonstrate that dV2 is more efficacious than F7 (FIG. 21). FIG. 21 shows the results of the desialylated V2 efficacy study in tPA-treated, coagulation-competent mice.

Clearance and Efficacy of Desialylated Wild-Type Factor VII (dWT VIIa)

Desialylated wild-type Factor VII (dWT VIIa) was produced as described above using NovoSeven® obtained from Novo Nordisk as the starting Factor VII material and desialylating that starting polypeptide using soluble sialidase enzyme, as described above. The dWT VIIa was found to have a purity of >99%, low endotoxin, and no detectable sialic acid. Additionally, mass spectrometry analysis showed selective removal of sialic acid.

The activity of this dWT VIIa material was analyzed and compared to wild-type Factor VII using the Biophen FVII chromogenic assay and modified PT Assay, as described above. Each of these analyses showed the dWT VIIa to have nearly identical activity to the wild-type Factor VII polypeptide.

Figure 22:
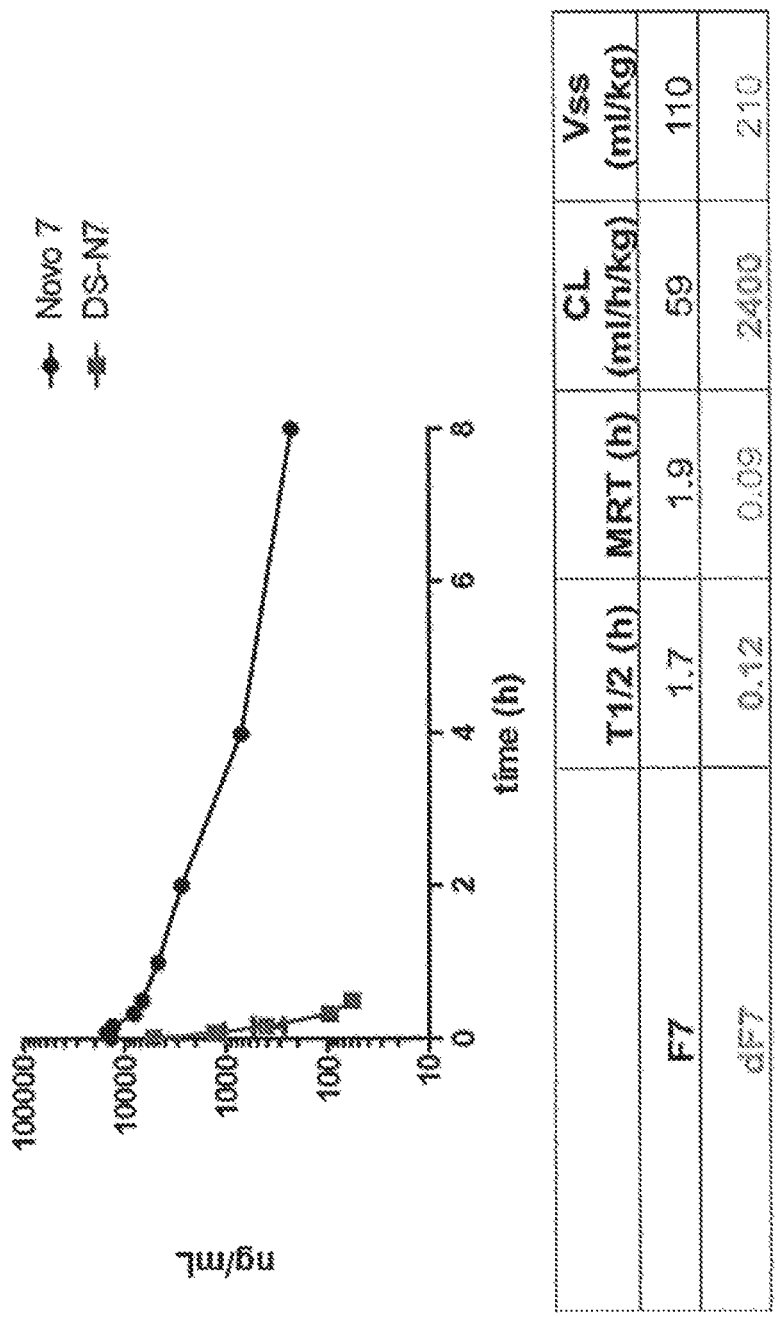
FIG. 22 shows the in vitro hepatocyte clearance of desialylated wild-type Factor VII (dWT VIIa) compared to wild-type Factor VII with normal conjugation of sialic acid.

Clearance of dWT VIIa and wild-type Factor VII (1 mg/kg) were also analyzed and compared using the human tissue factor knock-in (TFKI) mice mouse model. As shown in FIG. 22, the half-life of dWT VIIa was significantly shorter than wild-type Factor VII and clearance (ml/h/kg) was more than 40 times faster.

Figure 23:
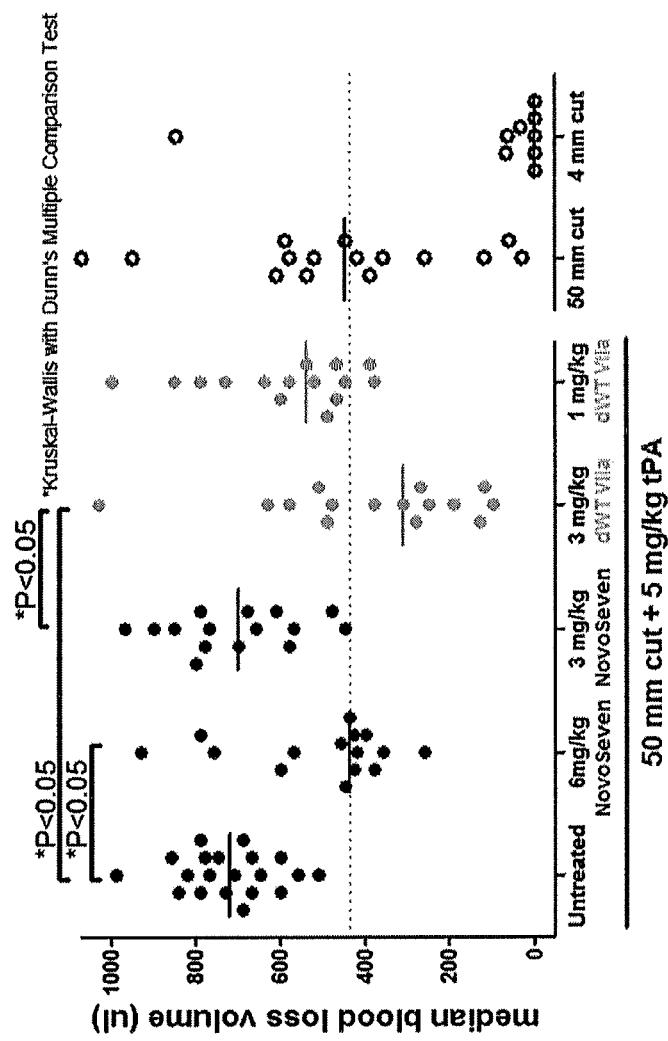
FIG. 23 shows tail cut study results in the human tissue factor knock-in (TFKI) mice for dWT VIIa compared to wild-type Factor VII. Desialylated Factor VII was found to be significantly more efficacious than wild-type Factor VII.

The efficacy of dWT VIIa in comparison to wild-type Factor VII was investigated using TFKI mice and the tail cut method described above. Briefly, 5 mg/kg tPA was injected intravenously into the mice, followed by clipping of the tail 50 mm from the tip. Wild-type Factor VII (NovoSeven®) or dWT VIIa were then injected intravenously with dosages ranging from 1-6 mg/kg. Blood was then collected from the tail for 45 minutes, with unstable clots being disrupted every six minutes throughout the collection period. As shown in FIG. 23, dWT VIIa was surprisingly found to be significantly more efficacious than wild-type Factor VII. More specifically, a 3 mg/kg dose of dWT VIIa caused reduced blood loss in comparison to a 6 mg/kg dose of wild-type Factor VII. Given the results of this analysis, it was determined that 2 mg/kg dWT VIIa is a bioequivalent dose to 6 mg/kg wild-type factor VII.

Figure 24:
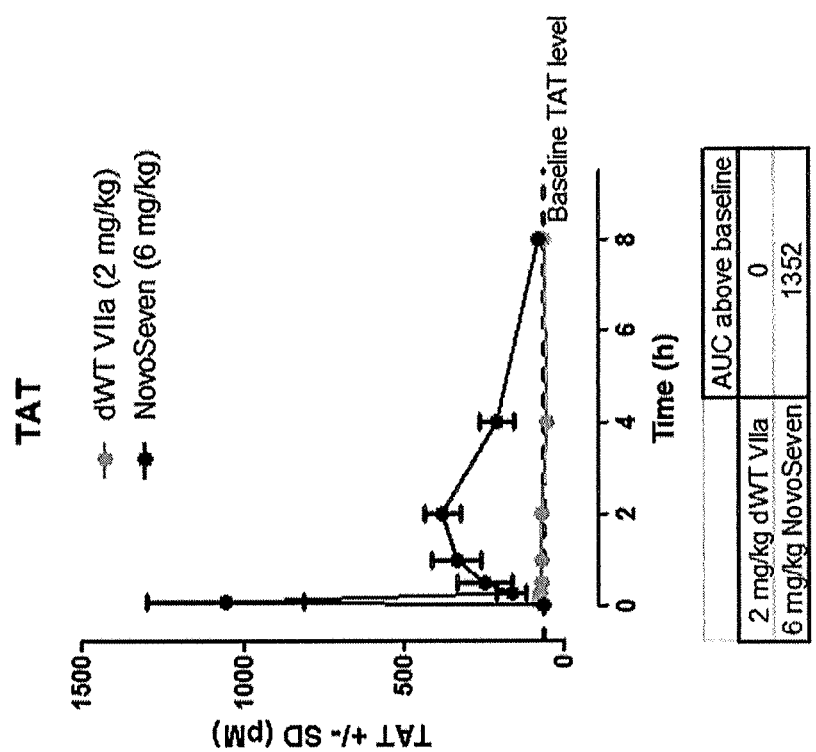
FIG. 24 shows results of an ELISA analysis of Thrombin Anti-Thrombin (TAT) complexes after administration of either dWT VIIa or wild-type Factor VII

The ability of dWT VIIa and wild-type Factor VII (NovoSeven®) to cause systemic coagulation was also investigated by the Thrombin Anti-Thrombin (TAT) method described above. Mice were treated with bioequivalent doses of dWT VIIa (2 mg/kg) and wild-type Factor VII (6 mg/kg) and then the formation of TAT complexes was measured by ELISA. As shown in FIG. 24, the wild-type NovoSeven® Factor VII generated a significantly higher level of TAT than dWT VIIa. Given the fact that dWT VIIa generated only baseline TAT levels, this experiment suggests that this dose of dWT VIIa produces no observable systemic coagulation, despite the fact that the polypeptide is as efficacious as wild-type Factor VII.

Figure 25:
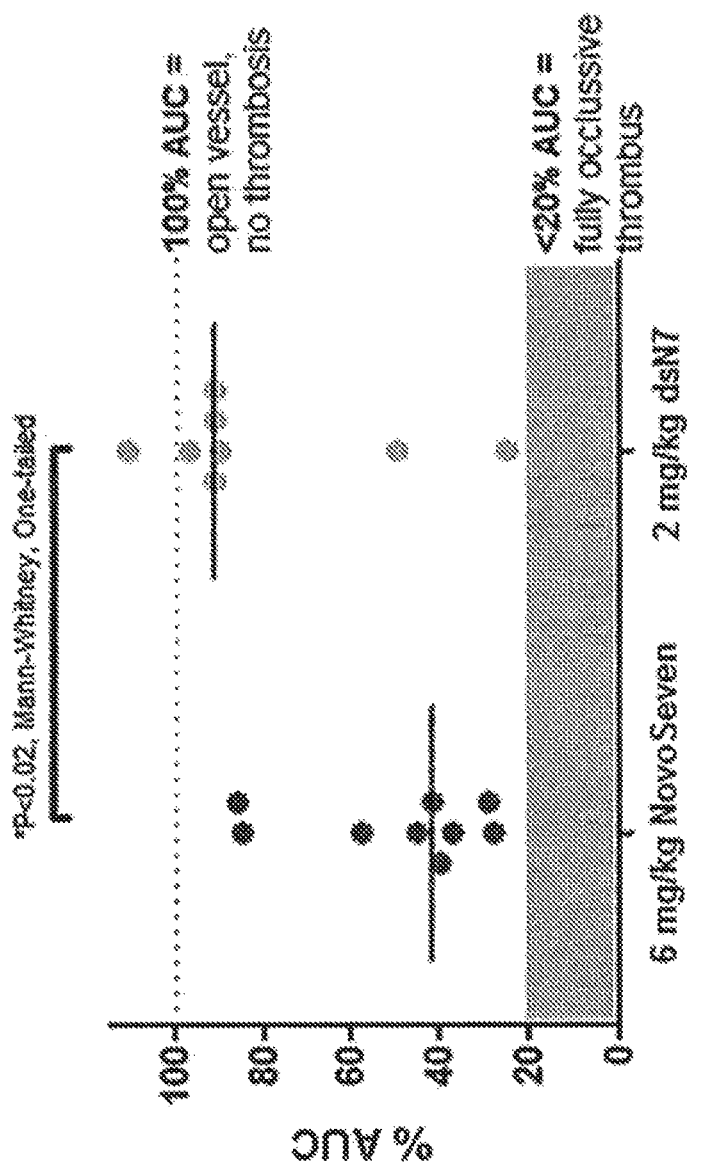
FIG. 25 shows the results of an analysis of thrombus formation in a $FeCl_3$ thrombosis model. The given dose of dWT VIIa produced greatly reduced thrombus formation as compared to wild-type Factor VII.

Further, the ability of dWT VIIa and wild-type Factor VII (NovoSeven®) to cause thrombus formation was also investigated in a $FeCl_3$ thrombosis model. Mice were treated with bioequivalent doses of dWT VIIa (2 mg/kg) and wild-type Factor VII (6 mg/kg) 15 minutes prior to initiation of the thrombosis study. Thrombosis was then initiated by administration of a 3.25% $FeCl_3$ solution and then thrombus formation was measured by Doppler for 30 minutes. The resulting blood flow data was plotted on a blood flow versus time graph and then the percentage of the area under the curve for the control sample was calculated to determine the reduction in blood flow caused by thrombus formation for each of the Factor VII treatment groups. As shown in FIG. 25, the wild-type NovoSeven® Factor VII generated a significantly reduced blood flow (average approx. 40%), while the dWT VIIa showed nearly no reduction in blood flow (average >90%). This experiment demonstrated that the given dose of dWT VIIa produced greatly reduced thrombus formation as compared to wild-type Factor VII.

Figure 26:
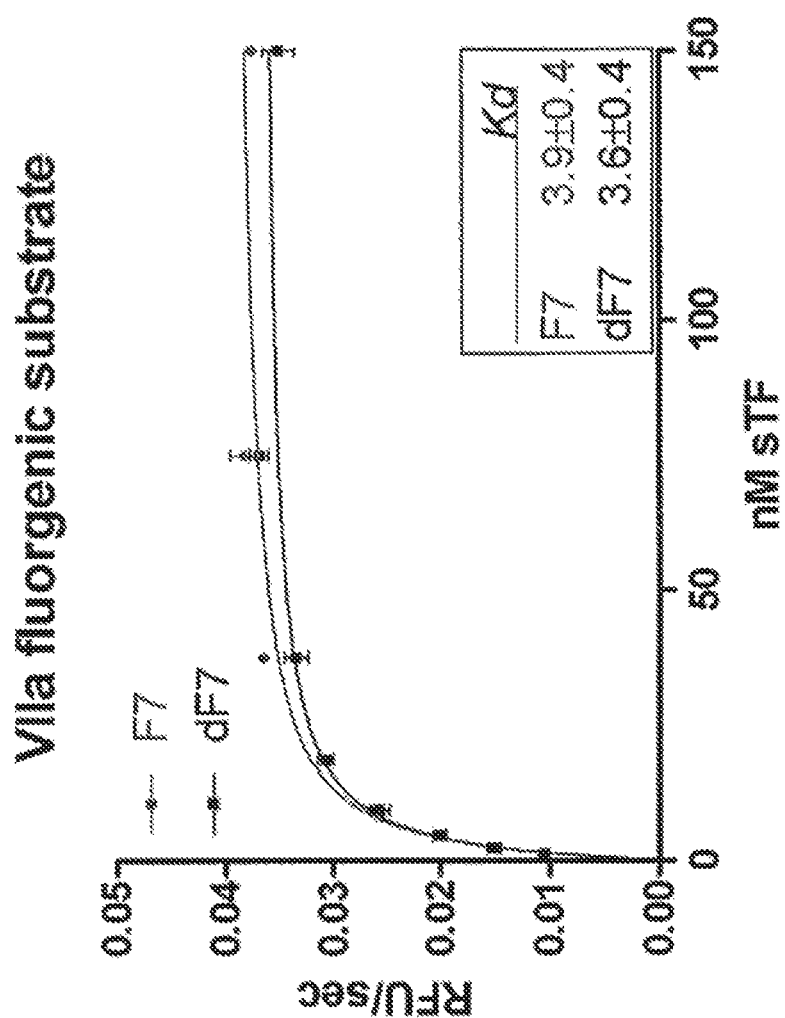
FIG. 26 shows the apparent binding affinities of dWT VIIa and wild-type Factor VII for soluble tissue factor as measured by a fluorogenic substrate.
Figure 27:
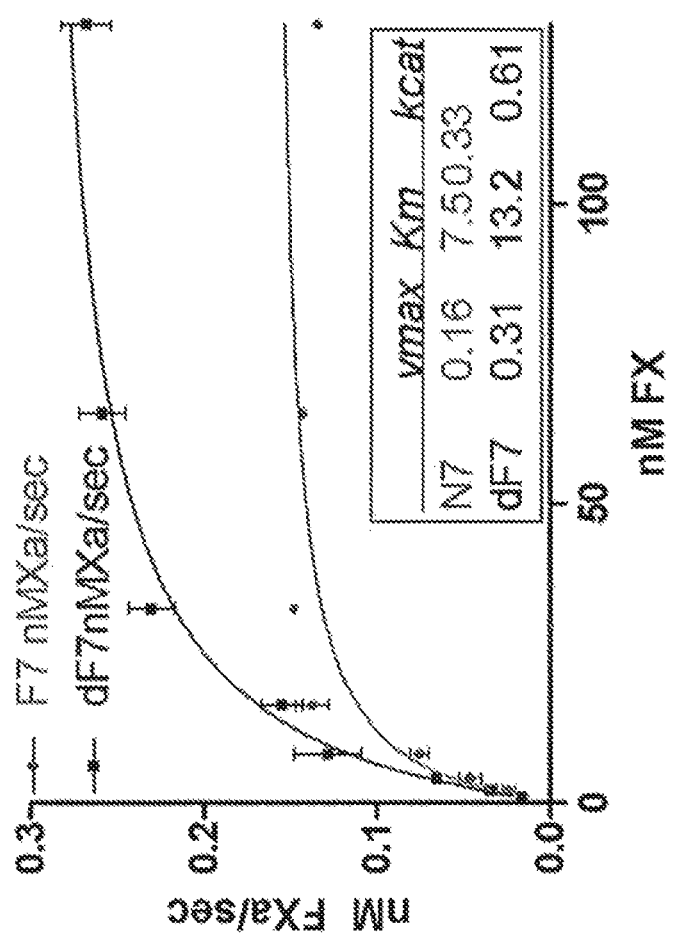
FIG. 27 shows the conversion of Factor X to Factor Xa by a complex of soluble tissue factor and either dWT VIIa or wild-type Factor VII.

The activity and efficacy of dWT VIIa compared to wild-type Factor VII was further investigated by examining the apparent binding affinities of these peptides for soluble tissue factor (sTF) using an SN-17c tripeptide fluorogenic substrate (HTI). As shown in FIG. 26, this analysis demonstrated that dWT VIIa (dF7) and wild-type Factor VII (F7) had equivalent apparent biding affinities for sTF. However, as shown in FIG. 27, in an experimental model examining the ability of these peptides to activate Factor X by titrating the Factor X concentration in the presence of sTF-Factor VII complexes (0.5 nM Factor VII [dWT VIIa or wild-type], 125 nM sTF), the Michaelis Menten kinetics for dWT VIIa and wild-type Factor VII demonstrate that dWT VIIa (dF7) can activate Factor X more effectively (approximately 2-fold) than wild-type Factor VII (F7). This data suggests that dWT VIIa is able to convert more Factor X to Factor Xa per Factor VII active site than its wild-type counterpart.

DISCUSSION

There is an unmet medical need to develop a therapeutic drug that is efficacious for the treatment of acute bleeding but with reduced thrombogenecity. An efficacious Factor VII polypeptide with a short half-life would potentially result in a molecule with a larger therapeutic window suitable for use in acute bleeds.

V2 and V1 are two Factor VIIa variants (FIGS. 1-3). These variants contain mutations to their Gla domains that increase their affinity for activated platelets and, in the case of V2, result in tissue factor independence. Both variants also have two additional N-Glycosylation sites, which results in a prolonged half-life as compared to wild type Factor VIIa, a trait that is advantageous for the treatment of hemophilia. However their use as treatments for acute bleeding would benefit from decreases in half-life. This modification would reduce the risk of off-target effects and, as a result, increase their therapeutic index. We have shown here that removal of the sialic acids present on the carbohydrate chains of V2 and V1 result in significantly faster clearance of the molecules in an in vitro hepatocyte clearance model. The hypoglycosylated variants did not clear faster in this in vitro model, which suggests that the mechanism of clearance between desialylated and hypoglycosyled molecules differ. In vivo studies conducted in Sprague Dawley rats demonstrated that the desialylated molecules (dV2 and dV1), as well as the hypoglycosylated variant pMB121, had a significantly decreased half-life. Interestingly, desialylated V2 and V1 both had increased clearance rates as compared to the reported rate for desialylated wild type FVIIa. (Appa et al, Thrombosis and Haemostasis 104.2/2010), a characteristic that may be due to their 2 additional N-glycans. One possible theory for this activity, without limitation on what is claimed herein, is that these extra N-Glycans would, upon desialylation, become additional ligands for the ASGPR or similar receptor and mediate faster clearance. Activity of these molecules was retained or increased in comparison to their parental molecules as measured by in vitro activity assays. Faster clearance of dV2 was further verified in vivo in a HemA mouse PK study and was shown to be efficacious in HemA tail clip and TVT studies.

Further, desialylation of wild-type Factor VII produced a Factor VII polypeptide that was cleared much more rapidly than wild-type, while also providing the surprising result of increased efficacy as shown in numerous experimental models.

Removal of the N-glycans or modification of the monosaccharide composition of the N-glycans of Factor VIIa or Factor VIIa variants results in faster clearing molecules. These molecules retain activity and are efficacious in vivo. The development of these fast clearing Factor VIIa molecules would be beneficial for the treatment of acute bleeding indications, as well as potentially being an antidote for the various anti-coagulants on the market.

What is claimed is:

1. An isolated variant Factor VII polypeptide comprising an amino acid sequence having at least 90% identity to the amino acid sequence of SEQ ID NO: 16 and comprising mutation(s) in the Gla domain that increase the variant Factor VII polypeptide affinity for activated platelets, wherein the variant Factor VII polypeptide comprises N-linked glycosylation sites of wild-type human Factor VII at amino acid residues 145 and 322 with reference to SEQ ID NO: 16 and further wherein the variant Factor VII polypeptide has a ratio of moles of conjugated sialic acid to moles of N-linked glycan between 0 and 2.0.

2. The isolated variant Factor VII polypeptide of claim 1, wherein the mutation(s) in the Gla domain that increase the variant Factor VII polypeptide affinity for activated platelets are P10Q and K32E.

3. The isolated variant Factor VII polypeptide of claim 1, characterized by having at least 50% of the activity to promote blood clotting as wild type Factor VII measured under the same conditions.

4. The isolated variant Factor VII polypeptide according to claim 1, wherein the ratio of moles of conjugated sialic acid to moles of N-linked glycan is less than 0.1.

5. The isolated variant Factor VII polypeptide according to claim 1, wherein the ratio of moles of conjugated sialic acid to moles of N-linked glycan is less than 1.0.

6. A method of preparing the isolated variant Factor VII polypeptide of claim 1, the method comprising
   (1) obtaining a sialylated Factor VII polypeptide comprising an amino acid sequence having at least 90% identity to the amino acid sequence of SEQ ID NO: 16 and comprising the N-linked glycosylation sites of wild-type human Factor VIII at amino acid residues 145 and 322 with reference to SEQ ID NO: 16 and further comprising mutation(s) in the Gla domain that increase the variant Factor VII polypeptide affinity for activated platelets;
   (2) contacting the sialylated Factor VII polypeptide with sialidase under conditions such that sufficient amounts of covalently attached sialic acid residues are removed from the sialylated Factor VII polypeptide to produce a desialylated Factor VII polypeptide having a ratio of moles of conjugated sialic acid to moles of N-linked glycan between 0 and 2.0 and (3) isolating the variant Factor VII polypeptide thereby produced.

7. A method of preparing the isolated variant Factor VII polypeptide according to claim 1, said method comprising
   (1) producing a Factor VII polypeptide comprising an amino acid sequence having at least 90% identity to the amino acid sequence of SEQ ID NO: 16 and comprising the N-linked glycosylation sites of wild-type human Factor VII at amino acid residues 145 and 322 with reference to SEQ ID NO: 16 and further comprising mutation(s) in the Gla domain that increase the variant Factor VII polypeptide affinity for activated platelets in a recombinant cell line that is deficient in its ability to sialylate peptides such that it produces a desialylated Factor VII polypeptide having a ratio of moles of conjugated sialic acid to moles of N-linked glycan between 0 and 2.0; and (2) isolating the variant Factor VII polypeptide thereby produced.

8. A method of preparing the isolated variant Factor VII polypeptide according to claim 1, said method comprising (1) obtaining a recombinant cell line that coexpresses (a) a recombinant Factor VII polypeptide comprising an amino acid sequence having at least 90% identity to the amino acid sequence of SEQ ID NO: 16 and comprising the N-linked glycosylation sites of wild-type human Factor VII at amino acid residues 145 and 322 with reference to SEQ ID NO: 16 and further comprising mutation(s) in the Gla domain that increase the variant Factor VII polypeptide affinity for activated platelets; and (b) a recombinant sialidase enzyme;

(2) culturing said recombinant cell line to allow expression of both the recombinant Factor VII polypeptide and the recombinant sialidase enzyme, wherein said recombinant sialidase enzyme removes sufficient amounts of covalently attached sialic acid residues to produce a desialylated Factor VII polypeptide having a ratio of moles of conjugated sialic acid to moles of N-linked glycan between 0 and 2.0; and (3) isolating the variant Factor VII polypeptide thereby produced.

9. A pharmaceutical composition comprising the isolated variant Factor VII polypeptide of claim 1 and a pharmaceutically acceptable excipient.

10. A method for treating a disease or a disorder wherein blood clot formation is desirable, said method comprising administering to a mammal in need thereof an effective amount of the isolated variant Factor VII polypeptide of claim 1, wherein the disease or disorder is selected from the group consisting of a hemorrhage, gastrointestinal bleeding, uncontrolled bleeding, bleeding in a mammal undergoing transplantation or resection or surgery, variceal bleeding, thrombocytopenia, hemophilia, intracranial hemorrhage, aortic aneurysm, over administration of an anticoagulant, penetrating traumatic injury; blunt traumatic injury; bleeding in elective surgery; bleeding in cardiac surgery; bleeding in spinal surgery; orthopedic surgery; neurosurgery; oncology surgery; post-partum surgery; menorrhagia; bleeding in stem cell transplantation; bleeding in liver transplantation; gastrointestinal bleeding; active variceal bleeding in cirrhosis; non variceal bleeding in cirrhosis; diffuse alveolar hemorrhage; aortic aneurysm; intracerebral hemorrhage; traumatic brain injury; brain contusion; reversal of warfarin; reversal of heparin; reversal of anticoagulants; reversal of anti-thrombotics; Factor VII deficiency; burns; prophylaxis in hemophilia patients with inhibitors; partial hepatectomy for non-cirrhotic and cirrhotic patients; acquired hemophilia; idiopathic thrombocytopenic purpura; Glanzmann's Thrombasthenia; Glanzmann's Thrombasthenia refractory to platelet transfusion and Bernard-Soulier Syndrome.

11. The method of claim 10, wherein the disease or disorder is a hemorrhage.

12. An isolated variant Factor VII polypeptide comprising an amino acid sequence having at least 90% identity to the amino acid sequence of SEQ ID NO: 16 and comprising mutation(s) that result in increased Factor VII polypeptide affinity for activated platelets, wherein the variant Factor VII polypeptide comprises N-linked glycosylation sites of wild-type human Factor VII at amino acid residues 145 and 322 with reference to SEQ ID NO: 16 and further wherein the variant Factor VII polypeptide has a ratio of moles of conjugated sialic acid to moles of N-linked glycan between 0 and 2.0.

13. The isolated variant Factor VII polypeptide of claim 12, wherein the variant Factor VII polypeptide comprises an amino acid sequence having at least 95% identity to the amino acid sequence of SEQ ID NO: 16.

14. The isolated variant Factor VII polypeptide of claim 12, wherein the variant Factor VII polypeptide comprises an amino acid sequence having at least 99% identity to the amino acid sequence of SEQ ID NO: 16.

15. The isolated variant Factor VII polypeptide of claim 12, wherein the variant Factor VII polypeptide comprises one or more additional N-linked glycosylation sites beyond the two present in wild type human Factor VII.

16. The isolated variant Factor VII polypeptide of claim 15, wherein the variant Factor VII polypeptide comprises the mutation T128N.

17. The isolated variant Factor VII polypeptide of claim 12, wherein the variant Factor VII polypeptide has a ratio of moles of conjugated sialic acid to moles of N-linked glycan that is less than 1.0.

18. The isolated variant Factor VII polypeptide of claim 12, wherein the variant Factor VII polypeptide has a ratio of moles of conjugated sialic acid to moles of N-linked glycan that is less than 0.1.

19. A method of preparing the isolated variant Factor VII polypeptide of claim 12, the method comprising (1) obtaining a sialylated Factor VII polypeptide comprising an amino acid sequence having at least 90% identity to the amino acid sequence of SEQ ID NO: 16 and comprising the N-linked glycosylation sites of wild-type human Factor VII at amino acid residues 145 and 322 with reference to SEQ ID NO: 16 and further comprising mutation(s) that result in increased Factor VII polypeptide affinity for activated platelets;

(2) contacting the sialylated Factor VII polypeptide with sialidase under conditions such that sufficient amounts of covalently attached sialic acid residues are removed from the sialylated Factor VII polypeptide to produce a desialylated Factor VII polypeptide having a ratio of moles of conjugated sialic acid to moles of N-linked glycan between 0 and 2.0 and (3) isolating the variant Factor VII polypeptide thereby produced.

20. A pharmaceutical composition comprising the isolated variant Factor VII polypeptide of claim 12 and a pharmaceutically acceptable excipient.

21. A method for treating a disease or a disorder wherein blood clot formation is desirable, said method comprising administering to a mammal in need thereof an effective amount of the isolated variant Factor VII polypeptide of claim 12, wherein the disease or disorder is selected from the group consisting of a hemorrhage, gastrointestinal bleeding, uncontrolled bleeding, bleeding in a mammal undergoing transplantation or resection or surgery, variceal bleeding, thrombocytopenia, hemophilia, intracranial hemorrhage, aortic aneurysm, over administration of an anticoagulant, penetrating traumatic injury; blunt traumatic injury; bleeding in elective surgery; bleeding in cardiac surgery; bleeding in spinal surgery; orthopedic surgery; neurosurgery; oncology surgery; post-partum surgery; menorrhagia; bleeding in stem cell transplantation; bleeding in liver transplantation;

gastrointestinal bleeding; active variceal bleeding in cirrhosis; non variceal bleeding in cirrhosis; diffuse alveolar hemorrhage; aortic aneurysm; intracerebral hemorrhage; traumatic brain injury; brain contusion; reversal of warfarin; reversal of heparin; reversal of anticoagulants; reversal of anti-thrombotics; Factor VII deficiency; burns; prophylaxis in hemophilia patients with inhibitors; partial hepatectomy for non-cirrhotic and cirrhotic patients; acquired hemophilia; idiopathic thrombocytopenic purpura; Glanzmann's Thrombasthenia; Glanzmann's Thrombasthenia refractory to platelet transfusion and Bernard-Soulier Syndrome.

22. The method of claim 21, wherein the disease or disorder is a hemorrhage.

* * * * *

SEQUENCE LISTING

```
<160> NUMBER OF SEQ ID NOS: 18

<210> SEQ ID NO 1
<211> LENGTH: 1218
<212> TYPE: DNA
<213> ORGANISM: Homo sapiens

<400> SEQUENCE: 1
gccaacgcgt tcctggagga gctgcggccg ggctccctgg agagggagtg caaggaggag      60
cagtgctcct tcgaggaggc ccgggagatc ttcaaggacg cggagaggac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aatacctatt     420
ctagaaaaaa gaaatgccag caaacccca ggccgaattg tgggggcaa ggtgtgcccc     480 aaaggggagt gtccatggca ggtcctgttg ttggtgaatg gagctcagtt gtgtggggg     540 accctgatca acaccatctg ggtggtctcc gcggcccact gtttcgacaa aatcaagaac     600
tggaggaacc tgatcgcggt gctgggcgag cacgacctca gcgagcacga cggggatgag     660
cagagccggc gggtggcgca ggtcatcatc cccagcacgt acgtcccggg caccaccaac     720
cacgacatcg cgctgctccg cctgcaccag cccgtggtcc tcactgacca tgtggtgccc     780
ctctgcctgc ccgaacggac gttctctgag aggacgctgg ccttcgtgcg cttctcattg     840
gtcagcggct ggggccagct gctggaccgt ggcgccacgg ccctggagct catggtcctc     900
aacgtgcccc ggctgatgac ccaggactgc ctgcagcagt cacggaaggt gggagactcc     960
ccaaatatca cggagtacat gttctgtgcc ggctactcgg atggcagcaa ggactcctgc    1020
aagggggaca gtggaggccc acatgccacc cactaccggg gcacgtggta cctgacgggc    1080
atcgtcagct ggggccaggg ctgcgcaacc gtgggccact tgggggtgta caccaggggtc    1140 tcccagtaca tcgagtggct gcaaaagctc atgcgctcag agccacgccc aggagtcctc    1200
```

```
ctgcgagccc catttccc                                              1218
```

<210> SEQ ID NO 2
<211> LENGTH: 1219
<212> TYPE: DNA
<213> ORGANISM: Artificial Sequence
<220> FEATURE:
<223> OTHER INFORMATION: Variant human FVII nucleotide sequence

<400> SEQUENCE: 2

```
gccaacgcgt tcctggagga gctgcggcag ggctccctgg agagggagtg caaggaggag    60
cagtgctcct tcgaggaggc ccgggagatc ttcgaagacg cggagaggac gaagctgttc   120
tggatttctt acagtgatgg ggaccagtgt gcctcaagtc catgccagaa tgggggctcc   180
tgcaaggacc agctccagtc ctatatctgc ttctgcctcc ctgccttcga gggccggaac   240
tgtgagacgc acaaggatga ccagctgatc tgtgtgaacg agaacggcgg ctgtgagcag   300
tactgcagtg accacaacgg caccaagcgc tcctgtcggt gccacgaggg gtactctctg   360
ctggcagacg gggtgtcctg cacacccaca gttgaatatc catgtggaaa aatacctatt   420
ctagaaaaaa gaaatgccag caaaccccaa ggccgaattg tggggggcaa ggtgtgcccc   480
aaaggggagt gtccatggca ggtcctgttg ttggtgaatg gagctcagtt gtgtggggga   540
accctgatca acaccatctg ggtggtctcc gcggcccact gtttcgacaa aatcaagaac   600
tggaggaacc tgatcgcggt gctgggcgag acgacctca gcgagcacga cggggatgag   660
cagagccggc gggtggcgca ggtcatcatc cccagcacgt acgtcccggg caccaccaac   720
cacgacatcg cgctgctccg cctgcaccag cccgtgaacc tcactgacca tgtggtgccc   780
ctctgcctgc ccgaacggac gttctctgag aggacgctgg ccttcgtgcg cttctcattg   840
gtcagcggct ggggccagct gctggaccgt ggcgccacgg ccctggagct catggtcctc   900
aacgtgcccc ggctgatgac ccaggactgc ctgcagcagt cacggaaggt gggagactcc   960
ccaaatatca cggagtacat gttctgtgcc ggctactcgg atggcagcaa ggactcctgc  1020
aaggggaca gtggaggccc catgccacc cactaccggg gcacgtggta cctgacgggc  1080
atcgtcagct ggggccaggg ctgcgcaacc gtgggccact tgggggtgta caccagggtc  1140
tcccagtaca tcgagtggct gcaaaagctc atgcgctcag agccacgccc aggagtcctc  1200
ctgcgagccc catttccct                                              1219
```

<210> SEQ ID NO 3
<211> LENGTH: 1218
<212> TYPE: DNA
<213> ORGANISM: Artificial Sequence
<220> FEATURE:
<223> OTHER INFORMATION: Variant human FVII nucleotide sequence

<400> SEQUENCE: 3

```
gccaacgcgt tcctggagga gctgcggcag ggctccctgg agagggagtg caaggaggag    60
cagtgctcct tcgaggaggc ccgggagatc ttcgaagacg aagaggaaac gaagctgttc   120
tggatttctt acagtgatgg ggaccagtgt gcctcaagtc catgccagaa tgggggctcc   180
tgcaaggacc agctccagtc ctatatctgc ttctgcctcc ctgccttcga gggccggaac   240
tgtgagacgc acaaggatga ccagctgatc tgtgtgaacg agaacggcgg ctgtgagcag   300
tactgcagtg accacaacgg caccaagcgc tcctgtcggt gccacgaggg gtactctctg   360
ctggcagacg gggtgtcctg cacacccaca gttgaatatc catgtggaaa aatacctatt   420
ctagaaaaaa gaaatgccag caaaccccaa ggccgaattg tggggggcaa ggtgtgcccc   480
```

```
aaaggggagt gtccatggca ggtcctgttg ttggtgaatg gagctcagtt gtgtggnggg      540
accctgatca acaccatctg ggtggtctcc gcggcccact gtttcgacaa aatcaagaac      600
tggaggaacc tgatcgcggt gctgggcgag cacgacctca gcgagcacga cggggatgag      660
cagagccggc gggtggcgca ggtcatcatc cccagcacgt acgtcccggg caccaccaac      720
cacgacatcg cgctgctccg cctgcaccag cccgtgaacc tcactgacca tgtggtgccc      780
ctctgcctgc ccgaacggac gttctctgag aggacgctgg ccttcgtgcg cttctcattg      840
gtcagcggct ggggccagct gctggaccgt ggcgccacgg ccctggagct catggtcctc      900
aacgtgcccc ggctgatgac ccaggactgc ctgcagcagt cacggaaggt gggagactcc      960
ccaaatatca cggagtacat gttctgtgcc ggctactcgg atggcagcaa ggactcctgc     1020 aaggggggaca gtggaggccc acatgccacc cactaccggg gcacgtggta cctgacgggc     1080
atcgtcagct ggggccaggg ctgcgcaacc gtgggccact ttggggtgta caccagggtc     1140
tcccagtaca tcgagtggct gcaaaagctc atgcgctcag agccacgccc aggagtcctc     1200
ctgcgagccc catttccc                                                   1218

<210> SEQ ID NO 4
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 4
gccaacgcgt tcctggagga gctgcggccg ggctccctgg agagggagtg caaggaggag       60
cagtgctcct tcgaggaggc ccgggagatc ttcaaggacg cggagaggac gaagctgttc      120
tggatttctt acagtgatgg ggaccagtgt gcctcaagtc catgccagaa tggggggctcc      180 tgcaaggacc agctccagtc ctatatctgc ttctgcctcc ctgccttcga gggccggaac      240
tgtgagacgc acaaggatga ccagctgatc tgtgtgaacg agaacggcgg ctgtgagcag      300
tactgcagtg accacacggg caccaagcgc tcctgtcggt gccacgaggg gtactctctg      360
ctggcagacg gggtgtcctg cacacccaca gttaatatc catgtggaaa atacctatt      420 ctagaaaaaa gaaatgccag caaaccccaa ggccgaattg tgggggggcaa ggtgtgcccc      480 aaaggggagt gtccatggca ggtcctgttg ttggtgaatg gagctcagtt gtgtgggggg      540
accctgatca acaccatctg ggtggtctcc gcggcccact gtttcgacaa aatcaagaac      600
tggaggaacc tgatcgcggt gctgggcgag cacgacctca gcgagcacga cggggatgag      660
cagagccggc gggtggcgca ggtcatcatc cccagcacgt acgtcccggg caccaccaac      720
cacgacatcg cgctgctccg cctgcaccag cccgtggtcc tcactgacca tgtggtgccc      780
ctctgcctgc ccgaacggac gttctctgag aggacgctgg ccttcgtgcg cttctcattg      840
gtcagcggct ggggccagct gctggaccgt ggcgccacgg ccctggagct catggtcctc      900
aacgtgcccc ggctgatgac ccaggactgc ctgcagcagt cacggaaggt gggagactcc      960
ccaaatatca cggagtacat gttctgtgcc ggctactcgg atggcagcaa ggactcctgc     1020 aaggggggaca gtggaggccc acatgccacc cactaccggg gcacgtggta cctgacgggc     1080
atcgtcagct ggggccaggg ctgcgcaacc gtgggccact ttggggtgta caccagggtc     1140
tcccagtaca tcgagtggct gcaaaagctc atgcgctcag agccacgccc aggagtcctc     1200
ctgcgagccc catttccc                                                   1218
```

<210> SEQ ID NO 5
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 5

| | | | | | |
|---|---|---|---|---|---|
| gccaacgcgt | tcctggagga | gctgcggccg | ggctccctgg | agagggagtg | caaggaggag | 60 |
| cagtgctcct | tcgaggaggc | ccgggagatc | ttcaaggacg | cggagaggac | gaagctgttc | 120 |
| tggatttctt | acagtgatgg | ggaccagtgt | gcctcaagtc | catgccagaa | tgggggctcc | 180 |
| tgcaaggacc | agctccagtc | ctatatctgc | ttctgcctcc | ctgccttcga | gggccggaac | 240 |
| tgtgagacgc | acaaggatga | ccagctgatc | tgtgtgaacg | agaacggcgg | ctgtgagcag | 300 |
| tactgcagtg | accacacggg | caccaagcgc | tcctgtcggt | gccacgaggg | gtactctctg | 360 |
| ctggcagacg | gggtgtcctg | cacacccaca | gttgaatatc | catgtggaaa | aatacctatt | 420 |
| ctagaaaaaa | gacaggccag | caaaccccaa | ggccgaattg | tggggggcaa | ggtgtgcccc | 480 |
| aaaggggagt | gtccatggca | ggtcctgttg | ttggtgaatg | gagctcagtt | gtgtgggggg | 540 |
| accctgatca | acaccatctg | ggtggtctcc | gcggcccact | gtttcgacaa | aatcaagaac | 600 |
| tggaggaacc | tgatcgcggt | gctgggcgag | cacgacctca | gcgagcacga | cggggatgag | 660 |
| cagagccggc | gggtggcgca | ggtcatcatc | cccagcacgt | acgtcccggg | caccaccaac | 720 |
| cacgacatcg | cgctgctccg | cctgcaccag | cccgtggtcc | tcactgacca | tgtggtgccc | 780 |
| ctctgcctgc | ccgaacggac | gttctctgag | aggacgctgg | ccttcgtgcg | cttctcattg | 840 |
| gtcagcggct | ggggccagct | gctggaccgt | ggcgccacgg | ccctggagct | catggtcctc | 900 |
| aacgtgcccc | ggctgatgac | ccaggactgc | ctgcagcagt | cacggaaggt | gggagactcc | 960 |
| ccaaatatca | cggagtacat | gttctgtgcc | ggctactcgg | atggcagcaa | ggactcctgc | 1020 |
| aagggggaca | gtggaggccc | acatgccacc | cactaccggg | gcacgtggta | cctgacgggc | 1080 |
| atcgtcagct | ggggccaggg | ctgcgcaacc | gtgggccact | tggggtgta | caccagggtc | 1140 |
| tcccagtaca | tcgagtggct | gcaaaagctc | atgcgctcag | agccacgccc | aggagtcctc | 1200 |
| ctgcgagccc | catttccc | | | | | 1218 |

<210> SEQ ID NO 6
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 6

| | | | | | |
|---|---|---|---|---|---|
| gccaacgcgt | tcctggagga | gctgcggccg | ggctccctgg | agagggagtg | caaggaggag | 60 |
| cagtgctcct | tcgaggaggc | ccgggagatc | ttcaaggacg | cggagaggac | gaagctgttc | 120 |
| tggatttctt | acagtgatgg | ggaccagtgt | gcctcaagtc | catgccagaa | tgggggctcc | 180 |
| tgcaaggacc | agctccagtc | ctatatctgc | ttctgcctcc | ctgccttcga | gggccggaac | 240 |
| tgtgagacgc | acaaggatga | ccagctgatc | tgtgtgaacg | agaacggcgg | ctgtgagcag | 300 |
| tactgcagtg | accacacggg | caccaagcgc | tcctgtcggt | gccacgaggg | gtactctctg | 360 |
| ctggcagacg | gggtgtcctg | cacacccaca | gttgaatatc | catgtggaaa | aatacctatt | 420 |
| ctagaaaaaa | gaaatgccag | caaaccccaa | ggccgaattg | tggggggcaa | ggtgtgcccc | 480 |
| aaaggggagt | gtccatggca | ggtcctgttg | ttggtgaatg | gagctcagtt | gtgtgggggg | 540 |

```
accctgatca acaccatctg ggtggtctcc gcggcccact gtttcgacaa aatcaagaac    600
tggaggaacc tgatcgcggt gctgggcgag cacgacctca gcgagcacga cggggatgag    660
cagagccggc gggtggcgca ggtcatcatc cccagcacgt acgtcccggg caccaccaac    720
cacgacatcg cgctgctccg cctgcaccag cccgtggtcc tcactgacca tgtggtgccc    780
ctctgcctgc ccgaacggac gttctctgag aggacgctgg ccttcgtgcg cttctcattg    840
gtcagcggct ggggccagct gctggaccgt ggcgccacgg ccctggagct catggtcctc    900
aacgtgcccc ggctgatgac ccaggactgc ctgcagcagt cacggaaggt gggagactcc    960
ccacagatca cggagtacat gttctgtgcc ggctactcgg atggcagcaa ggactcctgc   1020 aaggggggaca gtggaggccc acatgccacc cactaccggg gcacgtggta cctgacgggc   1080
atcgtcagct ggggccaggg ctgcgcaacc gtgggccact ttggggtgta caccagggtc   1140
tcccagtaca tcgagtggct gcaaaagctc atgcgctcag agccacgccc aggagtcctc   1200
ctgcgagccc catttccc                                                  1218
```

<210> SEQ ID NO 7
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 7

```
gccaacgcgt tcctggagga gctgcggccg ggctccctgg agagggagtg caaggaggag     60
cagtgctcct tcgaggaggc ccgggagatc ttcaaggacg cggagaggac gaagctgttc    120
tggatttctt acagtgatgg ggaccagtgt gcctcaagtc catgccagaa tgggggctcc    180
tgcaaggacc agctccagtc ctatatctgc ttctgcctcc ctgccttcga gggccggaac    240
tgtgagacgc acaaggatga ccagctgatc tgtgtgaacg agaacggcgg ctgtgagcag    300
tactgcagtg accacacggg caccaagcgc tcctgtcggt gccacgaggg gtactctctg    360
ctggcagacg gggtgtcctg cacacccaca gttgaatatc catgtggaaa aatacctatt    420
ctagaaaaaa gacaggccag caaaccccaa ggccgaattg tggggggcaa ggtgtgcccc    480 aaagggagt gtccatggca ggtcctgttg ttggtgaatg gagctcagtt gtgtgggggg    540
accctgatca acaccatctg ggtggtctcc gcggcccact gtttcgacaa aatcaagaac    600
tggaggaacc tgatcgcggt gctgggcgag cacgacctca gcgagcacga cggggatgag    660
cagagccggc gggtggcgca ggtcatcatc cccagcacgt acgtcccggg caccaccaac    720
cacgacatcg cgctgctccg cctgcaccag cccgtggtcc tcactgacca tgtggtgccc    780
ctctgcctgc ccgaacggac gttctctgag aggacgctgg ccttcgtgcg cttctcattg    840
gtcagcggct ggggccagct gctggaccgt ggcgccacgg ccctggagct catggtcctc    900
aacgtgcccc ggctgatgac ccaggactgc ctgcagcagt cacggaaggt gggagactcc    960
ccacagatca cggagtacat gttctgtgcc ggctactcgg atggcagcaa ggactcctgc   1020 aaggggggaca gtggaggccc acatgccacc cactaccggg gcacgtggta cctgacgggc   1080
atcgtcagct ggggccaggg ctgcgcaacc gtgggccact ttggggtgta caccagggtc   1140
tcccagtaca tcgagtggct gcaaaagctc atgcgctcag agccacgccc aggagtcctc   1200
ctgcgagccc catttccc                                                  1218
```

<210> SEQ ID NO 8

```
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 8
gccaacgcgt tcctggagga gctgcggcag ggctccctgg agagggagtg caaggaggag      60
cagtgctcct tcgaggaggc ccgggagatc ttcgaagacg cggagaggac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aataccattt     420
ctagaaaaaa gaaatgccag caaacccaa ggccgaattg tggggggcaa ggtgtgcccc     480 aaagggagt gtccatggca ggtcctgttg ttggtgaatg gagctcagtt gtgtgggggg     540
accctgatca acaccatctg ggtggtctcc gcggcccact gtttcgacaa aatcaagaac     600
tggaggaacc tgatcgcggt gctgggcgag acgacctca gcgagcacga cggggatgag     660
cagagccggc gggtggcgca ggtcatcatc cccagcacgt acgtcccggg caccaccaac     720
cacgacatcg cgctgctccg cctgcaccag cccgtggtcc tcactgacca gtggtgccc     780 ctctgcctgc ccgaacggac gttctctgag aggacgctgg ccttcgtgcg cttctcattg     840
gtcagcggct ggggccagct gctggaccgt ggcgccacgg ccctggagct catggtcctc     900
aacgtgcccc ggctgatgac ccaggactgc ctgcagcagt cacggaaggt gggagactcc     960
ccaaatatca cggagtacat gttctgtgcc ggctactcgg atggcagcaa ggactcctgc    1020
aagggggaca gtggaggccc acatgccacc cactaccggg gcacgtggta cctgacgggc    1080
atcgtcagct ggggccaggg ctgcgcaacc gtgggccact tgggggtgta caccaggggtc    1140 tcccagtaca tcgagtggct gcaaaagctc atgcgctcag agccacgccc aggagtcctc    1200
ctgcgagccc catttccc                                                 1218

<210> SEQ ID NO 9
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 9
gccaacgcgt tcctggagga gctgcggcag ggctccctgg agagggagtg caaggaggag      60
cagtgctcct tcgaggaggc ccgggagatc ttcgaagacg cggagaggac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aataccattt     420
ctagaaaaaa gacaggccag caaacccaa ggccgaattg tggggggcaa ggtgtgcccc     480 aaagggagt gtccatggca ggtcctgttg ttggtgaatg gagctcagtt gtgtgggggg     540
accctgatca acaccatctg ggtggtctcc gcggcccact gtttcgacaa aatcaagaac     600
```

-continued

```
tggaggaacc tgatcgcggt gctgggcgag cacgacctca gcgagcacga cggggatgag      660
cagagccggc gggtggcgca ggtcatcatc cccagcacgt acgtcccggg caccaccaac      720
cacgacatcg cgctgctccg cctgcaccag cccgtggtcc tcactgacca tgtggtgccc      780
ctctgcctgc ccgaacggac gttctctgag aggacgctgg ccttcgtgcg cttctcattg      840
gtcagcggct ggggccagct gctggaccgt ggcgccacgg ccctggagct catggtcctc      900
aacgtgcccc ggctgatgac ccaggactgc ctgcagcagt cacggaaggt gggagactcc      960
ccaaatatca cggagtacat gttctgtgcc ggctactcgg atggcagcaa ggactcctgc     1020 aaggggaca gtgaggccc acatgccacc cactaccggg gcacgtggta cctgacgggc      1080
atcgtcagct ggggccaggg ctgcgcaacc gtgggccact ttggggtgta caccagggtc     1140
tcccagtaca tcgagtggct gcaaaagctc atgcgctcag agccacgccc aggagtcctc     1200
ctgcgagccc catttccc                                                    1218
```

<210> SEQ ID NO 10
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 10

```
gccaacgcgt tcctggagga gctgcggcag ggctccctgg agagggagtg caaggaggag       60
cagtgctcct tcgaggaggc ccggagatc ttcgaagacg cggagaggac gaagctgttc      120
tggatttctt acagtgatgg ggaccagtgt gcctcaagtc catgccagaa tggggggctcc     180 tgcaaggacc agctccagtc ctatatctgc ttctgcctcc ctgccttcga gggccggaac      240
tgtgagacgc acaaggatga ccagctgatc tgtgtgaacg agaacggcgg ctgtgagcag      300
tactgcagtg accacacggg caccaagcgc tcctgtcggt gccacgaggg gtactctctg      360
ctggcagacg gggtgtcctg cacacccaca gttgaatatc catgtggaaa atacctatt      420 ctagaaaaaa gaaatgccag caaacccaa ggccgaattg tgggggcaa ggtgtgcccc       480 aaaggggagt gtccatggca ggtcctgttg ttggtgaatg gagctcagtt gtgtgggggg      540
accctgatca acaccatctg ggtggtctcc gcggcccact gtttcgacaa aatcaagaac      600
tggaggaacc tgatcgcggt gctgggcgag cacgacctca gcgagcacga cggggatgag      660
cagagccggc gggtggcgca ggtcatcatc cccagcacgt acgtcccggg caccaccaac      720
cacgacatcg cgctgctccg cctgcaccag cccgtggtcc tcactgacca tgtggtgccc      780
ctctgcctgc ccgaacggac gttctctgag aggacgctgg ccttcgtgcg cttctcattg      840
gtcagcggct ggggccagct gctggaccgt ggcgccacgg ccctggagct catggtcctc      900
aacgtgcccc ggctgatgac ccaggactgc ctgcagcagt cacggaaggt gggagactcc      960
ccacagatca cggagtacat gttctgtgcc ggctactcgg atggcagcaa ggactcctgc     1020 aaggggaca gtgaggccc acatgccacc cactaccggg gcacgtggta cctgacgggc      1080
atcgtcagct ggggccaggg ctgcgcaacc gtgggccact ttggggtgta caccagggtc     1140
tcccagtaca tcgagtggct gcaaaagctc atgcgctcag agccacgccc aggagtcctc     1200
ctgcgagccc catttccc                                                    1218
```

<210> SEQ ID NO 11
<211> LENGTH: 1218
<212> TYPE: DNA

<213> ORGANISM: Artificial Sequence
<220> FEATURE:
<223> OTHER INFORMATION: Plasmid sequence

<400> SEQUENCE: 11

```
gccaacgcgt tcctggagga gctgcggcag ggctccctgg agagggagtg caaggaggag      60
cagtgctcct tcgaggaggc ccgggagatc ttcgaagacg cggagaggac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aatacctatt     420
ctagaaaaaa gacaggccag caaaccccaa ggccgaattg tggggggcaa ggtgtgcccc     480
aaagggagt gtccatggca ggtcctgttg ttggtgaatg gagctcagtt gtgtgggggg     540
accctgatca acaccatctg gtggtctcc gcggcccact gtttcgacaa aatcaagaac     600
tggaggaacc tgatcgcggt gctgggcgag cacgacctca gcgagcacga cggggatgag     660
cagagccggc gggtggcgca ggtcatcatc cccagcacgt acgtcccggg caccaccaac     720
cacgacatcg cgctgctccg cctgcaccag cccgtggtcc tcactgacca tgtggtgccc     780
ctctgcctgc ccgaacggac gttctctgag aggacgctgg ccttcgtgcg cttctcattg     840
gtcagcggct ggggccagct gctggaccgt ggcgccacgg ccctggagct catggtcctc     900
aacgtgcccc ggctgatgac ccaggactgc ctgcagcagt cacggaaggt gggagactcc     960
ccacagatca cggagtacat gttctgtgcc ggctactcgg atggcagcaa ggactcctgc    1020
aagggggaca gtgagggccc acatgccacc cactaccggg gcacgtggta cctgacgggc    1080
atcgtcagct ggggccaggg ctgcgcaacc gtgggccact ttgggggtgta caccagggtc    1140
tcccagtaca tcgagtggct gcaaaagctc atgcgctcag agccacgccc aggagtcctc    1200
ctgcgagccc catttccc                                                  1218
```

<210> SEQ ID NO 12
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 12

```
gccaacgcgt tcctggagga gctgcggcag ggctccctgg agagggagtg caaggaggag      60
cagtgctcct tcgaggaggc ccgggagatc ttcgaagacg aagaggaaac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aatacctatt     420
ctagaaaaaa gaaatgccag caaaccccaa ggccgaattg tggggggcaa ggtgtgcccc     480
aaagggagt gtccatggca ggtcctgttg ttggtgaatg gagctcagtt gtgtgggggg     540
accctgatca acaccatctg gtggtctcc gcggcccact gtttcgacaa aatcaagaac     600
tggaggaacc tgatcgcggt gctgggcgag cacgacctca gcgagcacga cggggatgag     660
```

```
cagagccggc gggtggcgca ggtcatcatc cccagcacgt acgtcccggg caccaccaac    720
cacgacatcg cgctgctccg cctgcaccag cccgtggtcc tcactgacca tgtggtgccc    780
ctctgcctgc ccgaacggac gttctctgag aggacgctgg ccttcgtgcg cttctcattg    840
gtcagcggct ggggccagct gctggaccgt ggcgccacgg ccctggagct catggtcctc    900
aacgtgcccc ggctgatgac ccaggactgc ctgcagcagt cacggaaggt gggagactcc    960
ccaaatatca cggagtacat gttctgtgcc ggctactcgg atggcagcaa ggactcctgc   1020
aagggggaca gtggaggccc acatgccacc cactaccggg gcacgtggta cctgacgggc   1080
atcgtcagct ggggccaggg ctgcgcaacc gtgggccact ttgggtgta caccagggtc    1140 tcccagtaca tcgagtggct gcaaaagctc atgcgctcag agccacgccc aggagtcctc   1200
ctgcgagccc catttccc                                                1218

<210> SEQ ID NO 13
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 13
gccaacgcgt tcctggagga gctgcggcag ggctccctgg agagggagtg caaggaggag     60
cagtgctcct tcgaggaggc ccgggagatc ttcgaagacg aagaggaaac gaagctgttc    120
tggatttctt acagtgatgg ggaccagtgt gcctcaagtc catgccagaa tgggggctcc    180
tgcaaggacc agctccagtc ctatatctgc ttctgcctcc ctgccttcga gggccggaac    240
tgtgagacgc acaaggatga ccagctgatc tgtgtgaacg agaacggcgg ctgtgagcag    300
tactgcagtg accacacggg caccaagcgc tcctgtcggt gccacgaggg gtactctctg    360
ctggcagacg gggtgtcctg cacacccaca gttgaatatc catgtggaaa aatacctatt    420
ctagaaaaaa gacaggccag caaaccccaa ggccgaattg tggggggcaa ggtgtgcccc    480 aaagggagt gtccatggca ggtcctgttg ttggtgaatg gagctcagtt gtgtgggggg    540
accctgatca acaccatctg ggtggtctcc gcggcccact gtttcgacaa aatcaagaac    600
tggaggaacc tgatcgcggt gctgggcgag cacgacctca gcgagcacga cggggatgag    660
cagagccggc gggtggcgca ggtcatcatc cccagcacgt acgtcccggg caccaccaac    720
cacgacatcg cgctgctccg cctgcaccag cccgtggtcc tcactgacca tgtggtgccc    780
ctctgcctgc ccgaacggac gttctctgag aggacgctgg ccttcgtgcg cttctcattg    840
gtcagcggct ggggccagct gctggaccgt ggcgccacgg ccctggagct catggtcctc    900
aacgtgcccc ggctgatgac ccaggactgc ctgcagcagt cacggaaggt gggagactcc    960
ccaaatatca cggagtacat gttctgtgcc ggctactcgg atggcagcaa ggactcctgc   1020
aagggggaca gtggaggccc acatgccacc cactaccggg gcacgtggta cctgacgggc   1080
atcgtcagct ggggccaggg ctgcgcaacc gtgggccact ttgggtgta caccagggtc    1140 tcccagtaca tcgagtggct gcaaaagctc atgcgctcag agccacgccc aggagtcctc   1200
ctgcgagccc catttccc                                                1218

<210> SEQ ID NO 14
<211> LENGTH: 1218
<212> TYPE: DNA
<213> ORGANISM: Artificial Sequence
<220> FEATURE:
```

<223> OTHER INFORMATION: Plasmid sequence

<400> SEQUENCE: 14

```
gccaacgcgt tcctggagga gctgcggcag ggctccctgg agagggagtg caaggaggag      60
cagtgctcct tcgaggaggc ccgggagatc ttcgaagacg aagaggaaac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aatacctatt     420
ctagaaaaaa gaaatgccag caaacccaa ggccgaattg tggggggcaa ggtgtgcccc      480
aaagggagt gtccatggca ggtcctgttg ttggtgaatg gagctcagtt gtgtggggg      540
accctgatca acaccatctg ggtggtctcc gcggcccact gtttcgacaa aatcaagaac     600
tggaggaacc tgatcgcggt gctgggcgag acgacctca gcgagcacga cggggatgag      660
cagagccggc gggtggcgca ggtcatcatc cccagcacgt acgtcccggg caccaccaac     720
cacgacatcg cgctgctccg cctgcaccag cccgtggtcc tcactgacca tgtggtgccc     780
ctctgcctgc ccgaacggac gttctctgag aggacgctgg ccttcgtgcg cttctcattg     840
gtcagcggct ggggccagct gctggaccgt ggcgccacgg ccctggagct catggtcctc     900
aacgtgcccc ggctgatgac ccaggactgc ctgcagcagt cacggaaggt gggagactcc     960
ccacagatca cggagtacat gttctgtgcc ggctactcgg atggcagcaa ggactcctgc    1020
aaggggaca gtggaggccc acatgccacc cactaccggg gcacgtggta cctgacgggc    1080
atcgtcagct ggggccaggg ctgcgcaacc gtgggccact tgggggtgta caccagggtc    1140
tcccagtaca tcgagtggct gcaaaagctc atgcgctcag agccacgccc aggagtcctc    1200
ctgcgagccc catttccc                                                  1218
```

<210> SEQ ID NO 15
<211> LENGTH: 1218
<212> TYPE: DNA
<213> ORGANISM: Artificial Sequence
<220> FEATURE:
<223> OTHER INFORMATION: Plasmid sequence

<400> SEQUENCE: 15

```
gccaacgcgt tcctggagga gctgcggcag ggctccctgg agagggagtg caaggaggag      60
cagtgctcct tcgaggaggc ccgggagatc ttcgaagacg aagaggaaac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aatacctatt     420
ctagaaaaaa gacaggccag caaacccaa ggccgaattg tggggggcaa ggtgtgcccc      480
aaagggagt gtccatggca ggtcctgttg ttggtgaatg gagctcagtt gtgtggggg      540
accctgatca acaccatctg ggtggtctcc gcggcccact gtttcgacaa aatcaagaac     600
tggaggaacc tgatcgcggt gctgggcgag acgacctca gcgagcacga cggggatgag      660
cagagccggc gggtggcgca ggtcatcatc cccagcacgt acgtcccggg caccaccaac     720
```

-continued

```
cacgacatcg cgctgctccg cctgcaccag cccgtggtcc tcactgacca tgtggtgccc    780
ctctgcctgc ccgaacggac gttctctgag aggacgctgg ccttcgtgcg cttctcattg    840
gtcagcggct ggggccagct gctggaccgt ggcgccacgg ccctggagct catggtcctc    900
aacgtgcccc ggctgatgac ccaggactgc ctgcagcagt cacggaaggt gggagactcc    960
ccacagatca cggagtacat gttctgtgcc ggctactcgg atggcagcaa ggactcctgc   1020 aaggggggaca gtggaggccc acatgccacc cactaccggg gcacgtggta cctgacgggc   1080
atcgtcagct ggggccaggg ctgcgcaacc gtgggccact ttggggtgta caccagggtc   1140
tcccagtaca tcgagtggct gcaaaagctc atgcgctcag agccacgccc aggagtcctc   1200
ctgcgagccc catttccc                                                 1218
```

<210> SEQ ID NO 16
<211> LENGTH: 406
<212> TYPE: PRT
<213> ORGANISM: Homo sapiens

<400> SEQUENCE: 16

```
Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
```

```
                275                 280                 285
Asp Arg Gly Ala Thr Ala Leu Glu Leu Met Val Leu Asn Val Pro Arg
        290                 295                 300
Leu Met Thr Gln Asp Cys Leu Gln Gln Ser Arg Lys Val Gly Asp Ser
305                 310                 315                 320
Pro Asn Ile Thr Glu Tyr Met Phe Cys Ala Gly Tyr Ser Asp Gly Ser
                325                 330                 335
Lys Asp Ser Cys Lys Gly Asp Ser Gly Gly Pro His Ala Thr His Tyr
            340                 345                 350
Arg Gly Thr Trp Tyr Leu Thr Gly Ile Val Ser Trp Gly Gln Gly Cys
                355                 360                 365
Ala Thr Val Gly His Phe Gly Val Tyr Thr Arg Val Ser Gln Tyr Ile
            370                 375                 380
Glu Trp Leu Gln Lys Leu Met Arg Ser Glu Pro Arg Pro Gly Val Leu
385                 390                 395                 400
Leu Arg Ala Pro Phe Pro
                405

<210> SEQ ID NO 17
<211> LENGTH: 407
<212> TYPE: PRT
<213> ORGANISM: Artificial Sequence
<220> FEATURE:
<223> OTHER INFORMATION: Variant human FVII peptide sequence
<220> FEATURE:
<221> NAME/KEY: misc_feature
<222> LOCATION: (407)..(407)
<223> OTHER INFORMATION: Xaa can be any naturally occurring amino acid

<400> SEQUENCE: 17

Ala Asn Ala Phe Leu Glu Glu Leu Arg Gln Gly Ser Leu Glu Arg Glu
1               5                   10                  15
Cys Lys Glu Glu Gln Cys Ser Phe Glu Glu Ala Arg Glu Ile Phe Glu
            20                  25                  30
Asp Ala Glu Arg Thr Lys Leu Phe Trp Ile Ser Tyr Ser Asp Gly Asp
        35                  40                  45
Gln Cys Ala Ser Ser Pro Cys Gln Asn Gly Gly Ser Cys Lys Asp Gln
    50                  55                  60
Leu Gln Ser Tyr Ile Cys Phe Cys Leu Pro Ala Phe Glu Gly Arg Asn
65                  70                  75                  80
Cys Glu Thr His Lys Asp Asp Gln Leu Ile Cys Val Asn Glu Asn Gly
                85                  90                  95
Gly Cys Glu Gln Tyr Cys Ser Asp His Asn Gly Thr Lys Arg Ser Cys
            100                 105                 110
Arg Cys His Glu Gly Tyr Ser Leu Leu Ala Asp Gly Val Ser Cys Thr
        115                 120                 125
Pro Thr Val Glu Tyr Pro Cys Gly Lys Ile Pro Ile Leu Glu Lys Arg
    130                 135                 140
Asn Ala Ser Lys Pro Gln Gly Arg Ile Val Gly Gly Lys Val Cys Pro
145                 150                 155                 160
Lys Gly Glu Cys Pro Trp Gln Val Leu Leu Leu Val Asn Gly Ala Gln
                165                 170                 175
Leu Cys Gly Gly Thr Leu Ile Asn Thr Ile Trp Val Val Ser Ala Ala
            180                 185                 190
His Cys Phe Asp Lys Ile Lys Asn Trp Arg Asn Leu Ile Ala Val Leu
        195                 200                 205
```

```
Gly Glu His Asp Leu Ser Glu His Asp Gly Asp Gln Ser Arg Arg
    210             215             220
Val Ala Gln Val Ile Ile Pro Ser Thr Tyr Val Pro Gly Thr Thr Asn
225             230             235             240
His Asp Ile Ala Leu Leu Arg Leu His Gln Pro Val Asn Leu Thr Asp
                245             250             255
His Val Val Pro Leu Cys Leu Pro Glu Arg Thr Phe Ser Glu Arg Thr
                260             265             270
Leu Ala Phe Val Arg Phe Ser Leu Val Ser Gly Trp Gly Gln Leu Leu
                275             280             285
Asp Arg Gly Ala Thr Ala Leu Glu Leu Met Val Leu Asn Val Pro Arg
290             295             300
Leu Met Thr Gln Asp Cys Leu Gln Gln Ser Arg Lys Val Gly Asp Ser
305             310             315             320
Pro Asn Ile Thr Glu Tyr Met Phe Cys Ala Gly Tyr Ser Asp Gly Ser
                325             330             335
Lys Asp Ser Cys Lys Gly Asp Ser Gly Gly Pro His Ala Thr His Tyr
                340             345             350
Arg Gly Thr Trp Tyr Leu Thr Gly Ile Val Ser Trp Gly Gln Gly Cys
                355             360             365
Ala Thr Val Gly His Phe Gly Val Tyr Thr Arg Val Ser Gln Tyr Ile
370             375             380
Glu Trp Leu Gln Lys Leu Met Arg Ser Glu Pro Arg Pro Gly Val Leu
385             390             395             400
Leu Arg Ala Pro Phe Pro Xaa
                405

<210> SEQ ID NO 18
<211> LENGTH: 406
<212> TYPE: PRT
<213> ORGANISM: Artificial Sequence
<220> FEATURE:
<223> OTHER INFORMATION: Variant human FVII peptide sequence

<400> SEQUENCE: 18

Ala Asn Ala Phe Leu Glu Glu Leu Arg Gln Gly Ser Leu Glu Arg Glu
1               5               10              15
Cys Lys Glu Glu Gln Cys Ser Phe Glu Glu Ala Arg Glu Ile Phe Glu
                20              25              30
Asp Glu Glu Glu Thr Lys Leu Phe Trp Ile Ser Tyr Ser Asp Gly Asp
            35              40              45
Gln Cys Ala Ser Ser Pro Cys Gln Asn Gly Gly Ser Cys Lys Asp Gln
    50              55              60
Leu Gln Ser Tyr Ile Cys Phe Cys Leu Pro Ala Phe Glu Gly Arg Asn
65              70              75              80
Cys Glu Thr His Lys Asp Asp Gln Leu Ile Cys Val Asn Glu Asn Gly
                85              90              95
Gly Cys Glu Gln Tyr Cys Ser Asp His Asn Gly Thr Lys Arg Ser Cys
                100             105             110
Arg Cys His Glu Gly Tyr Ser Leu Leu Ala Asp Gly Val Ser Cys Thr
            115             120             125
Pro Thr Val Glu Tyr Pro Cys Gly Lys Ile Pro Ile Leu Glu Lys Arg
    130             135             140
Asn Ala Ser Lys Pro Gln Gly Arg Ile Val Gly Gly Lys Val Cys Pro
145             150             155             160
```

-continued

```
Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Asn Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405
```